US012746115B2

(12) United States Patent
Schwartz

(10) Patent No.: US 12,746,115 B2
(45) Date of Patent: Sep. 29, 2026

(54) APPARATUS AND METHODS FOR REDUCING PARAVALVULAR LEAKAGE

(71) Applicant: EDWARDS LIFESCIENCES CORPORATION, Irvine, CA (US)

(72) Inventor: Evan T. Schwartz, Huntington Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 623 days.

(21) Appl. No.: 18/308,525

(22) Filed: Apr. 27, 2023

(65) Prior Publication Data

US 2023/0255755 A1 Aug. 17, 2023

Related U.S. Application Data

(63) Continuation of application No. PCT/US2021/056964, filed on Oct. 28, 2021.

(Continued)

(51) Int. Cl.
*A61F 2/24* (2006.01)

(52) U.S. Cl.
CPC .......... *A61F 2/2409* (2013.01); *A61F 2/2418* (2013.01); *A61F 2230/0091* (2013.01);

(Continued)

(58) Field of Classification Search
CPC .................. A61F 2/2409; A61F 2/2418; A61F 2250/006; A61F 2250/0069; A61F 2230/0091
See application file for complete search history.

(56) References Cited

U.S. PATENT DOCUMENTS

| | | | |
|---|---|---|---|
| 4,035,849 A | 7/1977 | Angell et al. | |
| 4,164,046 A | 8/1979 | Cooley | |

(Continued)

FOREIGN PATENT DOCUMENTS

| | | | |
|---|---|---|---|
| DE | 19532846 A1 | 3/1997 | |
| DE | 19907646 A1 | 8/2000 | |

(Continued)

OTHER PUBLICATIONS

Walther, et al., "Trans-catheter valve-in-valve implantation: in vitro hydrodynamic performance of the SAPIEN + cloth trans-catheter heart valve in the Carpentier-Edwards Perimount valves," European Journal of Cardio-thoracic Surgery, 40 (2011) 1120-1126, Sep. 23, 2010.

*Primary Examiner* — Suba Ganesan
(74) *Attorney, Agent, or Firm* — Klarquist Sparkman LLP

(57) ABSTRACT

This disclosure is directed to a docking device for a prosthetic heart valve. The docking device includes an inflow end, an outflow end, a support structure disposed between the inflow end and the outflow end, and an expandable sleeve. The support structure includes inflow and outflow sections that are configured to be positioned on inflow and outflow sides, respectively, of a native heart valve. The outflow section includes a first portion, a second portion, and a third portion, wherein the first portion is disposed closer to the inflow section than the second portion, and wherein the third portion is disposed between the first and second portions. The expandable sleeve may extend at least 100 degrees over the first portion of the outflow section of the support structure. Additionally, or alternatively, the first portion of the outflow section of the support structure may have a different geometry than the third portion.

19 Claims, 16 Drawing Sheets

Related U.S. Application Data

(60) Provisional application No. 63/107,245, filed on Oct. 29, 2020.

(52) U.S. Cl.
CPC . *A61F 2250/006* (2013.01); *A61F 2250/0063* (2013.01); *A61F 2250/0069* (2013.01)

(56) References Cited

U.S. PATENT DOCUMENTS 4,790,843 A 12/1988 Carpentier et al.
5,059,177 A 10/1991 Towne et al.
5,411,552 A 5/1995 Andersen et al.
5,554,185 A 9/1996 Block et al.
5,840,081 A 11/1998 Andersen et al.
6,168,614 B1 1/2001 Andersen et al.
6,217,610 B1 4/2001 Carpentier et al.
6,368,348 B1 4/2002 Gabbay
6,419,696 B1 7/2002 Ortiz et al.
6,425,916 B1 7/2002 Garrison et al.
6,432,134 B1 8/2002 Anson et al.
6,458,153 B1 10/2002 Bailey et al.
6,527,979 B2 3/2003 Constantz et al.
6,582,462 B1 6/2003 Andersen et al.
6,652,578 B2 11/2003 Bailey et al.
6,730,121 B2 5/2004 Ortiz et al.
6,797,002 B2 9/2004 Spence et al.
6,908,481 B2 6/2005 Cribier
6,964,684 B2 11/2005 Ortiz et al.
7,018,408 B2 3/2006 Bailey et al.
7,037,334 B1 5/2006 Hlavka et al.
7,077,861 B2 7/2006 Spence
7,101,395 B2 9/2006 Tremulis et al.
7,125,421 B2 10/2006 Tremulis et al.
7,445,632 B2 11/2008 McGuckin, Jr. et al.
7,585,321 B2 9/2009 Cribier
7,618,446 B2 11/2009 Andersen et al.
7,637,946 B2 12/2009 Solem et al.
7,708,775 B2 5/2010 Rowe et al.
7,737,060 B2 6/2010 Strickler et al.
7,785,366 B2 8/2010 Maurer et al.
7,951,195 B2 5/2011 Antonsson et al.
8,128,691 B2 3/2012 Keranen
8,142,492 B2 3/2012 Forster et al.
8,236,049 B2 8/2012 Rowe et al.
8,323,335 B2 12/2012 Rowe et al.
8,377,115 B2 2/2013 Thompson
8,398,708 B2 3/2013 Meiri et al.
8,449,599 B2 5/2013 Chau et al.
8,449,605 B2 5/2013 Lichtenstein et al.
8,449,606 B2 5/2013 Eliasen et al.
8,657,872 B2 2/2014 Seguin
8,663,322 B2 3/2014 Keranen
8,672,998 B2 3/2014 Lichtenstein et al.
8,685,086 B2 4/2014 Navia et al.
8,734,507 B2 5/2014 Keranen
8,801,776 B2 8/2014 House et al.
8,840,664 B2 9/2014 Karapetian et al.
9,078,747 B2 7/2015 Conklin
9,095,434 B2 8/2015 Rowe
9,119,718 B2 9/2015 Keranen
9,192,471 B2 11/2015 Bolling
9,237,886 B2 1/2016 Seguin et al.
9,314,335 B2 4/2016 Konno
9,326,853 B2 5/2016 Olson et al.
9,364,326 B2 6/2016 Yaron
9,463,268 B2 10/2016 Spence
9,474,599 B2 10/2016 Keranen
9,526,572 B2 12/2016 Kunis
9,597,205 B2 3/2017 Tuval
9,622,863 B2 4/2017 Karapetian et al.
9,867,702 B2 1/2018 Keränen et al.
10,016,272 B2 7/2018 Spence et al.
10,016,276 B2 7/2018 Brunnett et al.
10,034,749 B2 7/2018 Spence et al.
10,039,637 B2 8/2018 Maimon et al.
10,052,198 B2 8/2018 Chau et al.
10,195,028 B2 2/2019 Hosmer et al.
10,195,033 B2 2/2019 Tuval et al.
10,226,339 B2 3/2019 Spence et al.
10,357,361 B2 7/2019 Rafi et al.
10,463,479 B2 11/2019 Manash et al.
10,828,150 B2 11/2020 Tamir
11,020,225 B2 6/2021 Keränen et al.
11,039,924 B2 6/2021 Yaron
11,065,111 B2 7/2021 Manash et al.
11,141,273 B2 10/2021 Dakin et al.
11,185,406 B2 11/2021 Haivatov et al.
11,364,114 B2 6/2022 Gorman, III et al.
11,382,748 B2 7/2022 Keränen et al.
11,471,282 B2 10/2022 Argento et al.
11,547,563 B2 1/2023 Keränen et al.
11,654,025 B2 5/2023 O'Carroll et al.
11,666,441 B2 6/2023 McDaniel et al.
2002/0032481 A1 3/2002 Gabbay
2002/0107535 A1 8/2002 Wei et al.
2002/0151970 A1 10/2002 Garrison et al.
2002/0173841 A1 11/2002 Ortiz et al.
2003/0225420 A1 12/2003 Wardle
2004/0111006 A1 6/2004 Alferness et al.
2004/0260389 A1 12/2004 Case et al.
2005/0043791 A1 2/2005 McCarthy et al.
2005/0096736 A1 5/2005 Osse et al.
2005/0119682 A1 6/2005 Nguyen et al.
2005/0119735 A1 6/2005 Spence et al.
2005/0137691 A1 6/2005 Salahieh et al.
2005/0182486 A1 8/2005 Gabbay
2005/0203614 A1 9/2005 Forster et al.
2005/0203617 A1 9/2005 Forster et al.
2005/0256567 A1 11/2005 Lim et al.
2006/0025857 A1 2/2006 Bergheim et al.
2006/0025858 A1 2/2006 Alameddine
2006/0195134 A1 8/2006 Crittenden
2006/0195185 A1 8/2006 Lane et al.
2006/0271172 A1 11/2006 Tehrani
2007/0179604 A1 8/2007 Lane
2007/0203575 A1 8/2007 Forster et al.
2007/0265700 A1 11/2007 Eliasen et al.
2007/0293808 A1 12/2007 Williams et al.
2008/0033542 A1 2/2008 Antonsson et al.
2008/0077235 A1 3/2008 Kirson
2008/0125853 A1 5/2008 Bailey et al.
2008/0140190 A1 6/2008 Macoviak et al.
2008/0208327 A1 8/2008 Rowe
2008/0208330 A1 8/2008 Keranen
2009/0192601 A1 7/2009 Rafiee et al.
2009/0276038 A1 11/2009 Tremulis et al.
2009/0319037 A1 12/2009 Rowe et al.
2010/0036484 A1 2/2010 Hariton et al.
2010/0145440 A1 6/2010 Keranen
2010/0280604 A1 11/2010 Zipory et al.
2010/0312333 A1 12/2010 Navia et al.
2010/0318184 A1 12/2010 Spence
2011/0034999 A1 2/2011 Carpentier et al.
2011/0276130 A1 11/2011 Alameddine
2012/0059458 A1 3/2012 Buchbinder et al.
2012/0123529 A1 5/2012 Levi et al.
2012/0283820 A1 11/2012 Tseng et al.
2013/0190865 A1 7/2013 Anderson
2013/0204311 A1 8/2013 Kunis
2014/0074299 A1 3/2014 Endou et al.
2014/0081394 A1 3/2014 Keranen et al.
2014/0163669 A1 6/2014 Ben-Zvi et al.
2014/0172070 A1 6/2014 Seguin
2014/0214157 A1* 7/2014 Bortlein .................. A61F 2/243
623/2.11
2014/0358222 A1 12/2014 Gorman, III et al.
2014/0379074 A1 12/2014 Spence et al.
2015/0025623 A1 1/2015 Granada et al.
2015/0190227 A1 7/2015 Johnson et al.
2015/0230921 A1 8/2015 Chau et al.
2015/0245910 A1 9/2015 Righini et al.
2015/0282931 A1 10/2015 Brunnett et al.
2015/0335428 A1 11/2015 Keranen

(56) References Cited

U.S. PATENT DOCUMENTS

| | | | |
|---|---|---|---|
| 2015/0335430 | A1 | 11/2015 | Loulmet et al. |
| 2015/0374493 | A1 | 12/2015 | Yaron et al. |
| 2016/0015514 | A1 | 1/2016 | Lashinski et al. |
| 2016/0074165 | A1 | 3/2016 | Spence et al. |
| 2016/0095705 | A1 | 4/2016 | Keranen et al. |
| 2016/0143732 | A1 | 5/2016 | Glimsdale |
| 2016/0184095 | A1 | 6/2016 | Spence et al. |
| 2016/0199177 | A1 | 7/2016 | Spence et al. |
| 2016/0256276 | A1 | 9/2016 | Yaron |
| 2016/0346080 | A1 | 12/2016 | Righini et al. |
| 2017/0007399 | A1 | 1/2017 | Keranen |
| 2017/0007402 | A1 | 1/2017 | Zerkowski et al. |
| 2017/0217385 | A1 | 8/2017 | Rinkleff et al. |
| 2017/0266005 | A1 | 9/2017 | McGuckin, Jr. |
| 2017/0273788 | A1 | 9/2017 | O'Carroll et al. |
| 2017/0273789 | A1 | 9/2017 | Yaron et al. |
| 2017/0281337 | A1 | 10/2017 | Campbell |
| 2017/0360426 | A1 | 12/2017 | Hacohen et al. |
| 2018/0000580 | A1 | 1/2018 | Wallace et al. |
| 2018/0085217 | A1 | 3/2018 | Lashinski et al. |
| 2018/0177594 | A1* | 6/2018 | Patel .................... A61F 2/2418 |
| 2018/0206074 | A1 | 7/2018 | Tanasa et al. |
| 2018/0289481 | A1 | 10/2018 | Dolan |
| 2018/0303606 | A1 | 10/2018 | Rothstein et al. |
| 2018/0318073 | A1 | 11/2018 | Tseng et al. |
| 2018/0318080 | A1 | 11/2018 | Quill et al. |
| 2020/0054453 | A1 | 2/2020 | Zerkowski et al. |
| 2020/0360143 | A1 | 11/2020 | O'Carroll et al. |
| 2021/0212826 | A1 | 7/2021 | Zerkowski et al. |
| 2021/0361426 | A1 | 11/2021 | Hacohen |
| 2023/0086853 | A1 | 3/2023 | Zerkowski et al. |

FOREIGN PATENT DOCUMENTS

| | | | |
|---|---|---|---|
| EP | 0338994 | A1 | 10/1989 |
| EP | 0624080 | A1 | 11/1994 |
| EP | 0592410 | B1 | 10/1995 |
| EP | 0850607 | A1 | 7/1998 |
| EP | 1432369 | A1 | 6/2004 |
| EP | 1521550 | A2 | 4/2005 |
| EP | 1296618 | B1 | 1/2008 |
| EP | 1827314 | B1 | 12/2010 |
| EP | 2591754 | A1 | 5/2013 |
| EP | 2620125 | A1 | 7/2013 |
| EP | 2726018 | A2 | 5/2014 |
| EP | 2806829 | A2 | 12/2014 |
| EP | 3395296 | B1 | 12/2019 |
| EP | 2747708 | B1 | 1/2022 |
| WO | 9117720 | A1 | 11/1991 |
| WO | 9719655 | A1 | 6/1997 |
| WO | 9824386 | A1 | 6/1998 |
| WO | 0149213 | A2 | 7/2001 |
| WO | 0154625 | A1 | 8/2001 |
| WO | 0247575 | A2 | 6/2002 |
| WO | 0249546 | A2 | 6/2002 |
| WO | 03028558 | A2 | 4/2003 |
| WO | 2005084595 | A1 | 9/2005 |
| WO | 2005102015 | A2 | 11/2005 |
| WO | 2005107650 | A2 | 11/2005 |
| WO | 2006011127 | A2 | 2/2006 |
| WO | 2006091163 | A1 | 8/2006 |
| WO | 2007067942 | A1 | 6/2007 |
| WO | 2008058940 | A1 | 5/2008 |
| WO | 2009139776 | A1 | 11/2009 |
| WO | 2009155561 | A2 | 12/2009 |
| WO | 2010121076 | A2 | 10/2010 |
| WO | 2012063228 | A1 | 5/2012 |
| WO | 2013110722 | A2 | 8/2013 |
| WO | 2013114214 | A2 | 8/2013 |
| WO | 2015023579 | A1 | 2/2015 |
| WO | 2015023862 | A2 | 2/2015 |
| WO | 2015127264 | A1 | 8/2015 |
| WO | 2015198125 | A1 | 12/2015 |
| WO | 2016038017 | A1 | 3/2016 |
| WO | 2016040881 | A1 | 3/2016 |
| WO | 2016130820 | A1 | 8/2016 |
| WO | 2017103833 | A1 | 6/2017 |

* cited by examiner

APPARATUS AND METHODS FOR REDUCING PARAVALVULAR LEAKAGE

CROSS-REFERENCE TO RELATED APPLICATION

This application is a continuation of PCT patent application no. PCT/US2021/056964, filed Oct. 28, 2021, which claims priority to U.S. Provisional Application No. 63/107,245, filed Oct. 29, 2020, each of these applications being incorporated herein by this specific reference.

FIELD

The present disclosure relates to systems and devices for reducing paravalvular leakage, and in particular to prosthetic valve docking devices that are configured to provide an improved seal between the tissue of a native heart valve and a prosthetic valve.

BACKGROUND

Native heart valves (e.g., the aortic, pulmonary, tricuspid and mitral valves) regulate the flow of blood in the human body by temporarily opening to permit forward flow of blood and then closing to prevent backward flow (or regurgitation) of blood. However, various congenital, inflammatory, infectious, and/or other conditions can cause these native heart valves to malfunction. For example, a defective native heart valve may not fully close when it is supposed to, thereby resulting in some undesirable regurgitation of blood. As another example, calcium deposits can collect around the native heart valve, thereby narrowing the opening of the valve (referred to as "stenosis") and restricting blood-flow through the valve. Such conditions can eventually lead to serious malfunctioning of the heart, requiring repair and/or replacement of the native valve. For many years, doctors attempted to repair and/or replace defective heart valves via open-heart surgery.

However, because of the risks and complications of open-heart surgery, less invasive transcatheter procedures have been developed that access the heart indirectly via a blood vessel. Typically, these transcatheter procedures replace the defective native heart valve with a prosthetic valve that is advanced through a vein or artery to the heart. Thus, instead of opening the entire chest cavity like in open heart surgery, these transcatheter procedures only require a small incision at or near the blood vessel. For example, in one transcatheter technique, a user (e.g., surgeon) may make a small incision in a patient's groin to access the femoral vein or artery and may advance a transcatheter heart valve (THV) on a catheter through the blood vessel until the THV reaches the defective native heart valve. Once at the defective native valve, a THV can then be expanded to its functional size. Prosthetic heart valves can be expanded to their functional size in various ways, including inflatable balloon, self-expanding frames, and/or mechanically expandable frames. Such transcatheter approaches are much less invasive than open heart surgery and can reduce and/or avoid the risks and complications associated with open heart surgery.

However, in some instances, the implantation or deployment site (e.g., a native heart valve annulus) itself may not provide a good seat for the THV. Additionally, or alternatively, in some instances, the shape of the native annulus may differ from the shape of the prosthetic heart valve. As a result, the prosthetic heart valve may not securely anchor to the native tissue and/or there may be paravalvular leakage (PVL) between the prosthetic heart valve and the native tissue.

Accordingly, apparatus and methods for securing a prosthetic heart valve to the native tissue and/or reducing PVL are desirable.

SUMMARY

The present disclosure relates to apparatus and methods for reducing paravalvular leakage. Specifically, the present disclosure is directed to a docking device for prosthetic heart valves that is configured to reduce PVL between the prosthetic heart valve and the native tissue.

In one representative embodiment, a docking device for a prosthetic heart valve comprises an inflow end, an outflow end, a support structure, and an expandable sleeve that covers at least a portion of the support structure. The support structure is disposed between the inflow end and the outflow end of the docking device and comprises an inflow section and an outflow section. The inflow section extends from the inflow end of the docking device toward the outflow end of the docking device and is configured to be positioned on an inflow side of a native heart valve. The outflow section extends between the outflow end of the docking device and the inflow section of the support structure and is configured to be positioned on an outflow side of the native heart valve. The outflow section comprises a first portion, a second portion, and a third portion. The first portion of the outflow section extends distally from the inflow section to the third portion, the third portion extends distally from the first portion to the second portion, and the second portion extends distally from the third portion to the outflow end of the docking device. The expandable sleeve is movable from a compressed position to an expanded position when a crimping pressure is released, and in the expanded position, the expandable sleeve extends at least 100 degrees over the first portion of the outflow section of the support structure.

In another representative embodiment, a docking device for a prosthetic heart valve, comprises an atrial end, a ventricular end, a support structure disposed between the atrial end and the ventricular end, and an expandable sleeve that covers at least a portion of the support structure. The support structure comprises an atrial section and a ventricular section. The atrial section extends from the atrial end of the docking device toward the ventricular end of the docking device and is configured to be positioned on an atrial side of a native mitral valve. The ventricular section extends from the ventricular end of the docking device toward the atrial end of the docking device and is configured to be positioned on a ventricular side of the native mitral valve. Further, the ventricular section comprises a first turn, a second turn, and one or more intermediate turns. The first turn is disposed closer to the atrial section than the second turn, and the one or more intermediate turns are disposed between the first and second turns. Further, the support structure is configured to move from a delivery configuration to a deployed configuration when the support structure is released from a docking device delivery apparatus. In the deployed configuration, the first turn comprises a different geometry than the one or more intermediate turns.

In yet another representative embodiment, a prosthetic heart valve assembly comprises a docking device and a prosthetic heart valve disposed within the docking device. The docking device comprises an atrial end, a ventricular end, a support structure, and an expandable sleeve that covers at least a portion of the support structure. The support structure is disposed between the atrial end and the ventricular end of the docking device and comprises an atrial section and a ventricular section. The atrial section extends from the atrial end of the docking device toward the ventricular end of the docking device and is configured to be positioned on an atrial side of a native mitral valve. The ventricular section extends between the ventricular end of the docking device and the atrial section of the support structure and is configured to be positioned on a ventricular side of the native mitral valve. The ventricular section comprises a first portion, a second portion, and a third portion. The first portion extends distally from the atrial section to the third portion, the third portion extends distally from the first portion to the second portion, and the second portion extends distally from the third portion to the ventricular end of the docking device. The expandable sleeve is movable from a compressed position to an expanded position when a crimping pressure is released, and in the expanded position, the expandable sleeve extends at least 100 degrees over the first portion of the ventricular section of the support structure. The prosthetic heart valve comprises a radially expandable and compressible frame and a plurality of leaflets coupled to the frame. The plurality of leaflets are configured to selectively open to permit blood to flow through the prosthetic heart valve.

In yet another representative embodiment, a prosthetic heart valve assembly comprises a docking device and a prosthetic heart valve disposed within the docking device. The docking device comprises an atrial end, a ventricular end, a support structure, and an expandable sleeve that covers at least a portion of the support structure. The support structure is disposed between the atrial end and the ventricular end of the docking device and comprises an atrial section and a ventricular section. The atrial section extends from the atrial end of the docking device toward the ventricular end of the docking device and is configured to be positioned on an atrial side of a native mitral valve. The ventricular section extends from the ventricular end of the docking device toward the atrial end of the docking device and is configured to be positioned on a ventricular side of the native mitral valve. The ventricular section comprises a first turn, a second turn, and one or more intermediate turns. The first turn is disposed closer to the atrial section than the second turn, and the one or more intermediate turns are disposed between the first and second turns. The support structure is movable from a delivery configuration to a deployed configuration, wherein in the deployed configuration, the first turn comprises a different geometry than the one or more intermediate turns when the first turn and the one or more intermediate turns are released from a docking device delivery apparatus and are deployed at the native mitral valve. The prosthetic heart valve comprises a radially expandable and compressible frame that is configured to be radially expanded to an expanded position from a compressed position within the docking device and a plurality of leaflets coupled to the frame. The plurality of leaflets are configured to selectively open to permit blood to flow through the prosthetic heart valve.

In yet another representative embodiment, a method comprises wrapping at least one complete turn of a coil around an outflow side of two or more leaflets of a native heart valve, the at least one complete turn comprising a first geometry; wrapping a second turn of the coil around the outflow side of the two or more leaflets of the native heart valve, the second turn comprising a second geometry different than the first geometry; and radially expanding an expandable sleeve around at least a portion of the second turn of the coil.

The foregoing and other objects, features, and advantages of the disclosed technology will become more apparent from the following detailed description, which proceeds with reference to the accompanying figures.

DETAILED DESCRIPTION

General Considerations

Figure 1:
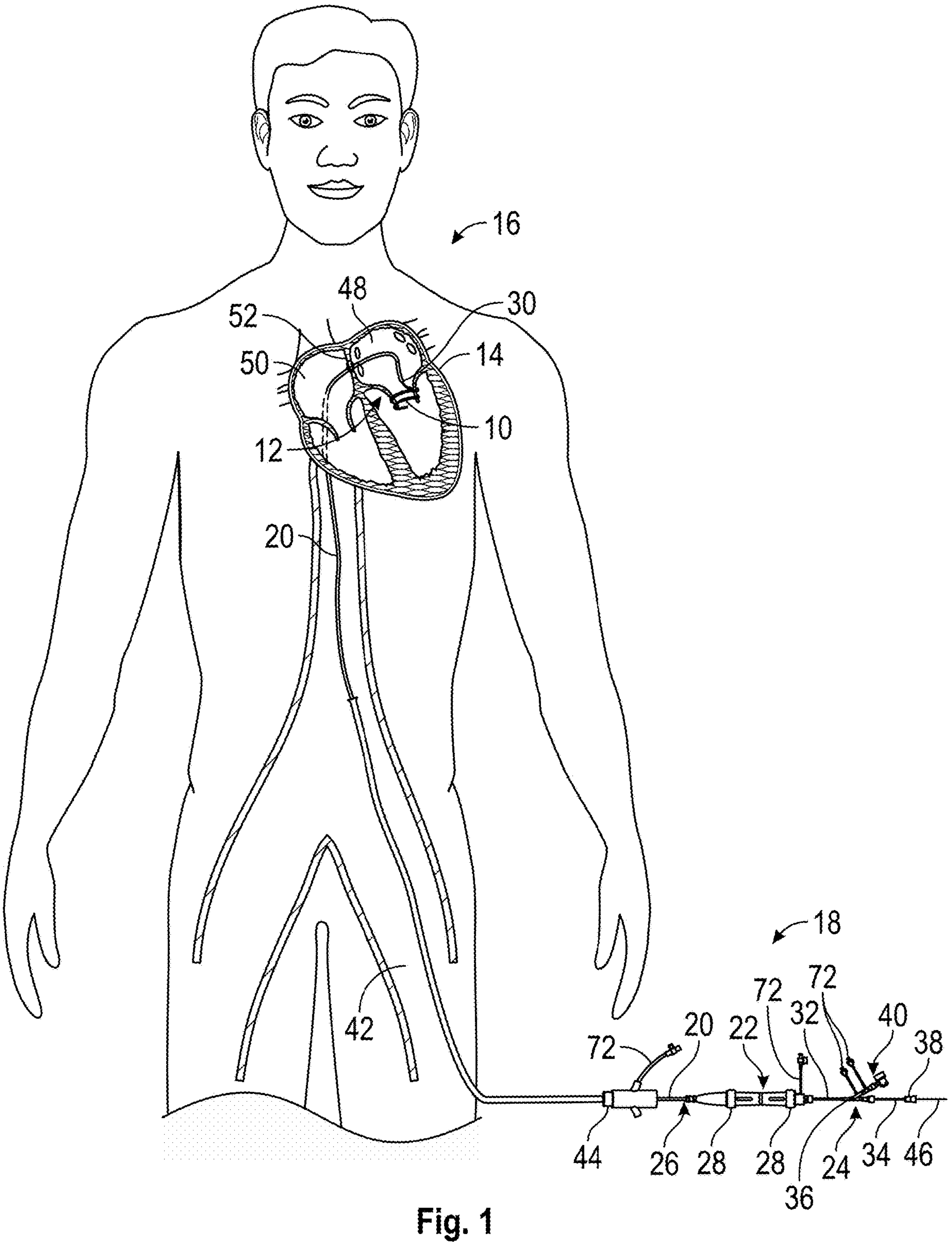
FIG. 1 schematically illustrates a docking device delivery apparatus implanting a docking device for a prosthetic heart valve at a mitral valve of a patient, according to an embodiment.

For purposes of this description, certain aspects, advantages, and novel features of the embodiments of this disclosure are described herein. The described methods, systems, and apparatus should not be construed as limiting in any way. Instead, the present disclosure is directed toward all novel and non-obvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present, or problems be solved.

Features, integers, characteristics, compounds, chemical moieties, or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms “a,” “an,” and “at least one” encompass one or more of the specified element. That is, if two of a particular element are present, one of these elements is also present and thus “an” element is present. The terms “a plurality of” and “plural” mean two or more of the specified element.

As used herein, the term “and/or” used between the last two of a list of elements means any one or more of the listed elements. For example, the phrase “A, B, and/or C” means “A,” “B,” “C,” “A and B,” “A and C,” “B and C,” or “A, B, and C.”

As used herein, the term “coupled” generally means physically coupled or linked and does not exclude the presence of intermediate elements between the coupled items absent specific contrary language.

Directions and other relative references (e.g., inner, outer, upper, lower, etc.) may be used to facilitate discussion of the drawings and principles herein, but are not intended to be limiting. For example, certain terms may be used such as “inside,” “outside,”, “top,” “down,” “interior,” “exterior,” and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an “upper” part can become a “lower” part simply by turning the object over. Nevertheless, it is still the same part and the object remains the same. As used herein, “and/or” means “and” or “or,” as well as “and” and “or.”

In the context of the present application, the terms “lower” and “upper” are used interchangeably with the term’s “inflow” and “outflow”, respectively. Thus, for example, the lower end of the valve is its inflow end and the upper end of the valve is its outflow end.

As used herein, with reference to the prosthetic medical device (e.g., heart valve), capsule, and the delivery apparatus, “proximal” refers to a position, direction, or portion of a component that is closer to the user and/or a handle of the delivery apparatus that is outside the patient, while “distal” refers to a position, direction, or portion of a component that is further away from the user and/or the handle of the delivery apparatus and closer to the implantation site. The terms “longitudinal” and “axial” refer to an axis extending in the proximal and distal directions, unless otherwise expressly defined. Further, the term “radial” refers to a direction that is arranged perpendicular to the axis and points along a radius from a center of an object (where the axis is positioned at the center, such as the longitudinal axis of the prosthetic valve).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

Overview of the Disclosed Technology

Defective native heart valves may be replaced with transcatheter heart valves (THVs). However, in some instances, it may be difficult to secure a prosthetic heart valve to the native tissue (e.g., to the leaflets and/or annulus of the native heart valve) and/or to control PVL at the implantation location.

The present disclosure generally relates to docking devices that can be used, for example, in conjunction with expandable prosthetic valves at a native valve annulus (e.g., mitral, tricuspid, pulmonary, and/or aortic valve annulus) in order to secure the prosthetic valve relative to the native tissue. As another example, the docking devices of the present disclosure can also reduce or eliminate PVL. In particular, the docking devices of the present disclosure may reduce and/or eliminate paravalvular leakage at and/or near the commissures of the native heart valve. In some embodiments, the docking device comprises an expandable sleeve that is configured to provide a seal between the native valve tissue and the prosthetic valve. However, docking devices of the present disclosure comprise expandable sleeves that are configured to extend farther along the outflow side of the docking device than conventional docking devices. As one example, the expandable sleeve may be configured to extend at least 100 degrees from where the docking device is configured to cross over from the inflow side to the outflow side of the valve leaflets (e.g., the posteromedial commissure of a mitral valve). Thus, when implanted at a mitral valve, the expandable sleeve may be configured to extend from the posteromedial commissure to the anterolateral commissure. By extending farther along the outflow side of the leaflets of the native heart valve, the expandable sleeve may help seal commissures and/or other regions of the native valve leaflets that typically contribute to paravalvular leakage.

In some embodiments, the expandable sleeve is configured to be shaped and/or sized to minimize obstructions to the inflow and/or outflow tracts (e.g., the left ventricular outflow tract (LVOT)). For example, a portion of the expandable sleeve that is configured to be positioned/disposed adjacent and/or proximate to the inflow and/or outflow tract may be tapered. As another example, the expandable sleeve may comprise two or more expandable sleeves that are separated from one another by a gap, and the gap may be configured to be positioned/disposed adjacent and/or proximate to the inflow and/or outflow tract. As just one example, when the docking device is implanted at a mitral valve, the expandable sleeve may be tapered and/or nonexistent at the portion of the docking device that is positioned/disposed adjacent and/or proximate to the LVOT to minimize obstruction of blood through the aortic valve. In this way, the expandable sleeve may provide an enhanced seal between the native valve tissue and the prosthetic valve without impeding blood flow through other native heart valves.

In some embodiments, a portion of the docking device that is configured to be positioned most superior and/or closest to a secured edge of the native heart valve on the outflow side of the native heart valve (i.e., the uppermost ventricular side portion of the docking device when the docking device is implanted at a mitral valve) has a different geometry (e.g., shape and/or size) than one or more of the portions of the docking device that are configured to positioned farther away from the annulus of the native heart valve on the outflow side of the native heart valve. In some such embodiments, this uppermost ventricular side portion of the docking device is larger than an adjacent outflow side portion of the docking device. Additionally or alternatively, the uppermost ventricular side portion of the docking device is non-circular, substantially D-shaped, substantially crescent-shaped, and/or otherwise comprises the same or similar shape as the native valve annulus. By conforming more to the size and/or shape of the native valve annulus, the uppermost ventricular side portion of the docking device may hold the prosthetic valve more securely in place (i.e., reduce shifting of the prosthetic valve relative to the native heart valve) and/or otherwise provide an enhanced seal between the native valve tissue and the prosthetic valve.

Additional information and examples are provided below with reference to the accompanying drawings.

Figure 2:
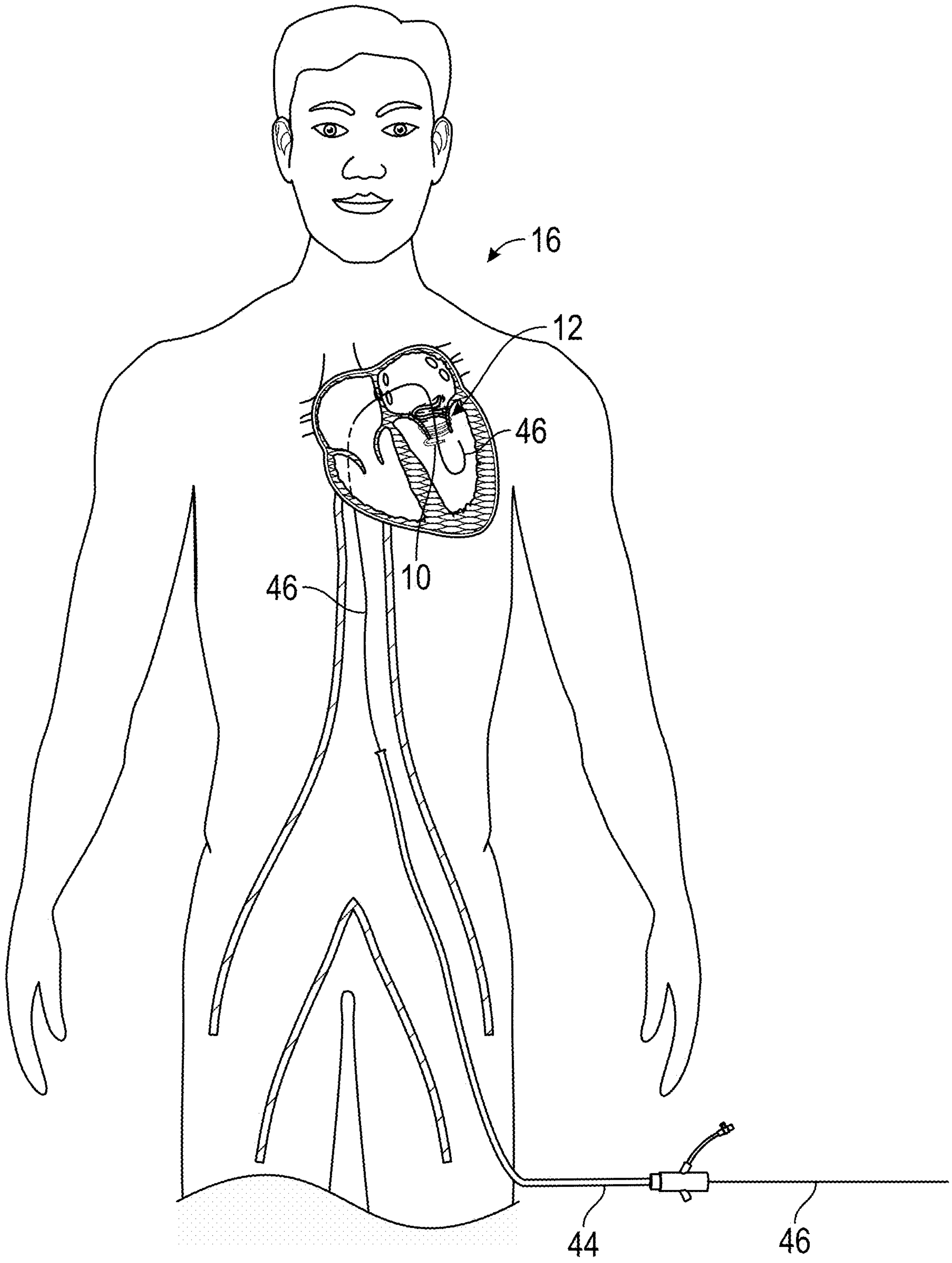
FIG. 2 schematically illustrates the docking device of FIG. 1 fully implanted at the mitral valve of the patient after the docking device delivery apparatus has been removed from the patient.
Figure 3:
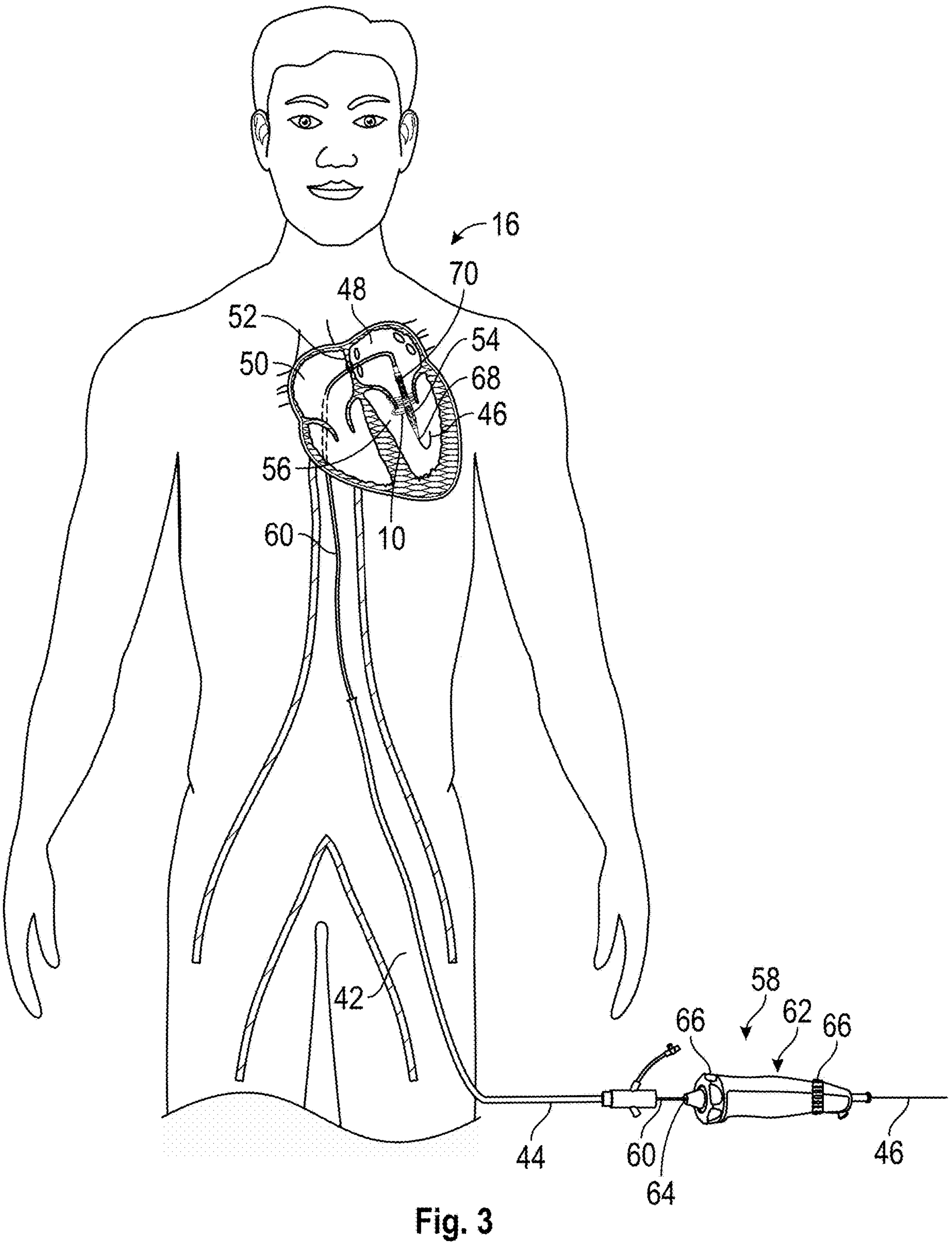
FIG. 3 schematically illustrates a prosthetic heart valve delivery apparatus implanting a prosthetic heart valve in the implanted docking device of FIG. 2 at the mitral valve of the patient, according to an embodiment.

FIGS. 1-3 depict an exemplary transcatheter heart valve replacement procedure which utilizes a docking device, according to one embodiment. During the procedure, a user first delivers and implants the docking device at a patient's native heart valve using a docking device delivery apparatus (FIG. 1), then removes the docking device delivery apparatus from the patient after implanting the docking device (FIG. 2), and finally implants the prosthetic valve within the implanted docking device using a prosthetic valve delivery apparatus (FIG. 3).

FIG. 1 depicts a first stage in an exemplary mitral valve replacement procedure where a docking device 10 is being implanted at a mitral valve 12 of a heart 14 of a patient 16 using a docking device delivery apparatus 18 (which may also be referred to herein as "catheter" and/or "docking device delivery device").

In general, the docking device delivery apparatus 18 comprises a delivery shaft 20, a handle 22, and a pusher assembly 24. The delivery shaft 20 is configured to extend into the patient's vasculature and provide a passageway for the docking device 10 to reach the implantation site (e.g., mitral valve 12). Specifically, the delivery shaft 20 may be configured to be advanced through the patient's vasculature to the implantation site and may be configured to receive and/or retain the docking device 10 therein. In some embodiments, the delivery shaft 20 may comprise an outer sheath or shaft that defines a lumen, and the pusher assembly 24 and/or docking device 10 may be configured to be received and/or advanced within this lumen.

Handle 22 is configured to be gripped and/or otherwise held by the user to advance the delivery shaft 20 through the patient's vasculature. Specifically, the handle 22 is coupled to a proximal end 26 of the delivery shaft 20 and is configured to remain accessible to the user (e.g., outside the patient 16) during the docking device implantation procedure. In this way, the user can advance the delivery shaft 20 through the patient's vasculature by exerting a force on (e.g., pushing) the handle 22. In some embodiments, the delivery shaft 20 may be configured to carry the pusher assembly 24 and/or docking device 10 with it as it advances through the patient's vasculature. In this way, the docking device 10 and/or pusher assembly 24 may advance through the patient's vasculature in lockstep with the delivery shaft 20 as the user grips the handle 22 and pushes the delivery shaft 20 deeper into the patient's vasculature.

In some embodiments, the handle 22 may comprise one or more articulation members 28 that are configured to aid in navigating the delivery shaft 20 through the patient's vasculature. Specifically, the articulation members 28 may comprise one or more of knobs, buttons, wheels, and/or other types of physically adjustable control members that are configured to be adjusted by the user to flex, bend, twist, turn, and/or otherwise articulate a distal end 30 of the delivery shaft 20 to aid in navigating the delivery shaft 20 through the patient's vasculature.

Pusher assembly 24 is configured to deploy and/or implant the docking device 10 at the implantation site (e.g., native valve). Specifically, the pusher assembly 24 is configured to be adjusted by the user to advance the docking device 10 through the delivery shaft 20 and push the docking device 10 out of the distal end 30 of the delivery shaft 20. As described above, the pusher assembly 24 may be configured to extend through the delivery shaft 20, within the lumen defined by the outer sheath of the delivery shaft 20. The pusher assembly 24 also may be coupled to the docking device 10 such that the pusher assembly 24 pushes the docking device 10 through and/or out of the delivery shaft 20 as the pusher assembly 24 advances through the delivery shaft 20. Stated slightly differently, because it is retained by, held, and/or otherwise coupled to the pusher assembly 24, the docking device 10 may advance in lockstep with the pusher assembly 24 through and/or out of the delivery shaft 20.

The pusher assembly 24 comprises a pusher shaft 32 and, in some embodiments, may also include a sleeve shaft 34. The pusher shaft 32 is configured to advance the docking device 10 through the delivery shaft 20 and out of the distal end 30 of the delivery shaft 20, while the sleeve shaft 34, when included, may be configured to deploy an expandable sleeve of the docking device 10. Specifically, the sleeve shaft 34 may be configured to cover the docking device 10 within the delivery shaft 20 while the pusher shaft 32 pushes the docking device 10 out of the delivery shaft 20 and positions the docking device 10 at the implantation site.

In some embodiments, the pusher assembly 24 may comprise a pusher handle 36 (which may also be referred to herein as "hub assembly 36") that is coupled to the pusher shaft 32 and that is configured to be gripped and pushed by the user to translate the pusher shaft 32 axially relative to the delivery shaft 20 (e.g., to push the pusher shaft 32 into and/or out of the distal end 30 of the delivery shaft 20). The sleeve shaft 34 may be configured to be retracted and/or withdrawn from the docking device 10, after positioning the docking device 10 at the implantation site. For example, the pusher assembly 24 may include a sleeve handle 38 that is coupled to the sleeve shaft 34 and is configured to be pulled by a user to retract the sleeve shaft 34 (e.g., axially move) relative to the pusher shaft 32.

The pusher assembly 24 may be removably coupled to the docking device 10 and as such may be configured to release, detach, decouple, and/or otherwise disconnect from the docking device 10 once the docking device 10 has been deployed at the implantation site. As just one example, the pusher assembly 24 (e.g., pusher shaft 32) may be removably coupled to the docking device 10 via a thread, string, yarn, suture, or other suitable material that is tied or sutured to the docking device 10.

In some embodiments, the pusher assembly 24 comprises a suture lock assembly 40 that is configured receive and/or hold the thread or other suitable material that is coupled to the docking device 10 via the suture. Thus, the thread or other suitable material that forms the suture may extend from the docking device 10, through the pusher assembly 24, to the suture lock assembly 40. The suture lock assembly 40 may also be configured to cut the thread to release, detach, decouple, and/or otherwise disconnect the docking device 10 from the pusher assembly 24. For example, the suture lock assembly 40 may comprise a cutting mechanism that is configured to be adjusted by the user to cut the thread.

Further details of the docking device delivery apparatus and its variants are described in International Publication No. WO 2020/247907, which is incorporated by reference herein in its entirety.

Before inserting the docking device delivery apparatus 18 into the vasculature of the patient 16, the user may first make an incision in the patient's body to access a blood vessel 42. For example, in the embodiment illustrated in FIG. 1, the user may make an incision in the patient's groin to access a femoral vein. Thus, in such embodiments, the blood vessel 42 may be a femoral vein.

After making the incision at the blood vessel 42, the user may insert an introducer device 44, a guidewire 46, and/or other devices (e.g., delivery shaft 20, pusher shaft 32, and/or sleeve shaft 34 of the docking device delivery apparatus 18, catheters, and/or other delivery apparatuses, docking device 10, prosthetic valves, etc.) through the incision and into the blood vessel 42. The introducer device 44 (which can include an introducer sheath) is configured to facilitate the percutaneous introduction of the guidewire 46 and/or the other devices (e.g., docking device delivery apparatus 18) into and through the blood vessel 42 and may extend through only a portion of the blood vessel 42 even when it is fully inserted by the user (i.e., it may extend through the blood vessel 42 towards the heart 14, but may stop short of the heart 14). The guidewire 46 on the other hand, is configured to guide the delivery apparatuses (e.g., docking device delivery apparatus 18, prosthetic valve delivery apparatuses, catheters, etc.) and their associated devices (e.g., docking device, prosthetic heart valve, etc.) to the implantation site within the heart 14, and thus may extend all the way through the blood vessel 42 and into a left atrium 48 of the heart 14. Specifically, the user may advance the guidewire 46 through the blood vessel 42 (e.g., through the femoral vein and inferior vena cava) to a right atrium 50 of the heart 14. The user may make a small incision in an atrial septum 52 of the heart 14 to allow the guidewire 46 to pass from the right atrium 50 to the left atrium 48 of the heart 14 and may then advance the guidewire 46 through the incision in the atrial septum 52 into the left atrium 48. Thus, the guidewire 46 may provide a pathway that the docking device delivery apparatus 18 can follow as it advances through the patient's vasculature to ensure that the docking device delivery apparatus 18 does not perforate the walls of the blood vessel 42 and/or other vasculature tissue.

After positioning the guidewire 46 within the left atrium 48, the user may insert the docking device delivery apparatus 18 (e.g., delivery shaft 20) into the patient 16 by advancing the docking device delivery apparatus 18 through the introducer device 44 and over the guidewire 46. The user may then continue to advance the docking device delivery apparatus 18 through the patient's vasculature along the guidewire 46 until the docking device delivery apparatus 18 reaches the left atrium 48, as illustrated in FIG. 1. Specifically, the user may advance the delivery shaft 20 of the docking device delivery apparatus 18 by gripping and exerting a force on (e.g., pushing) the handle 22 of the docking device delivery apparatus 18. While advancing the delivery shaft 20 through the patient's vasculature, the user may adjust the one or more articulation members 28 of the handle 22 to navigate the various turns, corners, constrictions, and/or other obstacles in the patient's vasculature.

Once the delivery shaft 20 reaches the left atrium 48, the user may position the distal end 30 of the delivery shaft 20 at and/or near the posteromedial commissure of the mitral valve 12 using the handle 22 (e.g., the articulation members 28). The user may then push the docking device 10 out of the distal end 30 of the delivery shaft 20 with the pusher assembly 24 to deploy and/or implant the docking device 10 at the mitral valve 12. For example, the user may actuate the pusher handle 36 to axially translate the pusher shaft 32, in a distal direction, relative to the delivery shaft 20, such that the docking device 10 (which can be covered by the sleeve shaft 34) is deployed out of the delivery shaft 20 and moved into a desired position at the implantation site.

In some embodiments, the docking device 10 may be constructed from, formed of, and/or comprise a shape memory material, and as such, may return to its original, pre-formed shape when it exits the delivery shaft 20 and is no longer constrained by the delivery shaft 20. As one example, the docking device 10 may originally be formed as a coil, and thus may wrap around the ventricular side of the leaflets as it exits the delivery shaft 20 and returns to its original coiled configuration. This process is discussed in greater detail below with reference to FIGS. 17-18.

After pushing the ventricular portion of the docking device 10 (i.e., the portion of the docking device 10 that is configured to be positioned/disposed within a left ventricle 56 and/or on the ventricular side of the mitral valve leaflets), the user may then release the remaining portion of the docking device 10 (the atrial portion of the docking device 10) from the delivery shaft 20 within the left atrium 48. Specifically, the user may retract the delivery shaft 20 relative to the docking device 10, away from the posteromedial commissure of the mitral valve 12. In some embodiments, the user may maintain the position of the pusher shaft 32 (e.g., by exerting a holding and/or pushing force on the pusher shaft 32) while retracting the delivery shaft 20 so that the delivery shaft 20 withdraws and/or otherwise retracts relative to the docking device 10 and the pusher shaft 32. In this way, the pusher shaft 32 may hold the docking device 10 in place while the user retracts the delivery shaft 20, thereby releasing the docking device 10 from the delivery shaft 20. In some embodiments, the user may also retract the sleeve shaft 34 from the docking device 10 to uncover the docking device 10, and in some embodiments, deploy an expandable sleeve of the docking device.

After deploying and/or implanting the docking device 10, the user may decouple and/or otherwise disconnect the docking device delivery apparatus 18 from the docking device 10 by, for example, cutting the thread that is sutured to the docking device 10. As just one example, the user may cut the thread with the cutting mechanism of the suture lock assembly 40. Once the docking device 10 is disconnected from the docking device delivery apparatus 18, the user may retract the entire docking device delivery apparatus 18 (the delivery shaft 20, handle 22, and pusher assembly 24) from the patient 16 so that the user can deliver and implant the THV at the mitral valve 12. For example, the docking device 10 and the THV may be delivered on two different, separate delivery apparatuses, and thus the user may need to remove the docking device delivery apparatus 18 from the patient 16 to make room for the THV delivery apparatus. As another example, the user may need to remove the docking device delivery apparatus 18 from the patient 16 to load the THV onto the delivery apparatus. In either example, the user may need to remove the docking device delivery apparatus 18 from the patient 16 before implanting the THV.

FIG. 2 depicts this second stage in the mitral valve replacement procedure, where the docking device 10 has been fully deployed and implanted at the mitral valve 12 and the docking device delivery apparatus 18 (including the delivery shaft 20) has been removed from the patient 16 such that only the guidewire 46 and the introducer device 44 remain inside the patient 16. The introducer device 44 may remain inside the patient 16 to help percutaneously insert the THV and the valve delivery apparatus into the patient 16, while the guidewire 46 may remain within the patient's vasculature to help advance the THV and the valve delivery apparatus through the patient's vasculature. Specifically, the guidewire 46 may ensure that the THV and the valve delivery apparatus do not perforate the walls of the blood vessel 42 and/or other vasculature tissue as they advance through the patient's vasculature. In some embodiments, the user may advance the guidewire 46 through the mitral valve 12 and into the left ventricle 56 to ensure that the guidewire 46 routes the THV and the valve delivery apparatus all of the way to the mitral valve 12 and into the docking device 10.

As illustrated in FIG. 2, the docking device 10 may be configured to wrap around the ventricular side of the leaflets of the mitral valve 12 and squeeze the leaflets radially inward (i.e., radially compress the leaflets) to adjust the size and/or shape of the opening between the two leaflets of the mitral valve 12. For example, the docking device 10 may be configured to reduce the size of the opening of the mitral valve 12 and/or to change the shape of the opening to more closely match the cross-sectional shape and/or profile of the THV (e.g., make the opening more circular for a cylindrical THV). By constricting the mitral valve 12 in this manner, the docking device 10 may provide a tighter fit, and thus a better seal, between the THV and the mitral valve 12.

FIG. 3 depicts a third stage in the mitral valve replacement procedure where the user is delivering and/or implanting a prosthetic heart valve 54 (which may also be referred to herein as "heart valve," "transcatheter heart valve" or "THV" for short, "replacement heart valve," and/or "prosthetic mitral valve") within the docking device 10 and/or at the mitral valve 12 using a prosthetic heart valve delivery apparatus 58. Thus, the docking device 10 and prosthetic heart valve 54 may be delivered on different delivery apparatuses at different stages in the mitral valve replacement procedure. Specifically, the docking device 10 may be delivered to the mitral valve 12 with the docking device delivery apparatus 18 during the first stage of the mitral valve replacement procedure and the prosthetic heart valve 54 may then be delivered with the prosthetic heart valve delivery apparatus 58.

The prosthetic heart valve delivery apparatus 58 comprises a delivery shaft 60 and a handle 62 coupled to a proximal end 64 of the delivery shaft 60. The delivery shaft 60 is configured to extend into the patient's vasculature to deliver, implant, expand, and/or otherwise deploy the prosthetic heart valve 54 within the docking device 10 at the mitral valve 12. The handle 62 may be the same as, or similar to, handle 22 of the docking device delivery apparatus 18 and is similarly configured to be gripped and/or otherwise held by the user to advance the delivery shaft 60 through the patient's vasculature.

In some embodiments, handle 62 may comprise one or more articulation members 66 that are configured to aid in navigating the delivery shaft 60 through the patient's vasculature. Specifically, the articulation members 66 may comprise one or more of knobs, buttons, wheels, and/or other types of physically adjustable control members that are configured to be adjusted by the user to flex, bend, twist, turn, and/or otherwise articulate a distal end 68 of the delivery shaft 60 to aid in navigating the delivery shaft 60 through the patient's vasculature.

In some embodiments, the prosthetic heart valve delivery apparatus 58 may comprise an expansion mechanism 70 that is configured to radially expand and deploy the prosthetic heart valve 54. For example, the expansion mechanism 70 may comprise an inflatable balloon that is configured to be inflated to radially expand the prosthetic heart valve 54 within the docking device 10. The expansion mechanism 70 may be included in and/or coupled to the delivery shaft 60 at and/or proximate to the distal end 68 of the delivery shaft 60. In other embodiments, the prosthetic heart valve 54 may be self-expanding and may be configured to radially expand on its own without the expansion mechanism 70. In other embodiments, the prosthetic heart valve 54 may be mechanically expandable and the prosthetic heart valve delivery apparatus 58 can include one or more mechanical actuators configured to radially expand the prosthetic heart valve 54.

Prosthetic heart valve 54 may be coupled to the delivery shaft 60 at and/or proximate to the distal end 68 of the delivery shaft 60. In embodiments where prosthetic heart valve delivery apparatus 58 includes the expansion mechanism 70, prosthetic heart valve 54 may be mounted on the expansion mechanism 70 in a radially compressed configuration. In some embodiments, prosthetic heart valve 54 may be removably coupled to the delivery shaft 60 such that, after the prosthetic heart valve 54 is radially expanded and deployed from the prosthetic heart valve delivery apparatus 58, the prosthetic heart valve delivery apparatus 58 can be retracted away from the implanted prosthetic heart valve 54 and removed from the patient 16.

Prosthetic heart valve 54 is configured to be received and/or retained within the docking device 10. That is, docking device 10 is configured to receive the prosthetic heart valve 54 and help anchor the prosthetic heart valve 54 to the mitral valve 12. As will be explained in further detail below, docking device 10 is also configured to provide a seal between the prosthetic heart valve 54 and the leaflets of the mitral valve to reduce paravalvular leakage around the prosthetic heart valve 54. Specifically, as introduced above, the docking device 10 may initially constrict the leaflets of the mitral valve 12. The prosthetic heart valve 54 may then push the leaflets against the docking device 10 as it radially expands within the docking device 10 (e.g., via inflation of the expansion mechanism 70). Thus, the docking device 10 and the prosthetic heart valve 54 may be configured to sandwich the leaflets of the mitral valve 12 when the prosthetic heart valve 54 is expanded within the docking device 10. In this way, the docking device 10 may provide a seal between the leaflets of the mitral valve 12 and the prosthetic heart valve 54.

As will be explained in greater detail below, the docking device 10 may comprise an expandable sleeve and/or coil structure that extends at least in part around the outflow side of the native valve to provide a seal between the mitral valve 12 and the prosthetic heart valve 54 (thereby reducing paravalvular leakage around the prosthetic heart valve 54). The expandable sleeve may extend farther along the outflow side of the native valve (towards the distal end of the coil) than conventional sleeves. For example, the expandable sleeve may extend at least 100 degrees around the outflow side of the native valve. As another example, the expandable sleeve may be configured to extend around the outflow side of the native valve to an anterolateral commissure of the mitral valve 12 to reduce paravalvular leakage at the anterolateral commissure.

Additionally or alternatively, a portion of the coil structure that is configured to be the most superior portion of the coil on the ventricular side of the mitral valve 12 when the docking device is implanted at the mitral valve 12, may be shaped and/or sized to extend farther towards the anterolateral and/or posteromedial commissures of the mitral valve 12 than the other portions of the coil on the ventricular side of the mitral valve 12. Adjusting the shape and/or size of this uppermost ventricular side portion of the docking device 10 in this manner (i.e., to more closely match the shape and/or size of the mitral valve annulus) may help seal openings in the mitral valve 12 near the commissures of the mitral valve 12 and thus may reduce paravalvular leakage at and/or near these commissures. More generally, the uppermost ventricular side portion of the docking device 10 may help close and/or otherwise seal openings in the mitral valve 12 that are present beyond the edges of the prosthetic heart valve 54 (i.e., radially outwardly from the prosthetic heart valve 54).

In some embodiments, one or more of the docking device delivery apparatus 18, the prosthetic heart valve delivery apparatus 58, and/or the introducer device 44 may comprise one or more flushing ports 72 (FIG. 1) that are configured to supply flushing fluid to the lumens thereof (e.g., lumens of the delivery shaft 20 of docking device delivery apparatus 18, the delivery shaft 60 of the prosthetic heart valve delivery apparatus 58, and/or the introducer device 44) to prevent and/or reduce the likelihood of blood clot (e.g., thrombus) formation.

Like when delivering the docking device 10, the user may insert the prosthetic heart valve delivery apparatus 58 (e.g., delivery shaft 60) into the patient 16 by advancing the prosthetic heart valve delivery apparatus 58 through the introducer device 44 and over the guidewire 46. The user may continue to advance the prosthetic heart valve delivery apparatus 58 along the guidewire 46 (through the patient's vasculature) until the prosthetic heart valve delivery apparatus 58 reaches the mitral valve 12, as illustrated in FIG. 3. Specifically, the user may advance the delivery shaft 60 of the prosthetic heart valve delivery apparatus 58 by gripping and exerting a force on (e.g., pushing) the handle 62 of the prosthetic heart valve delivery apparatus 58. While advancing the delivery shaft 60 through the patient's vasculature, the user may adjust the one or more articulation members 66 of the handle 62 to navigate the various turns, corners, constrictions, and/or other obstacles in the patient's vasculature.

The user may advance the delivery shaft 60 along the guidewire 46 until the prosthetic heart valve 54 and/or expansion mechanism 70 is/are positioned/disposed within the docking device 10 and/or the mitral valve 12. For example, the user may advance the delivery shaft 60 along the guidewire 46 until the delivery shaft 60 extends through the mitral valve 12, such that the distal end 68 of the delivery shaft 60 is positioned/disposed within the left ventricle 56. Once the prosthetic heart valve 54 is appropriately positioned/disposed within the docking device 10, the user may radially expand the prosthetic heart valve 54, such as with the expansion mechanism 70, to its fully expanded position or configuration. In some examples, the user may lock the prosthetic heart valve 54 in its fully expanded position (e.g., with a locking mechanism) to prevent the valve from collapsing. After expanding and deploying the prosthetic heart valve 54, the user may decouple and/or otherwise disconnect the delivery shaft 60 from the prosthetic heart valve 54 and remove the delivery shaft 60 from the patient.

Although FIGS. 1-3 specifically depict a mitral valve replacement procedure, it should be appreciated that the same and/or similar procedure may be utilized to replace other heart valves (e.g., tricuspid, pulmonary, and/or aortic valves). Further, the same and/or similar delivery apparatuses (e.g., docking device delivery apparatus 18, prosthetic heart valve delivery apparatus 58, introducer device 44, and/or guidewire 46), docking devices (e.g., docking device 10), replacement heart valves (e.g., prosthetic heart valve 54), and/or components thereof may be utilized for replacing these other heart valves.

For example, when replacing a native tricuspid valve, the user may also access the right atrium 50 via a femoral vein but may not need to cross the atrial septum 52 into the left atrium 48. Instead, the user may leave the guidewire 46 in the right atrium 50 and perform the same and/or similar docking device implantation process at the tricuspid valve. Specifically, the user may push the docking device 10 out of the delivery shaft 20 around the ventricular side of the tricuspid valve leaflets, release the remaining portion of the docking device 10 from the delivery shaft 20 within the right atrium 50, and then remove the delivery shaft 20 of the docking device delivery apparatus 18 from the patient 16. The user may then advance the guidewire 46 through the tricuspid valve into the right ventricle and perform the same and/or similar prosthetic heart valve implantation process at the tricuspid valve, within the docking device 10. Specifically, the user may advance the delivery shaft 60 of the prosthetic heart valve delivery apparatus 58 through the patient's vasculature along the guidewire 46 until the prosthetic heart valve 54 is positioned/disposed within the docking device 10 and the tricuspid valve. The user may then expand the prosthetic heart valve 54 within the docking device 10 before removing the prosthetic heart valve delivery apparatus 58 from the patient 16. In another example, the user may perform the same and/or similar process to replace the aortic valve but may access the aortic valve from the outflow side of the aortic valve via a femoral artery.

Further, although FIGS. 1-3 depict a mitral valve replacement procedure that accesses the mitral valve 12 from the left atrium 48 via the right atrium 50 and femoral vein, it should be appreciated that the mitral valve 12 may alternatively be accessed from the left ventricle 56. For example, the user may access the mitral valve 12 from the left ventricle 56 via the aortic valve by advancing one or more delivery apparatuses through an artery to the aortic valve, and then through the aortic valve into the left ventricle 56.

Exemplary Embodiments of the Disclosed Technology

FIG. 4-13 depict various exemplary docking devices that are configured to receive, retain, and/or anchor a prosthetic heart valve and provide a seal between the prosthetic heart valve and native tissue. Specifically, FIGS. 4-9 depict various exemplary expandable sleeves that may cover the coil of the exemplary docking devices to provide an enhanced seal between the native valve leaflets and the prosthetic heart valve. Specifically, the exemplary expandable sleeves may extend at least 100 degrees along the outflow side of the native valve to reduce paravalvular leakage (PVL) around the prosthetic heart valve. In this manner, the expandable sleeves disclosed herein may also be referred to as "PVL guards." FIGS. 10-13 depict alternative geometries (sizes and/or shapes) for the coil of the docking device that may also provide an enhanced seal between the native tissue and the prosthetic heart valve.

FIGS. 4-13 depict the exemplary docking devices in a deployed configuration. The exemplary docking devices are configured to move to this deployed configuration from a delivery configuration when they deployed from a docking device delivery apparatus (e.g., docking device delivery apparatus 18 described above). However, as will be explained in greater detail below, the exemplary docking devices are configured to move from the deployed configuration to an assembled configuration when a prosthetic heart valve is expanded within the docking devices. FIGS. 20-21 and 24-25 depict an exemplary docking device in this final assembled configuration.

Figure 4:
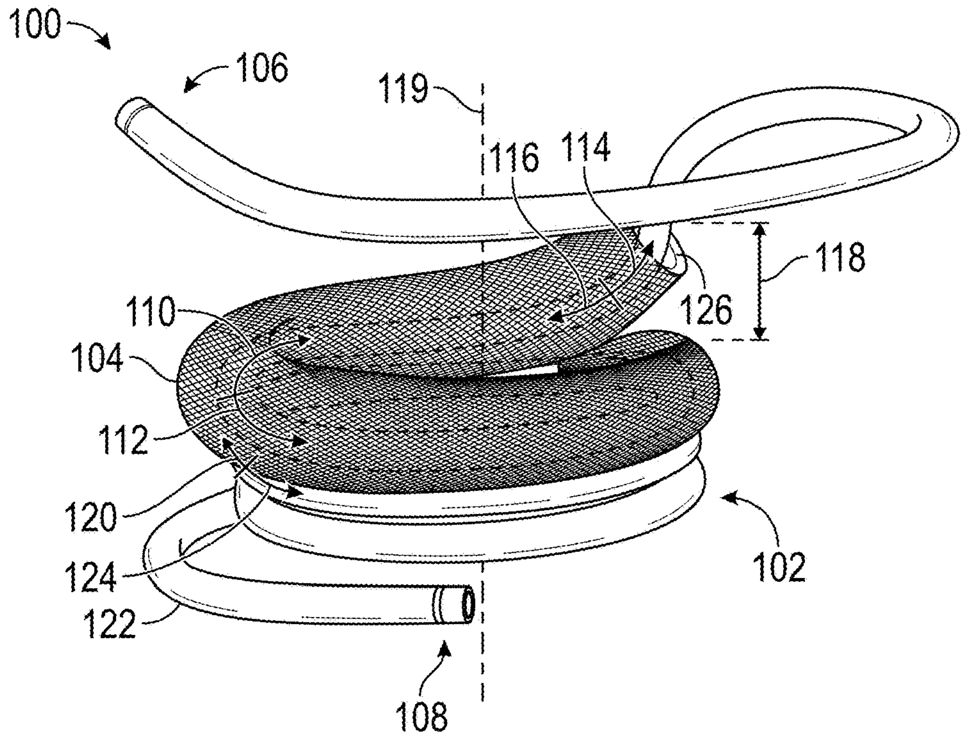
FIG. 4 illustrates a perspective view of a docking device, according to an embodiment.
Figure 5:
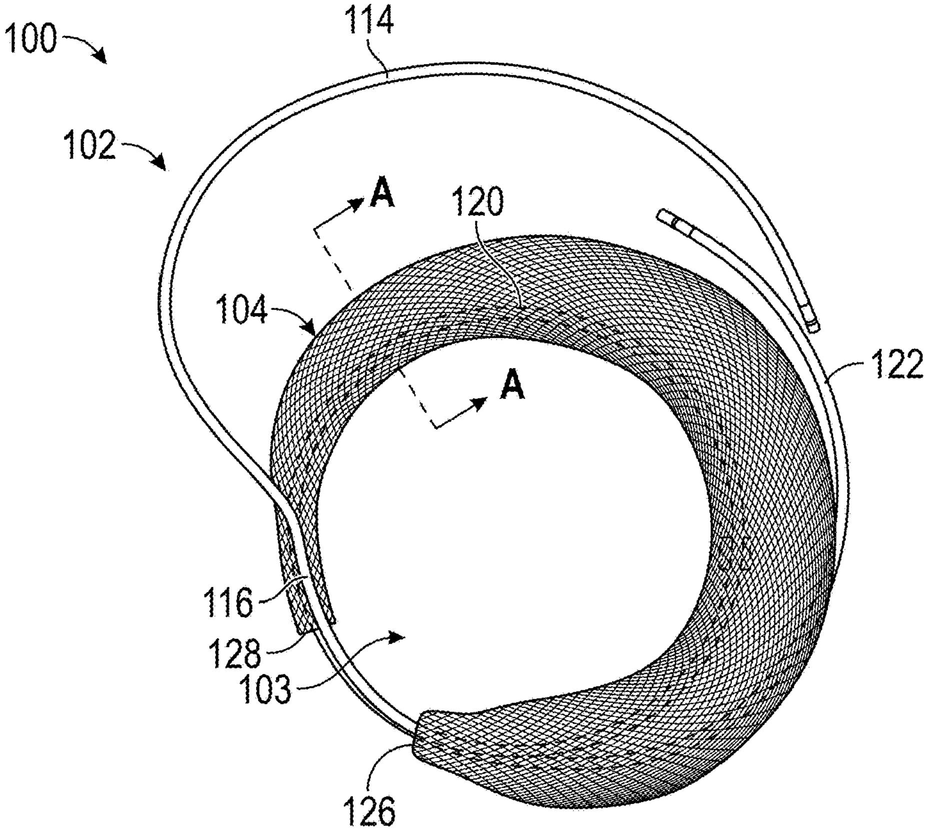
FIG. 5 illustrates a top view of the docking device of FIG. 4.

FIGS. 4-5 depict a docking device 100, according to one embodiment. Specifically, FIG. 4 depicts a side perspective view of the docking device 100, and FIG. 5 depicts a top view of the docking device 100. Docking device 100 comprises a coil 102 (which may also be referred to herein as "support structure 102") comprising a plurality of turns and/or windings and defining a lumen 103, and an expandable sleeve 104 (which may also be referred to herein as "expandable guard 104" and/or "PVL guard 104"). The expandable sleeve 104 is configured to extend farther along an outflow side of the native heart valve (and thus cover more of an outflow side of the coil 102) than conventional expandable sleeves to provide an enhanced seal between the native heart valve tissue and a prosthetic heart valve. In this way, expandable sleeve 104 may reduce and/or eliminate PVL around the prosthetic heart valve.

Docking device 100 also has a first end 106 and a second end 108 that is opposite the first end 106. Since second end 108 is configured to exit a delivery shaft (e.g., delivery shaft 20 described above) of a docking device delivery apparatus (e.g., docking device delivery apparatus 18 described above) before the first end 106, and/or extend farther away from the delivery shaft than the first end 106, the second end 108 of the docking device 100 may also be referred to herein as "distal end 108" and the first end 106 may also be referred to herein as "proximal end 106."

Coil 102 extends from the first end 106 to the second end 108, and thus may form and/or otherwise define the first end 106 and the second end 108. The coil 102 comprises a first section 110 and a second section 112, where the first section 110 extends distally from the first end 106 to the second section 112 and the second section 112 extends proximally from the second end 108 to the first section 110. In some embodiments, the first section 110 may be configured to extend distally from the first end 106 and terminate where the docking device 100 crosses sides of the native heart valve. Second section 112 may be configured to begin where the first section 110 terminates (e.g., where the docking device 100 crosses sides of the native heart valve) and may extend distally from the first section 110 to the second end 108. Thus, the first section 110 and the second section 112 may be conjoined where the docking device 100 crosses sides of the native heart valve.

As one example, the first section 110 may be configured to be included on and/or positioned/disposed at an inflow side of a native heart valve (e.g., on the inflow side of the leaflets of the native heart valve) and the second section 112 may be configured to be included on and/or positioned/disposed at an outflow side of the native heart valve (e.g., on the outflow side of the leaflets of the native heart valve) when the docking device 100 is implanted at the native heart valve. For example, the first section 110 may end and the second section 112 may begin where the docking device 100 crosses over from the inflow side of the native heart valve leaflets to the outflow side of the native heart valve leaflets (such as at a commissure of the native heart valve). As such, the first section 110 may also be referred to herein as "inflow section 110" and the second section 112 may also be referred to herein as "outflow section 112." Accordingly, the first end 106 of the docking device 10 may also be referred to herein as "inflow end 106" and the second end 108 may also be referred to herein as "outflow end 108."

As another example, the first section 110 may be configured to be included on and/or positioned/disposed at an atrial side of a native heart valve (e.g., on the atrial side of the leaflets of the native heart valve within the atrium) and the second section 112 may be configured to be included on and/or positioned/disposed at a ventricular side of the native heart valve (e.g., on the ventricular side of the leaflets of the native heart valve within the ventricle), such as when the docking device is implanted at a tricuspid and/or mitral valve. Specifically, the first section 110 may end and the second section 112 may begin where the docking device 100 crosses over from the atrial side of the native heart valve leaflets to the ventricular side of the native heart valve leaflets (such as at a commissure of the native heart valve). As such, the first section 110 may also be referred to herein as "atrial section 110" since the first section 110 may be positioned/disposed within the atrium and the second section 112 may also be referred to herein as "ventricular section 112" since the second section 112 may be positioned/disposed within the ventricle. Further, the first end 106 of the docking device 10 may also be referred to herein as "atrial end 106" and the second end 108 may also be referred to herein as "ventricular end 108."

In one specific example where the docking device 100 is included at a native mitral valve (which will be described in greater detail below), the junction of the first section 110 and the second section 112 (where the first section 110 and the second section 112 meet) may be configured to be positioned/disposed where the coil 102 crosses over between the atrial/inflow and ventricular/outflow sides of the mitral valve leaflets, such as at and/or near an A3/P3 position and/or posteromedial commissure of the native mitral valve.

First section 110 may comprise a first portion 114 (also referred to herein as "first turn 114") and a second portion 116 (also referred to herein as "second turn 116" and/or "atrial side functional turn 116"). When included, first portion 114 extends distally from the first end 106 of the docking device 100 to the second portion 116 and the second portion 116 extends distally from the first portion 114 to the second section 112 of the coil 102. Thus, the first section 110 may define and/or form the first end 106 of the docking device 100. First portion 114 may flare and/or extend radially outwardly from the second portion 116 and may be configured to stabilize the docking device 100 at the native heart valve. Thus, the first portion 114 may also be referred to herein as "flange 114," and/or "stabilization turn 114." In some embodiments, the first portion 114 may be configured to extend parallel to the plane of the annulus of the native heart valve and, in some such embodiments, may be configured to extend beyond the annulus to the lateral shelf and/or other atrial tissue of the native heart valve. By extending radially outwardly towards, to, and/or beyond the shelf of the native heart valve in the plane of the annulus, the first portion 114 may be configured to hold itself substantially parallel to the native heart valve annulus, and in doing so, may help anchor the docking device 100 to the native tissue.

In some embodiments, the first portion 114 may extend axially/longitudinally away from the second portion 116. In some such embodiment, the first portion 114 may be axially separated from the rest of the coil 102 by a greater amount than the other turns of the coil 102 are axially separated from one another. Thus, the first portion 114 may be axially separated from the rest of the coil 102 by a gap 118 that is larger than any axial gaps that may exist between the other turns of the coil 102.

In some embodiments, the first portion 114 may be configured to be removably coupled to a docking device delivery apparatus (e.g., docking device delivery apparatus 18 described above) by, for example, a suture. In some such embodiments, a thread or other suitable material may be sutured to the first portion 114 at and/or proximate to the first end 106 of the coil 102, and a user may cut the thread to decouple and/or otherwise disconnect the docking device 100 from the docking device delivery apparatus.

In some embodiments, the first portion 114 may be configured to be sutured to the native heart valve and/or other surrounding vasculature tissue. For example, the user may suture the first end 106 of the coil 102 to the native heart valve and/or other surrounding vasculature tissue after deploying the docking device 100 at the native heart valve.

Second portion 116 of first section 110 may deflect radially inwardly from the first portion 114 and extends from the first portion 114 to the second section 112. In some embodiments, the second portion 116 may comprise a substantially circular turn when viewed from above at the first end 106 of the coil 102 in a plane perpendicular to a longitudinal axis 119 of the lumen 103 (such as in FIG. 5). However, in other embodiments, the second portion 116 may comprise other non-circular curved profiles.

Second section 112 comprises a first portion 120 (also referred to herein as "first turn 120," "uppermost ventricular side portion 120," "uppermost ventricular side turn 120," "proximal ventricular side turn 120," and/or "proximal ventricular side portion 120"), a second portion 122 (also referred to herein as "second turn 122"), and a third portion 124 (also referred to herein as "one or more intermediate turns 124" and/or "one or more ventricular side functional turns 124") disposed between the first portion 120 and the second portion 122. Thus, first portion 120 extends distally from the first section 110 of the coil 102 to the third portion 124 of the second section 112, third portion 124 extends distally from the first portion 120 to the second portion 122, and the second portion 122 extends distally from the third portion 124 to the second end 108 of the docking device 100. Thus, the third portion 124 may form and/or otherwise define the second end 108 of the docking device 100. Because the first portion 120 extends directly from the first section 110 of the coil 102, it may be the most proximal portion of the second section 112, and therefore may be configured to be positioned closer to the annulus and/or commissures of the native heart valve than the other portions of the second section 112. Further, in examples, when the coil 102 is implanted at the tricuspid or mitral valves, the first portion 120 may be the uppermost portion of the second section 112 on the ventricular side of the native valve (i.e., the first portion 120 may be at a more superior position in the ventricle than the other portions of the second section 112).

In the embodiments of FIGS. 4-5, the first portion 120 and third portion 124 may comprise substantially the same shape when viewed from above (looking down at the first end 106) or below (looking up at the second end 108) the docking device 100 in a plane perpendicular to the longitudinal axis 119. Additionally or alternatively, the first portion 120 and third portion 124 may be substantially the same size. In some such embodiments, the first portion 120 and third portion 124 may comprise circular turns and/or may have substantially the same radius (and thus may define circular planes that have substantially the same surface area) when viewed from above (looking down at the first end 106) or below (looking up at the second end 108) the docking device 100 in a plane perpendicular to the longitudinal axis 119. Thus, the first portion 120 and third portion 124 may be substantially congruent such that they coincide with one another when superimposed and viewed from above or below in a plane perpendicular to the longitudinal axis 119. Stated slightly differently, the first portion 120 and third portion 124 may comprise substantially the same geometry (i.e., same size and shape) when viewed from above or below. That said, third portion 124 may be longer than first portion 120. For example, the first portion 120 may comprise no more than one complete turn (i.e., a 360-degree turn), whereas the third portion 124 may comprise at least one complete turn, and in some examples, two or more complete turns. Thus, in some embodiments, the third portion 124 may be at least 1.1, at least 1.2, at least 1.4, at least 1.6, at least 1.8, at least 2, at least 2.5, at least 3, at most 10, at most 8, and 6, and/or at most 4 times the length of the first portion 120.

Although FIGS. 4-5 depict the first portion 120 and third portion 124 as having the same circular cross sections, it should be appreciated that in other embodiments, the first portion 120 and third portion 124 may comprise different geometries (e.g., different sizes, non-circular shapes, etc.). As one example, the first portion 120 may comprise one or more of elliptical, crescent, D, and/or other irregularly curved shapes when viewed in a plane perpendicular to the longitudinal axis 119. Additionally or alternatively, the first portion 120 may comprise a different geometry than the third portion 124 (i.e., the first portion 120 may be shaped and/or sized differently than the third portion 124). For example, FIGS. 10-13 depict alternative geometries for the first portion where the first portion is shaped and/or sized differently than the third portion.

Second portion 122 may extend and/or flare radially outwardly from the third portion 124 and/or the first portion 120. In some embodiments, second portion 122 extends and/or flares radially outwardly from the third portion 124 and the first portion 120, but not as far as the first portion 114 of the first section 110. However, in other embodiments, the second portion 122 may extend and/or flare radially outwardly beyond the first portion 114 of the first section 110.

In some embodiments, the pitch (distance between the center of adjacent turns of the coil 102) and/or the coil/pitch angle (the angle defined between a turn of the coil 102 and a plane orthogonal to the longitudinal axis 119) of the coil 102 may be substantially consistent/uniform throughout at least two portions of the second section 112 of the coil 102 and/or the second portion 116 of the first section 110. That is, the pitch of two or more of the first portion 120, second portion 122, third portion 124, and/or second portion 116 may be substantially the same. In this way, the axial distance between adjacent turns of the second section 112 of the coil 102 and/or the second portion 116 of the first section 110 may be substantially the same and/or the turns of two or more of the first portion 120, second portion 122, third portion 124 and/or second portion 116 may be substantially parallel to one another. In some such embodiments, the pitch and/or coil angle of the coil 102 may be substantially consistent/uniform throughout the entire second section 112 and the second portion 116 of the first section 110.

In other embodiments, the pitch and/or coil angle of the first portion 120 of the second section 112 may be different than the other portions of the second section 112. As one example, the first portion 120 of the second section 112 may be substantially bowl-shaped when viewed from the side of the coil 102 (in a plane parallel to the longitudinal axis 119) and may extend axially farther towards the first portion 114 of the first section 110 than the other portions of the second section 112. In this way, the first portion 120 may be configured to extend upwards towards the valve annulus, the atrium, and/or the commissures when positioned on the ventricular side of a native mitral valve.

Regarding the relative lengths of the various portions of the coil 102, the first portion 114 of the first section 110 may extend at least 90 degrees, at least 110 degrees, at least 130 degrees, at least 150 degrees, at least 160 degrees, at least 170 degrees, at least 180 degrees, at least 190 degrees, at least 200 degrees, at least 210 degrees, at least 220 degrees, at most 360 degrees, at most 330 degrees, at most 300 degrees, at most 270 degrees, at most 240 degrees, at most 210 degrees, and/or at most 180 degrees. Second portion 116 of the first section 110 may extend at least 50 degrees, at least 70 degrees, at least 90 degrees, at least 110 degrees, at least 130 degrees, at least 150 degrees, at least 170 degrees, at least 180 degrees, at least 190 degrees, at least 200 degrees, at most 270 degrees, at most 250 degrees, at most 230 degrees, at most 210 degrees, at most 190 degrees, and/or at most 180 degrees. First portion 120 of second section 112 may extend at least 180 degrees, at least 220 degrees, at least 260 degrees, at least 300 degrees, at least 320 degrees, at least 340 degrees, at least 360 degrees, at least 380 degrees, at least 400 degrees, at least 420 degrees, at most 540 degrees, at most 500 degrees, at most 460 degrees, at most 420 degrees, at most 380 degrees, at most 360 degrees, at most 340 degrees, and/or at most 320 degrees. Second portion 122 of second section 112 may extend at least 50 degrees, at least 70 degrees, at least 90 degrees, at least 100 degrees, at least 110 degrees, at least 120 degrees, at least 130 degrees, at least 140 degrees, at least 150 degrees, at least 160 degrees, at most 270 degrees, at most 240 degrees, at most 210 degrees, at most 180 degrees, at most 170 degrees, at most 160 degrees, at most 150 degrees, at most 140 degrees, at most 130 degrees, at most 120 degrees, at most 110 degrees, at most 110 degrees, and/or at most 90 degrees. Third portion 124 of second section 112 may extend at least 360 degrees (one complete turn), at least 405 degrees, at least 450 degrees, at least 495 degrees, at least 540 degrees, at least 585 degrees, at least 630 degrees, at least 675 degrees, at least 720 degrees (two complete turns), at most 1,440 degrees, at most 1,260 degrees, at most 1080 degrees, at most 900 degrees, at most 720 degrees, and/or at most 540 degrees.

In some embodiments, the junction of the second portion 116 of the first section 110 of the coil 102 and the first portion 120 of the second section 112 is configured to be disposed/positioned at or proximate to a posteromedial commissure of the mitral valve, posteromedial side of an opening of the mitral valve, and/or an A3/P3 position on the mitral valve. For example, the junction of the second portion 116 of the first section 110 of the coil 102 and the first portion 120 of the second section 112 may be configured to be disposed/positioned no more than 80 degrees, no more than 70 degrees, no more than 60 degrees, no more than 50 degrees, no more than 40 degrees, no more than 30 degrees, no more than 20 degrees, no more than 10 degrees, no more than 5 degrees, no more than 3 degrees, no more than 2 degrees, and/or no more than 1 degree from the posteromedial commissure, the posteromedial side of the opening of the mitral valve, and/or the A3/P3 position on the mitral valve.

In some embodiments, coil 102 may be deformable and may be configured to be unwound to fit inside a delivery shaft (e.g., delivery shaft 20 described above) of a delivery apparatus (e.g., docking device delivery apparatus 18 described above), such as in a substantially straight line. However, unwinding the coil 102 in the delivery shaft does not permanently unwind the coil 102. In particular, the coil 102 may comprise a shape-memory material that is configured to return from a temporary deformed shape (e.g., unwound configuration, delivery configuration) to an original permanent shape (e.g., coiled configuration, deployed configuration) responsive to a stimulus (e.g., temperature change, electric current, electromagnetic radiation, mechanical stress, etc.) and/or when not constrained by the delivery shaft of the docking device delivery apparatus. As examples, the shape-memory material may comprise a shape-memory alloy (e.g., Nitinol) and/or shape-memory polymer. Thus, the coil 102 can be wound and/or unwound between a coiled configuration (also referred to as "deployed configuration" and "helical configuration"), which is depicted in FIGS. 4-5, and an uncoiled configuration (also referred to as "delivery configuration" and "substantially straight configuration").

In some embodiments, the coil 102 is configured to return to its original coiled configuration when released from the delivery shaft within a patient's heart. In some such embodiments, the coil 102 may be configured to return to its original coiled shape due to the warming experienced within the patient's body and/or release from the delivery shaft. Specifically, the coil 102 may have a transformation temperature (temperature above which the coil 102 exhibits its shape memory effects and behaves superelastically) that is the same as or close to (e.g., slightly below) human body temperature (e.g., 37° C.). In this way, coil 102 can be mechanically unwound to fit inside the delivery shaft at, for example, a temperature below the human body temperature. Once heated to its transformation temperature by the patient's body heat, the coil 102 may automatically and passively wind itself to its original coiled configuration when it is released and/or removed from the delivery shaft within the patient's vasculature.

FIGS. 4-5 illustrate the coil 102 in its original permanent shape (coiled configuration). As explained above, the docking device 100 may have this coiled shape/structure prior to being loaded in the delivery shaft and/or after being pushed out of and/or otherwise released from the delivery shaft, such as after deployment and/or implantation at the native heart valve. However, the coiled configuration shown in FIGS. 4-5 is not the final shape of the coil 102. The coil 102 may radially expand when a prosthetic heart valve is expanded within the docking device 100. Specifically, and as will be explained in greater detail below, the third portion 124 of the second section 112 may radially expand such that the second portion 122 no longer extends and/or flares radially outwardly from the third portion 124. For example, the third portion 124 and the second portion 122 may become substantially congruent after the prosthetic heart valve has been expanded within the docking device 100. FIGS. 20-21 and 23-35 depict an exemplary coil in this final assembled configuration where a prosthetic heart valve has been expanded within the docking device.

The lumen 103 is defined by the coil 102 and is configured to receive a prosthetic heart valve. For example, the lumen 103 may be sized and/or shaped to receive the prosthetic heart valve. In some embodiments, the lumen 103 may be sized and/or shaped to receive the prosthetic heart valve when the prosthetic heart valve is in a radially compressed position (i.e., delivery configuration) and may be configured to radially expand when the prosthetic heart valve is radially expanded therein. When the prosthetic heart valve is not deployed within the docking device 100 and the docking device 100 is not positioned within a patient, the lumen 103 may comprise a hollow or empty space within the coil 102. The lumen 103 may extend between the interior-facing surfaces of the coil 102 (the surfaces that face radially inwards), from the first end 106 to the second end 108 of the docking device 100.

Expandable sleeve 104 covers at least a portion of the coil 102 and is configured to provide a seal between a prosthetic heart valve and the native heart valve tissue to reduce PVL. As introduced above, the expandable sleeve 104 is configured to extend along the outflow side of the native valve, over the outflow section 112 of the coil 102. By positioning the PVL guard on the outflow (ventricular) side of a mitral valve, hemodynamic pressure (e.g., systolic blood pressure) may urge the PVL guard against and/or into the native tissue (as opposed to away from it), thereby providing a seal between the native heart valve tissue and the prosthetic heart valve. In some examples, the expandable sleeve 104 is configured to extend at least 100 degrees around the ventricular side of an anterior leaflet of the mitral valve towards and/or to the anterolateral commissure of the mitral valve. By extending farther along the ventricular side of the mitral valve in this manner, the expandable sleeve 104 may reduce and/or prevent PVL around the prosthetic heart valve, especially at and/or near the anterolateral and/or posteromedial commissures.

Expandable sleeve 104 comprises a first end 126 (which may also be referred to herein as "proximal end 126") and a second end 128 (which may also be referred to herein as "distal end 128"). The expandable sleeve 104 covers at least a portion of the coil 102, as illustrated in FIGS. 4-5. Thus, the portions of the coil 102 that are covered by the expandable sleeve 104 are illustrated in dashed lines in FIGS. 4-5 to show that these portions of the coil 102 are not visible from the exterior of the docking device 100.

In some embodiments, the expandable sleeve 104 may have a generally tubular shape that surrounds and completely covers the coil 102 along the length of the expandable sleeve 104 (from the first end 126 to the second end 128 of the expandable sleeve). That said, the expandable sleeve 104 may be shorter than the coil 102 and thus may not cover the entire length of the coil 102. For example, the expandable sleeve 104 may extend distally from the second portion 116 of first section 110 of the coil 102 and/or the first portion 114 of the first section 110 of the coil 102 to the first portion 120 of the second section 112 of the coil 102.

In some such embodiments, the expandable sleeve 104 extends from at least where the first section 110 and second section 112 meet (where the second portion 116 of the first section 110 ends and the first portion 120 of the second section 112 begins) to a more distal position on the first portion 120 of the second section 112. Specifically, the expandable sleeve 104 may extend distally at least 90 degrees, at least 100 degrees, at least 110 degrees, at least 120 degrees, at least 130 degrees, at least 140 degrees, at least 150 degrees, at least 160 degrees, at least 170 degrees, at least 180 degrees, at least 190 degrees, at least 200 degrees, at least 210 degrees, at least 240 degrees, at least 270 degrees, at least 300 degrees, at least 330 degrees, at least 360 degrees, at most 540 degrees, at most 450 degrees, at most 360 degrees, at most 270 degrees, at most 240 degrees, at most 210 degrees, at most 180 degrees, and/or at most 150 degrees away from the second portion 116 of the first section 110 to where it terminates on the first portion 120 of the second section 112 (i.e., at its second end 128). Thus, stated slightly different, the second end 128 of the expandable sleeve 104 may be disposed/positioned at least 90 degrees, at least 100 degrees, at least 110 degrees, at least 120 degrees, at least 130 degrees, at least 140 degrees, at least 150 degrees, at least 160 degrees, at least 170 degrees, at least 180 degrees, at least 190 degrees, at least 200 degrees, at least 210 degrees, at least 240 degrees, at least 270 degrees, at least 300 degrees, at least 330 degrees, at least 360 degrees, at most 540 degrees, at most 450 degrees, at most 360 degrees, at most 270 degrees, at most 240 degrees, at most 210 degrees, at most 180 degrees, and/or at most 150 degrees away from the second portion 116 of the first section 110 of the coil 102.

In some embodiments, the second end 128 of the expandable sleeve 104 is configured to be disposed/positioned at, or proximate to, an anterolateral commissure, anterolateral side, and/or A1/P1 position of a mitral valve when implanted at the mitral valve. For example, the second end 128 of the expandable sleeve 104 may be disposed/positioned no more than 90 degrees, no more than 80 degrees, no more than 70 degrees, no more than 60 degrees, no more than 50 degrees, no more than 40 degrees, no more than 30 degrees, no more than 20 degrees, no more than 10 degrees, and/or no more than 5 degrees from the anterolateral commissure and/or A1/P1 position of the native mitral valve.

From the above, it should be clear that the expandable sleeve 104 extends proximally from its second end 128, over the coil 102 and towards the first end 106 of the docking device 100. In some embodiments the expandable sleeve 104 extends at least at least 210 degrees, at least 230 degrees, at least 250 degrees, at least 270 degrees, at least 280 degrees, at least 290 degrees, at least 300 degrees, at least 310 degrees, at least 320 degrees, at least 330 degrees, at least 340 degrees, at least 350 degrees, at least 360 degrees, at least 370 degrees, at least 380 degrees, at least 390 degrees, at least 400 degrees, at most 720 degrees, at most 630 degrees, at most 540 degrees, at most 450 degrees, at most 420 degrees, at most 390 degrees, at most 380 degrees, at most 370 degrees, and/or at most 360 degrees from its second end 128 to its first end 126. Stated slightly differently, the expandable sleeve 104 may cover and/or surround at least 10%, at least 12%, at least 14%, at least 16%, at least 18%, at least 20%, at least 22%, at least 24%, at least 25%, at least 30%, at least 35%, at most 50%, at most 40%, at most 30%, and/or at most 25% of the length of the coil 102.

Thus, the expandable sleeve 104 may extend proximally from its second end 128 over the first portion 120 of the second section 112 of the coil 102 and over at least a portion or all of the second portion 116 of the first section 110. In some embodiments, the expandable sleeve 104 extends all the way to and/or over the first portion 114 of the first section 110. However, in other embodiments, the expandable sleeve 104 stops short of the first portion 114 of the first section 110 and does not extend over the entire length of the second portion 116 of the first section 110 of the coil 102.

In some embodiments, expandable sleeve 104 may be coupled to the coil 102 at its second end 128. In some such embodiments, the second end 128 may be fixedly attached and/or otherwise permanently secured to the coil 102 via one or more stitches, adhesives, and/or other means for coupling. For example, U.S. Provisional Patent Application No. 63/105,099 entitled "PROSTHETIC VALVE DOCKING DEVICE," filed Oct. 23, 2020, which is incorporated by reference herein in its entirety, describes various exemplary ways to attach the expandable sleeve 104 to the coil 102.

In some such embodiments, only the second end 128 of the expandable sleeve 104 is fixedly coupled to the coil 102 and the rest of the expandable sleeve 104 may be free to float around, expand away from, and/or axially move relative to the coil 102. In some such embodiments, the expandable sleeve 104 may be configured to slide towards the second end 128 relative to the coil 102 when radially expanding after a crimping pressure is released, such as when the coil 102 is released from the docking device delivery apparatus. However, in other embodiments, the first end 126 of the expandable sleeve 104 and/or other portions of the expandable sleeve 104 may also or alternatively be coupled to the coil 102 via stitches, adhesives, and/or other means for coupling.

Expandable sleeve 104 is deformable and is configured to radially expand when a crimping pressure is released, such as when a sleeve shaft (e.g., sleeve shaft 34 described above) is retracted, removed, and/or otherwise withdrawn from the expandable sleeve 104. That is, expandable sleeve 104 may be self-expanding and may be configured to radially expand when not constrained by a sleeve. In particular, the expandable sleeve 104 may be configured to expand and/or contract between an expanded position (e.g., FIG. 15) and a compressed position (e.g., FIG. 14). For example, the expandable sleeve 104 may comprise a shape-memory material (e.g., Nitinol and/or memory foam) that is configured to return to its original permanent shape (expanded position) responsive to a stimulus (e.g., temperature change, electric current, electromagnetic radiation, mechanical stress, etc.) and/or upon removal of a crimping pressure (e.g., when not constrained by the sleeve shaft).

In some such embodiments, the expandable sleeve 104 may be configured to return to its original expanded position due to the warming experienced within the patient's body and/or upon removal of a crimping pressure (such as when released from the sleeve shaft). Specifically, the expandable sleeve 104 may have a transformation temperature (temperature above which the coil 102 exhibits its shape memory effects and behaves super-elastically) that is the same as or close to (e.g., slightly below) the human body temperature (e.g., 37° C.). In this way, expandable sleeve 104 can be radially compressed and lengthened (longitudinally/axially elongated) within the sleeve shaft at, for example, a temperature below the human body temperature. Once heated to its transformation temperature by the patient's body heat, the expandable sleeve 104 may automatically and passively radially expand and longitudinally/axially compress (i.e., shorten) to its original expanded position when it is released and/or removed from the sleeve shaft within the patient's vasculature. As another example, the expandable sleeve 104 comprises a memory foam that is configured to radially expand to a pre-set shape upon removal of a crimping pressure (e.g., when removed from the docking device delivery apparatus and/or the sleeve shaft of the docking device delivery apparatus). The expandable sleeve 104 may slide axially over the coil 102 towards the second end 108 of the coil 102 as it axially shortens when moving from the compressed position to the expanded position.

Thus, FIGS. 4-5 illustrate the expandable sleeve 104 in its original permanent shape (expanded position). As explained above, the expandable sleeve 104 may be in this expanded position prior to being loaded in the sleeve shaft and/or after being pushed out of and/or otherwise released from the sleeve shaft, such as after deployment and/or implantation at the native heart valve.

In some embodiments, the expandable sleeve 104 may be tapered at and/or proximate to the second end 128. That is, the expandable sleeve 104 may narrow (extend radially inwardly towards the coil 102) near and/or at the second end 128. In some such embodiments, the expandable sleeve 104 may be narrowest at the second end 128, such that the second end 128 is narrower than the rest of the expandable sleeve 104.

Figure 6:
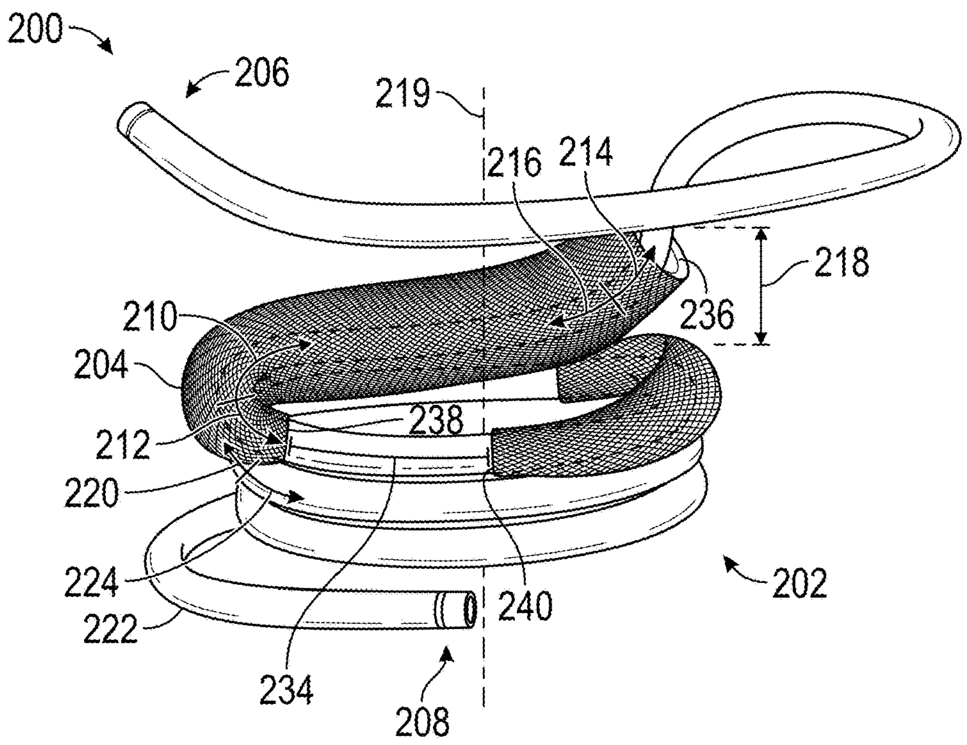
FIG. 6 illustrates a perspective view of a docking device, according to an embodiment.
Figure 7:
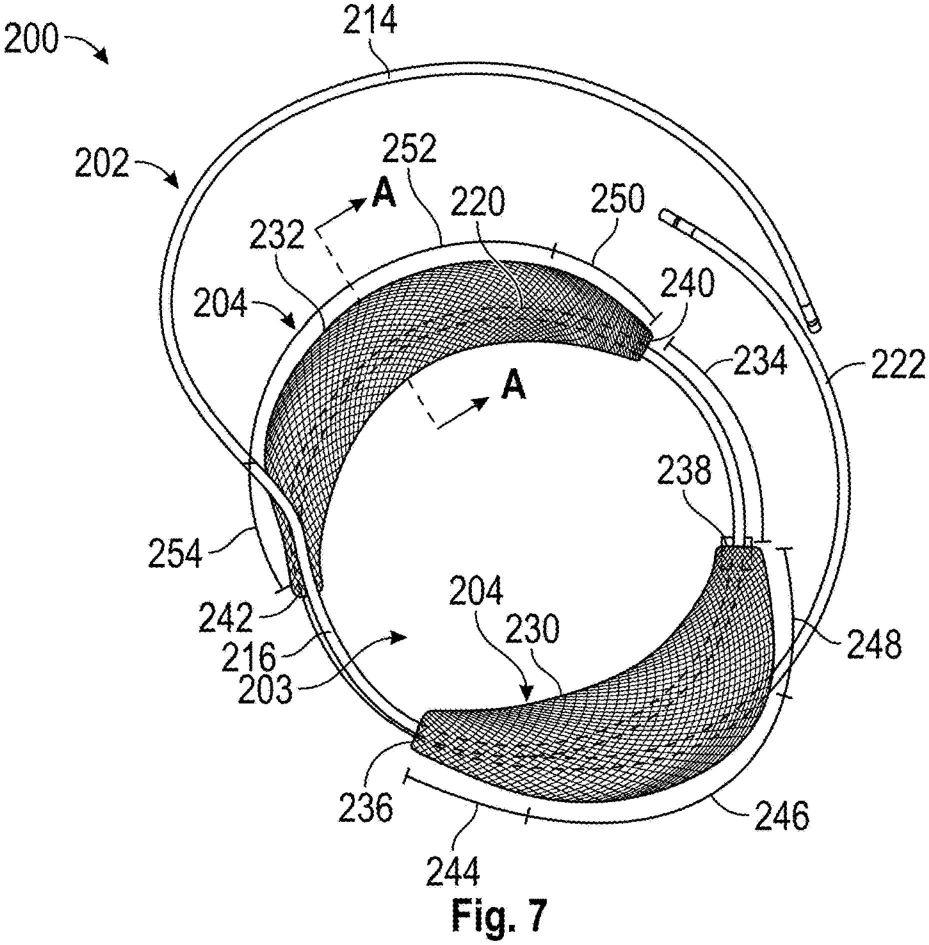
FIG. 7 illustrates a top view of the docking device of FIG. 6.

FIGS. 6-7 depict a docking device 200, according to another embodiment. Specifically, FIG. 6 depicts a side perspective view of the docking device 200 and FIG. 7 depicts a top view of the docking device 200. The docking device 200 may comprise one or more components that are generally similar to one or more components of the docking device 100. Thus, for conciseness, the components of the docking device 200 that are similar to the components of the docking device 100 are labeled similarly and may not include additional description. For example, the docking device 200 comprises a coil 202 and an expandable sleeve 204, and has a first end 206 and a second end 208 (corresponding to the coil 102, the expandable sleeve 104, the first end 106, and the second end 108, respectively, of the docking device 100).

However, in the embodiment of FIGS. 6-7, the expandable sleeve 204 comprises two distinct sleeves, a first expandable sleeve 230 and a second expandable sleeve 232, that are separated from one another on the coil 202 by a gap 234. Thus, in the embodiment of FIGS. 6-7, the expandable sleeve 204 does not cover and/or surround the coil 202 at the gap 234, and thus the coil 202 may be exposed where the gap 234 exists. As one example, the first expandable sleeve 230 can be positioned on an inflow side of a native valve (and thus may cover at least a portion of the first section 210 of the coil 202), and the second expandable sleeve 232 can be positioned on an outflow side of the native valve (and thus may cover at least a portion of the second section 212 of the coil 202). In this manner, the sleeves 230, 232 can reduce or eliminate PVL.

The first expandable sleeve 230 has a first end 236 (which may also be referred to herein as "proximal end 236" and a second end 238 (which may also be referred to herein as "distal end 238"). Similarly, the second expandable sleeve 232 has a first end 240 (which may also be referred to herein as "proximal end 240") and a second end 242 (which may also be referred to herein as "distal end 242"). The first end 236 of the first expandable sleeve 230 may be similar to and/or correspond to the first end 126 of the expandable sleeve 104 of the docking device 10 and may be positioned/disposed at the same and/or similar location on the coil 202. For example, the first end 236 of the first expandable sleeve 230 may be positioned/disposed at the first portion 214 of the first section 210, the junction of the first portion 214 and the second portion 216 of the first section 210, and/or the second portion 216 of the first section 210. Additionally or alternatively, the second end 242 of the second expandable sleeve 232 may be similar to and/or correspond to the second end 128 of the expandable sleeve 104 of the docking device 100 and may be positioned/disposed at the same and/or similar location on the coil 202. For example, the second end 242 may be positioned/disposed distally at least 90 degrees, at least 100 degrees, at least 110 degrees, at least 120 degrees, at least 130 degrees, at least 140 degrees, at least 150 degrees, at least 160 degrees, at least 170 degrees, at least 180 degrees, at least 190 degrees, at least 200 degrees, at least 210 degrees, at least 240 degrees, at least 270 degrees, at least 300 degrees, at least 330 degrees, at least 360 degrees, at most 540 degrees, at most 450 degrees, at most 360 degrees, at most 270 degrees, at most 240 degrees, at most 210 degrees, at most 180 degrees, and/or at most 150 degrees away from the junction of the first section 210 and the second section 212. Thus, the length of the coil 202 that exists between the first end 236 of the first expandable sleeve 230 and the second end 242 of the second expandable sleeve 232 may be the same and/or similar to the length of the coil 202 that exists between the first end 126 and the second end 128 of the expandable sleeve 104.

The gap 234 may at the first portion 220 of the second section 212 of the coil 202 and may extend distally towards the second end 208 of the docking device 200 from and/or near the junction of the first portion 220 and the first section 210. Thus, the first portion 220 of the second section 212 of the coil 202 may be exposed by the gap 234. The gap 234 may be configured to be positioned at, adjacent to, and/or proximate to an inflow and/or outflow tract of a neighboring heart valve. For example, the gap 234 may be positioned at, adjacent to, and/or proximate to an anterior leaflet of a native mitral valve and/or a left ventricular outflow tract (LVOT) of the left ventricle when the docking device 200 is implanted at a native mitral valve. In this manner, the docking device 200 may reduce and/or prevent obstructions to the flow of blood through the aortic valve.

The gap 234 separates the first expandable sleeve 230 from the second expandable sleeve 232 such that the first expandable sleeve 230 and the second expandable sleeve 232 do not directly physically contact one another, at least when the first expandable sleeve 230 and the second expandable sleeve 232 are in the expanded positions illustrated in FIGS. 6-7. That said, the second expandable sleeve 232 may directly physically contact the first expandable sleeve 230 when the second expandable sleeve 232 is radially compressed and lengthened (axially elongated) in the compressed position, such as when it is constrained within the sleeve shaft. Thus, the length of the gap 234 may change depending on whether the second expandable sleeve 232 is in the compressed position or the expanded position. In particular, the length of the gap 234 may increase when the second expandable sleeve 232 radially expands (and longitudinally/axially shortens) from its compressed position to its expanded position, such as when it is released from the sleeve shaft.

In the expanded position illustrated in FIGS. 6-7, the gap 234 extends and/or may separate the first expandable sleeve 230 and the second expandable sleeve 232 by at least 10 degrees, at least 20 degrees, at least 30 degrees, at least 40 degrees, at least 50 degrees, at least 60 degrees, at least 70 degrees, at least 80 degrees, at least 90 degrees, at most 180 degrees, at most 160 degrees, at most 140 degrees, at most 120 degrees, at most 110 degrees, at most 100 degrees, at most 90 degrees, at most 80 degrees, at most 70 degrees, and/or at most 60 degrees.

The second expandable sleeve 232 may extend proximally towards the first section 210 from its second end 242, but may stop short of the first section 210. Additionally or alternatively, the first expandable sleeve 230 may extend distally towards the second section 212 from its first end 236, but may stop short of the second section 212. As examples, the second expandable sleeve 232 may extend proximally from the second end 242 and/or the first expandable sleeve 230 may extend distally from the first end 236 at least 30 degrees, at least 60 degrees, at least 80 degrees, at least 90 degrees, at least 100 degrees, at least 110 degrees, at least 120 degrees, at least 130 degrees, at least 140 degrees, at least 150 degrees, at least 160 degrees, at least 170 degrees, at least 180 degrees, at least 190 degrees, at least 200 degrees, at most 270 degrees, at most 250 degrees, at most 230 degrees, at most 210 degrees, at most 200 degrees, at most 190 degrees, at most 180 degrees, at most 170 degrees, at most 160 degrees, at most 150 degrees, at most 140 degrees, at most 130 degrees, at most 120 degrees, at most 110 degrees, at most 110 degrees and/or at most 100 degrees.

In some embodiments, the second expandable sleeve 232 may be coupled to the coil 202 at its second end 242. For example, the second end 242 may be fixedly attached and/or otherwise permanently secured to the coil 202 via one or more stitches, adhesives, and/or other suitable coupling mechanisms, like the second end 128 of the expandable sleeve 104. Additionally or alternatively, the first expandable sleeve 230 may be coupled to the coil 202 at its second end 238. For example, the second end 238 may be fixedly attached and/or otherwise permanently secured to the coil 202 via one or more stitches, adhesives, and/or other suitable coupling mechanisms, like the second end 128 of the expandable sleeve 104.

In some such embodiments, only the second end 238 of the first expandable sleeve 230 and/or the second end 242 of the second expandable sleeve 232 is/are coupled to the coil 202 and the rest of the first expandable sleeve 230 and/or the second expandable sleeve 232 may be free to float around, expand away from, and/or axially move relative to the coil 202. However, in other embodiments, the first end 236 of the first expandable sleeve 230, the first end 240 of the second expandable sleeve 232, and/or other portions of the first expandable sleeve 230 and/or second expandable sleeve 232 may also or alternatively be coupled to the coil 202 via stitches, adhesives, and/or other suitable coupling mechanisms.

In some embodiments, the second end 238 of the first expandable sleeve 230 is configured to be positioned at the junction of the first section 210 and the second section 212 of the coil 202 (i.e., the distal end of the first section 210). In some embodiments, the second end 242 of the second expandable sleeve 232 is configured to be positioned at least 120 degrees, at least 130 degrees, at least 140 degrees, at least 150 degrees, at least 160 degrees, at least 170 degrees, at least 180 degrees, at least 190 degrees, at least 200 degrees, at least 210, at least 220, at most 360 degrees, at most 270 degrees, at most 230 degrees, at most 210 degrees, at most 200 degrees, at most 190 degrees, and/or at most 180 degrees from the first section 210.

In some embodiments, the first expandable sleeve 230 and/or the second expandable sleeve 232 may be tapered at and/or proximate to the second end 238 and/or the second end 242, respectively. That is, the first expandable sleeve 230 may narrow near (extend radially inward towards the coil 202) and/or at the second end 238 and/or the second expandable sleeve 232 may narrow (extend radially inward towards the coil 202) near and/or at the second end 242. In some such embodiments, the first expandable sleeve 230 and/or the second expandable sleeve 232 may be narrowest at the second end 238 and/or second end 242, respectively, such that the second end 238 and/or the second end 242 is narrower than the rest of the first expandable sleeve 230 and/or second expandable sleeve 232, respectively.

In some embodiments, the first expandable sleeve 230 and/or the second expandable sleeve 232 may additionally or alternatively be tapered (extend radially inwardly towards the coil 202) at and/or proximate to the first end 236 and/or the first end 240, respectively. That is, the first expandable sleeve 230 may narrow near and/or at the first end 236 and/or the second expandable sleeve 232 may narrow near and/or at the first end 240.

Specifically, the first expandable sleeve 230 may comprise a first portion 244 that extends distally from the first end 236, a second portion 246 that extends proximally from the second end 238, and a third portion 248 that is disposed between the first portion 244 and the second portion 246 and that is thicker (i.e., extends farther radially away from the coil 202) than the first portion 244 and the second portion 246. For example, the third portion 248 may extend radially away at least 1.2, at least 1.4, at least 1.6, at least 1.8, at least 2, at least 2.5, at least 3, at most 10, at most 9, at most 8, at most 7, at most 6, at most 5, at most 4, and/or at most 3 times as far from the coil 102 as the first portion 244 and/or the second portion 246. In some such embodiments, the first portion 244 and/or the second portion 246 may be tapered such that the first portion 244 monotonically narrows towards the first end 236 and/or the second portion 246 monotonically narrows towards the second end 238.

Similarly, the second expandable sleeve 232 may comprise a first portion 250 that extends distally from the first end 240, a second portion 252 that extends proximally from the second end 242, and a third portion 254 that is disposed between the first portion 250 and the second portion 252 and that is thicker than the first portion 250 and the second portion 252. For example, the third portion 254 may extend radially away from the coil 302 at least 1.2, at least 1.4, at least 1.6, at least 1.8, at least 2, at least 2.5, at least 3, at most 10, at most 9, at most 8, at most 7, at most 6, at most 5, at most 4, and/or at most 3 farther than the first portion 250 and/or the second portion 252. As another example, the cross-sectional area ((e.g., when viewed in an orthogonal cutting plane like cutting plane A-A) of the third portion 254 may be at least 1.5, at least 2, at least 2.5, at least 3, at least 3.5, at least 4, at most 50, at most 40, at most 30 at most 20, at most 10, at most 8, and/or at most 6 times greater than the cross-sectional areas of the first portion 250 and/or the second portion 252.

In some such embodiments, the first portion 250 and/or the second portion 252 may be tapered such that the first portion 250 monotonically narrows towards the first end 240 and/or the second portion 252 monotonically narrows towards the second end 242.

First portion 244 and/or first portion 250 may comprise at least 5%, at least 10%, at least 15%, at least 20%, at least 25%, at least 30%, at least 35%, at least 40%, at most 60%, at most 55%, at most 50%, at most 45%, at most 40% and/or at most 35% of the length of the first expandable sleeve 230 and/or the second expandable sleeve 232, respectively. Second portion 246 and/or second portion 252 may comprise at least 5%, at least 10%, at least 15%, at least 20%, at least 25%, at least 30%, at least 35%, at least 40%, at most 60%, at most 55%, at most 50%, at most 45%, at most 40% and/or at most 35% of the length of the first expandable sleeve 230 and/or the second expandable sleeve 232, respectively. Third portion 248 and/or third portion 254 may comprise at least 20%, at least 30%, at least 40%, at least 50%, at least 55%, at least 60%, at least 65%, at least 70%, at least 75%, at least 80%, at most 90%, at most 85%, at most 80%, at most 75%, at most 70%, at most 65%, at most 60%, at most 55%, and/or at most 50% of the length of the first expandable sleeve 230 and/or the second expandable sleeve 232, respectively.

Figure 8:
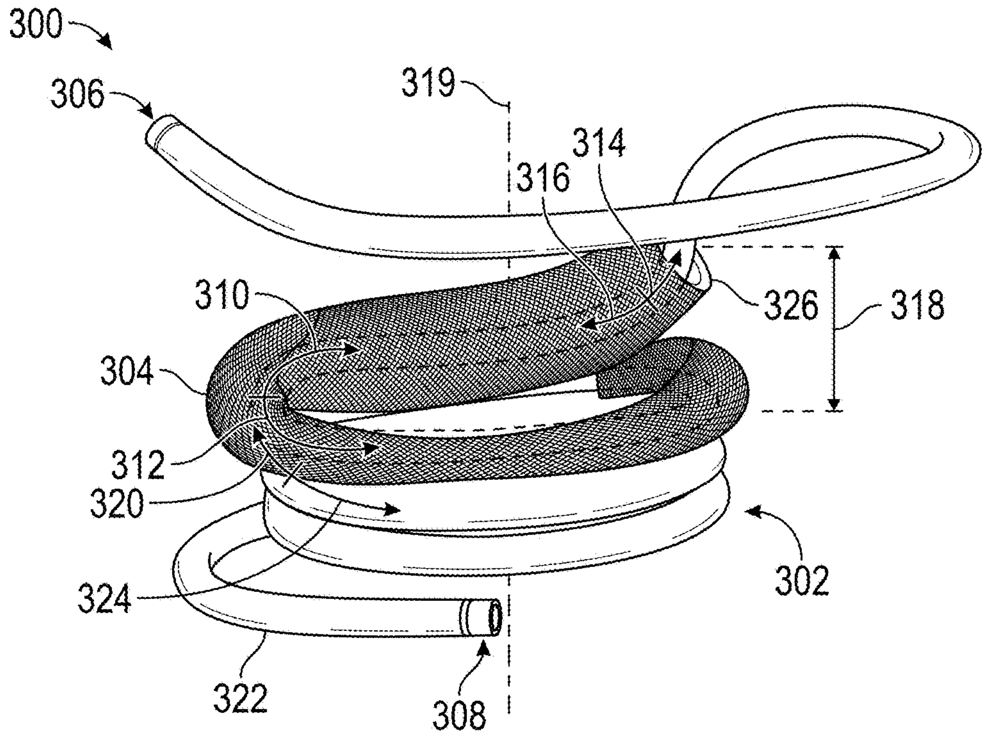
FIG. 8 illustrates a perspective view of a docking device, according to an embodiment.
Figure 9:
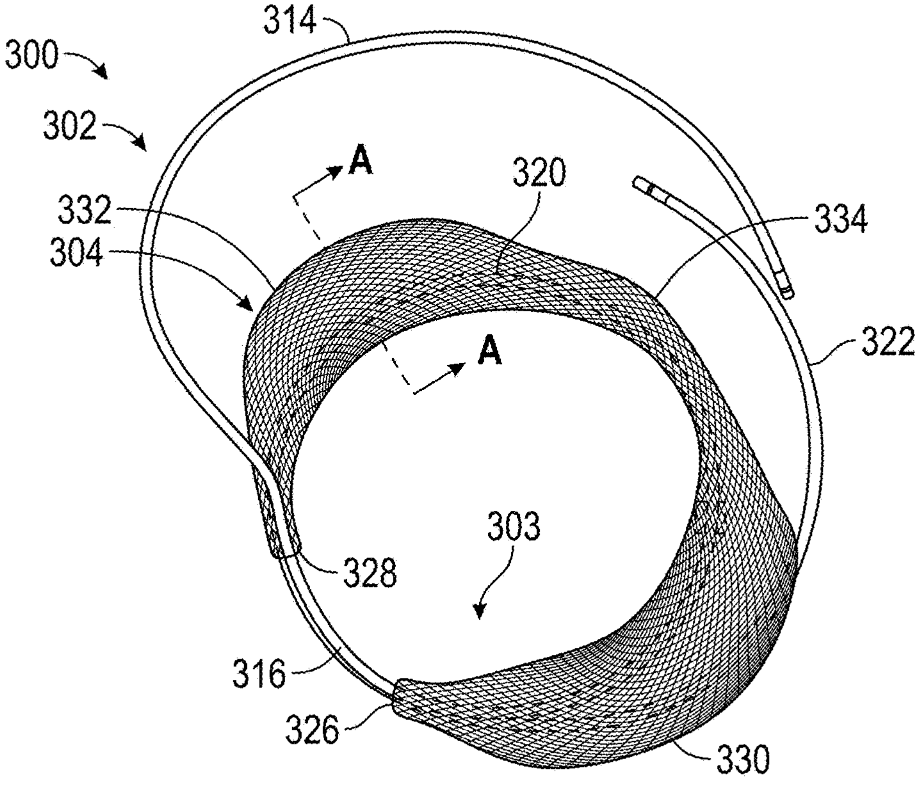
FIG. 9 illustrates a top view of the docking device of FIG. 8.

FIGS. 8-9 depict a docking device 300, according to another embodiment. Specifically, FIG. 8 depicts a side perspective view of the docking device 300 and FIG. 9 depicts a top view of the docking device 300. The docking device 300 may comprise one or more components that are generally similar to one or more components of the docking device 100. Thus, for conciseness, the components of the docking device 300 that are similar to the components of the docking device 100 are labeled similarly and may not include additional description. For example, the docking device 300 comprises a coil 302 and an expandable sleeve 304, and has a first end 306 and a second end 308 (corresponding to the coil 102, the expandable sleeve 104, the first end 106, and the second end 108, respectively, of the docking device 100).

In the embodiment illustrated in FIGS. 8-9, an intermediate section of the coil 302, which may be configured to be positioned at and/or near the inflow and/or outflow tract of a neighboring heart valve (e.g., at and/or near the LVOT when the docking device is implanted at a native mitral valve), is tapered. As such, the expandable sleeve 304 may reduce and/or prevent obstructions to the flow of blood through the neighboring native heart valve.

The expandable sleeve 304 may comprise a first portion 330 that extends distally from the first end 326, a second portion 332 that extends proximally from the second end 328, and a third portion 334 (which may also be referred to herein as "tapered portion 334," "intermediate tapered portion 334," and/or "intermediate portion 334") that is disposed between the first portion 330 and the second portion 332 and is narrower than the first portion 330 and the second portion 332. For example, the first portion 330 and/or the second portion 332 may extend radially away from the coil 302 at least 1.2, at least 1.4, at least 1.6, at least 1.8, at least 2, at least 2.5, at least 3, at most 10, at most 9, at most 8, at most 7, at most 6, at most 5, at most 4, and/or at most 3 times farther than the third portion 334. As another example, the cross-sectional areas (e.g., when viewed in an orthogonal cutting plane like cutting plane A-A) of the first portion 330 and/or the second portion 332 be at least 1.5, at least 2, at least 2.5, at least 3, at least 3.5, at least 4, at most 50, at most 40, at most 30 at most 20, at most 10, at most 8, and/or at most 6 times greater than the cross-sectional area of the third portion 334.

The third portion 334 may cover, surround, and/or be disposed at the junction between the first section 310 and the second section 312 of the coil 302 (which may be configured to be positioned at or proximate to a posteromedial side and/or A3/P3 position of a native mitral valve). In some such embodiments, the third portion 334 of the coil 302 is configured to be positioned at or proximate to an inflow and/or outflow tract of an adjacent native heart valve. For example, the third portion 334 of the coil 302 may be configured to be positioned at or proximate to the left ventricular outflow tract (LVOT). In this way, the intermediate tapered portion 334 may reduce and/or prevent obstructions to the flow of blood through the native aortic valve.

Third portion 334 may comprise at least 10%, at least 15%, at least 20%, at least 25%, at least 30%, at least 35%, at least 40%, at least 45%, at least 50%, at most 75%, at most 65%, at most 55%, at most 50%, at most 45%, and/or at most 40% of the length of the expandable sleeve 304.

FIGS. 10-13 depict exemplary docking devices according to other embodiments in which the first portion of the second section (e.g., the uppermost ventricular turn) of the coil comprises a different geometry (shape and/or size) than the third portion of the second section (e.g., the ventricular side functional turns of the coil). Specifically, the first portion of the second section may define a larger cross-sectional area than the third portion of the second section and/or may be non-circular. By extending radially outwardly beyond the third portion and/or by more closely matching the shape of the native valve annulus, the first portion of the second section of the coil may help anchor the docking device and/or prosthetic heart valve in place relative to the native heart valve tissue, thereby reducing and/or preventing PVL.

Figure 10:
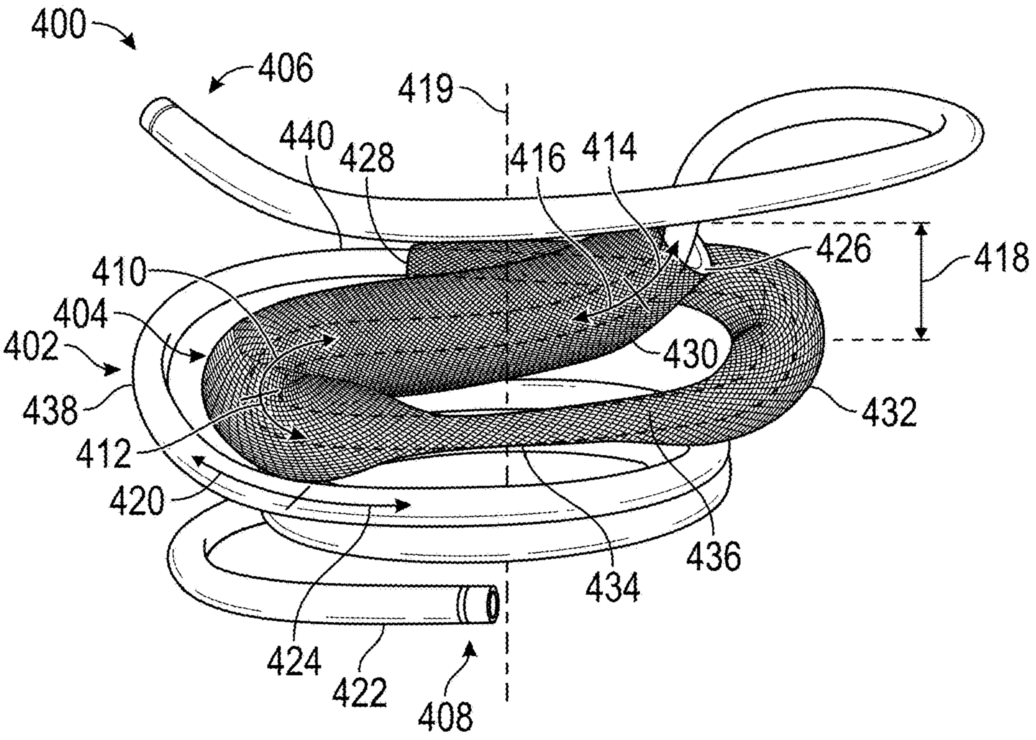
FIG. 10 illustrates a perspective view of a docking device, according to an embodiment.
Figure 11:
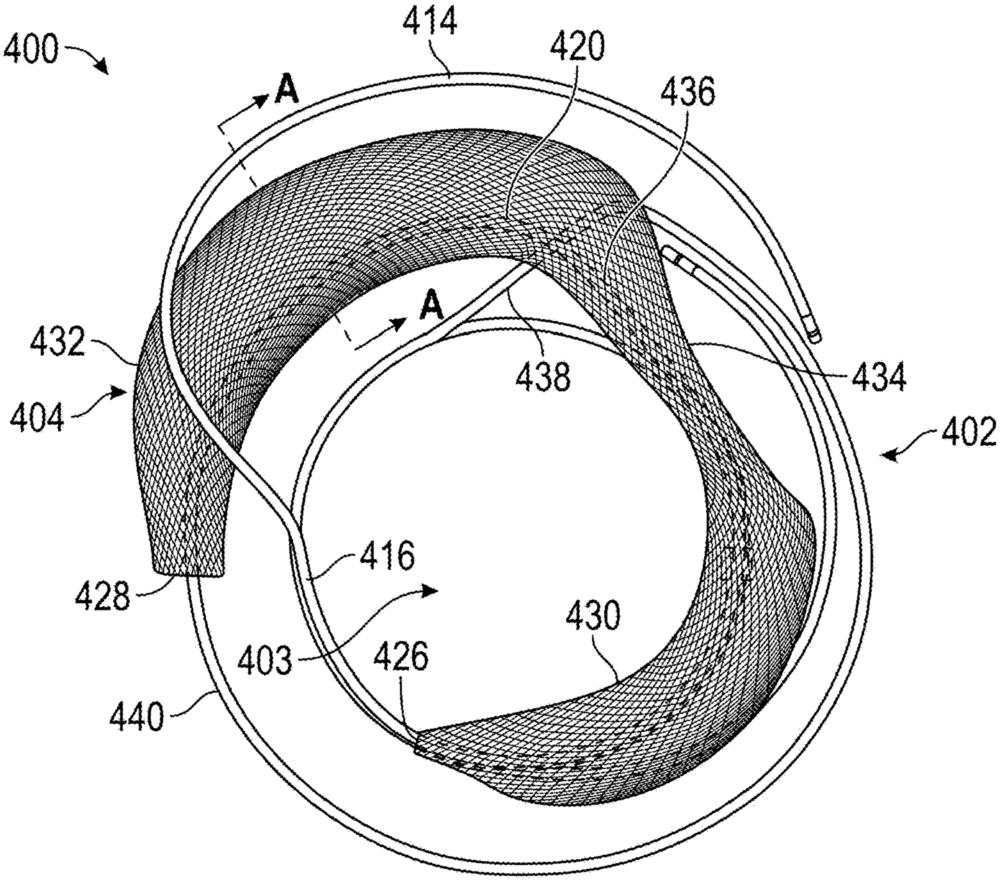
FIG. 11 illustrates a top view of the docking device of FIG. 10.

FIGS. 10-11 depict a docking device 400, according to yet another embodiment. Specifically, FIG. 10 depicts a side perspective view of the docking device 400 and FIG. 11 depicts a top view of the docking device 400. The docking device 400 may comprise one or more components that are generally similar to one or more components of the docking device 100. Thus, for conciseness, the components of the docking device 400 that are similar to the components of the docking device 100 are labeled similarly and may not include additional description. For example, the docking device 400 comprises a coil 402 and an expandable sleeve 404, and has a first end 406 and a second end 408 (corresponding to the coil 102, the expandable sleeve 104, the first end 106, and the second end 108, respectively, of the docking device 100).

However, in the embodiment of FIGS. 10-11, the coil 402 comprises a different geometry (shape and/or size) than the coil 102 of docking device 100. Specifically, in the embodiment of FIGS. 10-11, the first portion 420 of the second section 412 may comprise a larger turn than the first portion 120 of the second section 112 of the coil 102. Thus, in the embodiment of FIGS. 10-11, the first portion 420 of the second section 412 extends radially outwardly from the third portion 424 of the second section 412. In some such embodiments, the first portion 420 is still substantially the same shape as the first portion 120 of the docking device 100 (e.g., circular when viewed from above in a plane perpendicular to the longitudinal axis 419) and thus may be substantially the same shape as the third portion 424 of the second section 412.

First portion 420 may comprise a first segment 436, a second segment 438, and a third segment 440 disposed between the first segment 436 and the second segment 438. The first segment extends distally from the second portion 416 of the first section 410, the third segment 440 extends distally from the first segment 436, and the second segment 438 extends distally from the third segment 440. The first segment 436 flares and/or extends radially outwardly from the second portion 416 of the first section 410 of the coil 402. The third segment 440 may then extend distally from the first segment 436 in a generally circular pattern (may maintain a substantially consistent radial distance from the third portion 424 of the second section 412 of the coil 402). The second segment 438 may flare and/or extend radially inwardly from the third segment 440 towards the third portion 424 of the second section 412 of the coil 402 and conjoin with the third portion 424.

Like the first portion 120, first portion 420 may extend at least 180 degrees, at least 220 degrees, at least 260 degrees, at least 300 degrees, at least 320 degrees, at least 340 degrees, at least 360 degrees, at least 380 degrees, at least 400 degrees, at least 420 degrees, at most 540 degrees, at most 500 degrees, at most 460 degrees, at most 420 degrees, at most 380 degrees, at most 360 degrees, at most 340 degrees, and/or at most 320 degrees between the second portion 416 of the first section 410 of the coil 402 and the third portion 424 of the second section 412 of the coil 402. In some embodiments, the third segment 440 comprises at least 50%, at least 60%, at least 70%, at least 75%, at least 80%, at least 85%, at least 90%, at least 95%, at most 99%, at most 97%, at most 95%, at most 90%, at most 85%, at most 80%, and/or at most 75% of the angular length (e.g., radians, degrees, etc.) of the first portion 420.

In some embodiments, the radial distance (i.e., shortest straight-line radial distance) between the first portion 420 and the third portion 424 may be at least 5%, at least 10%, at least 15%, at least 20%, at least 25%, at least 30%, at least 35%, at least 40%, at least 50%, at least 60%, at least 70%, at least 80%, at least 90%, at least 100%, at most 500%, at most 400%, at most 300%, at most 200%, at most 150%, at most 100%, and/or at most 75% of the radius of the turns of the third portion 424. Stated differently, the cross-sectional area defined by the first portion 420 (in a plane perpendicular to the longitudinal axis 419) may be at least 5%, at least 10%, at least 15% at least 20%, at least 25%, at least 30%, at least 40%, at least 50%, at least 60%, at least 70%, at least 85%, at least 100%, at least 150%, at least 200%, at least 250%, at least 300%, at least 400%, at least 500%, at most 2500%, at most 2000%, at most 1000%, at most 600%, at most 500%, at most 400%, at most 300%, at most 200%, and/or at most 100% larger than the cross-sectional area defined by the third portion 424. In other words, the cross-sectional area defined by the first portion 420 (in a plane perpendicular to the longitudinal axis 419) may be at least 1.2, at least 1.4, at least 1.6, at least 1.8, at least 2, at least 2.5, at least 3, at least 3.5, at least 4, at least 4.5, at least 5, at most 25, at most 20, at most 15, at most 10, at most 5, and/or at most 4, times greater than the cross-sectional area defined by the third portion 424.

Although FIGS. 10-11 depict the first portion 420 as being circular when viewed from above in a plane perpendicular to the longitudinal axis 419, it should be appreciated that the first portion 420 may comprise a different shape than the shape illustrated in FIGS. 10-11, such as one or more of elliptical, crescent-shaped, D-shaped, and/or other non-circular curved shapes. In some embodiments, the first portion 420 may be shaped the same as and/or similarly to an annulus of the native heart valve. For example, when implanted at a mitral valve, the first portion 420 may be substantially D-shaped and/or crescent-shaped since (as shown in FIGS. 12-13) since the mitral valve annulus may be substantially D-shaped and/or crescent-shaped.

Expandable sleeve 404 may be the same and/or similar to expandable sleeve 304 shown in FIGS. 8-9 and/or may comprise one or more components that are generally similar to one or more components of the expandable sleeve 304. Thus, for conciseness, the components of the expandable sleeve 404 that are similar to the components of the expandable sleeve 304 are labeled similarly and may not include additional description. For example, the expandable sleeve 404 may comprise an intermediate section that is tapered. More specifically, the expandable sleeve 404 may comprise a first portion 430 that extends distally from the first end 426 of the expandable sleeve 404, a second portion 432 that extends proximally from the second end 428 of the expandable sleeve 404, and a third portion 434 (which may also be referred to herein as "tapered portion 434," "intermediate tapered portion 434," and/or "intermediate portion 434") that is disposed between the first portion 430 and the second portion 432 and that may be narrower than the first portion 430 and the second portion 432 (corresponding to the first portion 330, second portion 332, and third portion 334 of the expandable sleeve 304).

Figure 12:
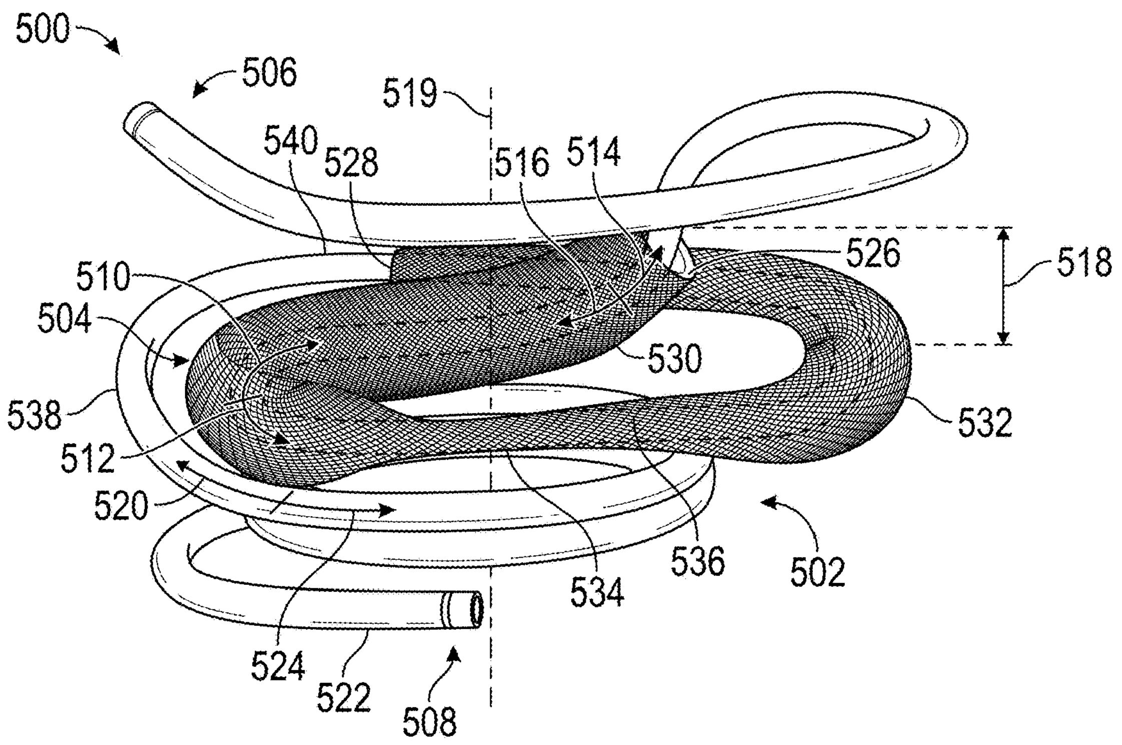
FIG. 12 illustrates a perspective view of a docking device, according to an embodiment.
Figure 13:
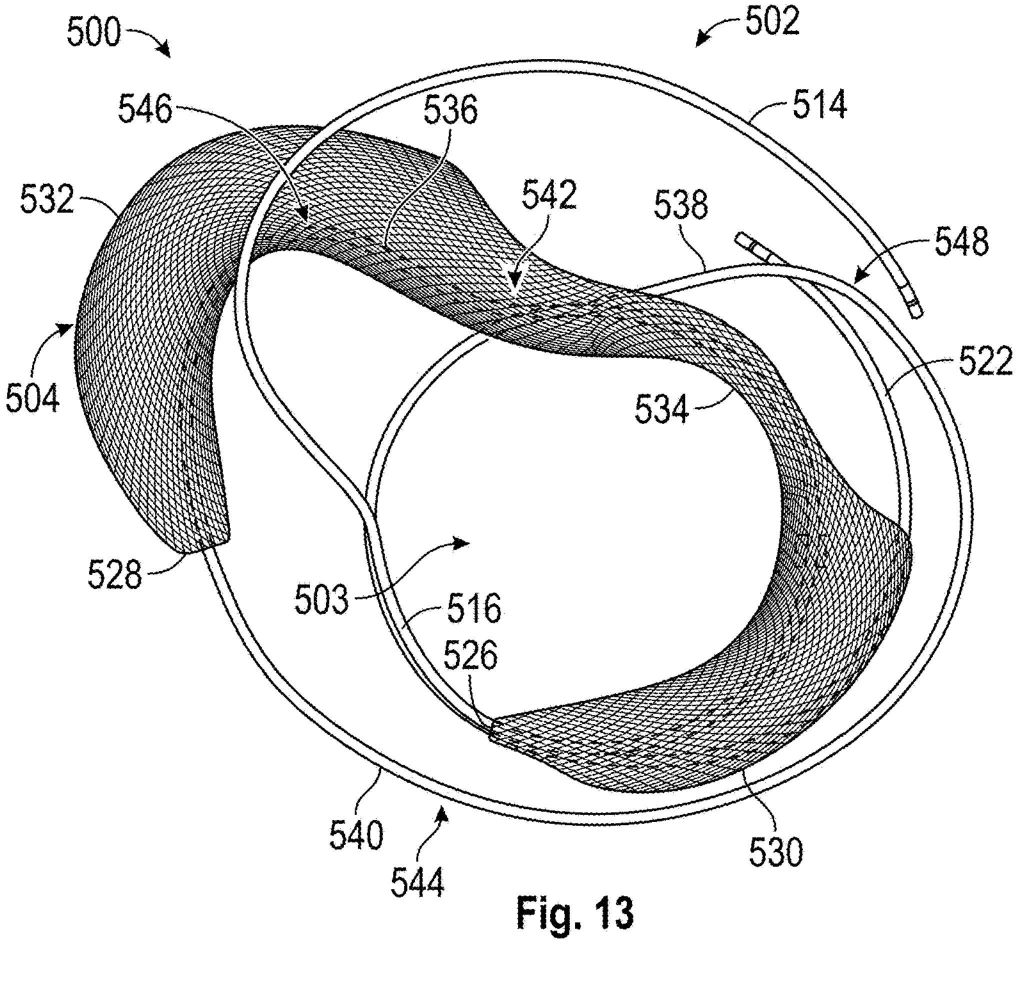
FIG. 13 illustrates a top view of the docking device of FIG. 12.

FIGS. 12-13 depict a docking device 500, according to another embodiment. Specifically, FIG. 12 depicts a side perspective view of the docking device 500 and FIG. 13 depicts a top view of the docking device 500. The docking device 500 may comprise one or more components that are generally similar to one or more components of the docking device 100. Thus, for conciseness, the components of the docking device 500 that are similar to the components of the docking device 100 are labeled similarly and may not include additional description. For example, the docking device 500 comprises a coil 502 and an expandable sleeve 504, and has a first end 506 and a second end 508 (corresponding to the coil 102, the expandable sleeve 104, the first end 106, and the second end 108, respectively, of the docking device 100).

However, in the embodiment of FIGS. 12-13, the coil 502 comprises a different geometry (shape and/or size) than the coil 102 of docking device 100. Specifically, in the embodiment of FIGS. 12-13, the first portion 520 of the second section 512 may comprise a larger and differently shaped turn than the first portion 120 of the second section 112 of the coil 102. First portion 520 may be substantially D-shaped and/or crescent-shaped when viewed from above in a plane perpendicular to the longitudinal axis 519. Further, the first portion 520 may be larger than the third portion 524 of the second section 512 of the coil 502 and may extend radially outwards from the third portion 524.

In particular, the cross-sectional area defined by the first portion 520 (in a plane perpendicular to the longitudinal axis 519) may be at least 5%, at least 10%, east least 15%, at least 20%, at least 25%, at least 30%, at least 40%, at least 50%, at least 60%, at least 70%, at least 85%, at least 100%, at least 150%, at least 200%, at least 250%, at least 300%, at least 400%, at least 500%, at most 2500%, at most 2000%, at most 1000%, at most 600%, at most 500%, at most 400%, at most 300%, at most 200%, and/or at most 100% larger than the cross-sectional area defined by the third portion 524. Stated slightly differently, the cross-sectional area defined by the first portion 520 (in a plane perpendicular to the longitudinal axis 519) may be at least 1.2, at least 1.4, at least 1.6, at least 1.8, at least 2, at least 2.5, at least 3, at least 3.5, at least 4, at least 4.5, at least 5, at most 25, at most 20, at most 15, at most 10, at most 5, and/or at most 4, times greater than the cross-sectional area defined by the third portion 524. Stated slightly differently, the radial distance (i.e., shortest straight-line radial distance) between the first portion 520 and the third portion 524 may be at least 5%, at least 10%, at least 15%, at least 20%, at least 25%, at least 30%, at least 35%, at least 40%, at least 50%, at least 60%, at least 70%, at least 80%, at least 90%, at least 100%, at most 500%, at most 400%, at most 300%, at most 200%, at most 150%, at most 100%, and/or at most 75% of the radius of the turns of the third portion 524. However, since the first portion 520 may be substantially D-shaped and/or crescent-shaped, the radial distance between the first portion 520 and the third portion 524 may not be uniform (i.e., the radial distance between the third portion 524 and the first portion 520 may change along the length of the first portion 520).

In some embodiments, the first portion 520 comprises a first segment 536, a second segment 538, and a third segment 540 disposed between the first segment 536 and the second segment 538. The first segment extends distally from the second portion 516 of the first section 510, the third segment 540 extends distally from the first segment 536, and the second segment 538 extends distally from the third segment 540. The first segment 536 flares and/or extends radially outwardly from the second portion 516 of the first section 510 of the coil 502. The third segment 540 may then extend distally from the first segment 536 in a generally non-circular curved manner (thereby having a variable radial distance the third portion 524 of the second section 512 of the coil 502). The second segment 538 may flare and/or extend radially inwardly from the third segment 540 towards the third portion 524 of the second section 512 of the coil 502 and conjoin with the third portion 524.

In this way, the first segment 536, second segment 538, and third segment 540 may create a substantially D-shaped and/or crescent-shaped profile for the first portion 520 when viewed from above in a plane perpendicular to the longitudinal axis 519. In particular, the first segment 536 and the second segment 538 may form a concave profile 542 when viewed from above in a plane perpendicular to the longitudinal axis 519 and the third segment 540 may form a convex profile 544 when viewed from above in a plane perpendicular to the longitudinal axis 519. Thus, the first segment 536 and the third segment 540 may form a first corner 546 (which may also be referred to herein as "first shoulder 546") where they meet, and similarly, the second segment 538 and the third segment 540 may form a second corner 548 (which may also be referred to herein as "second shoulder 548") where they meet. In some examples, the first portion 520 the farthest radially from the third portion 524 at the corners 546 and 548. That is, the corners 546 and 548 are positioned farther away radially from the third portion 524 than the rest of the first portion 520.

In some embodiments, the corners 546 and 548 are configured to be positioned at, adjacent to, and/or proximate to the anterolateral (and/or A1/P1 position) and posteromedial (and/or A3/P3 position) commissures, respectively, of a native mitral valve. In this way, the first portion 520 may extend closer to the commissures of a native heart valve, thereby providing an enhanced seal between a prosthetic heart valve and the native heart valve tissue and reducing paravalvular leakage at and/or near the commissures.

Like the first portion 120, first portion 520 may extend at least 180 degrees, at least 220 degrees, at least 260 degrees, at least 300 degrees, at least 320 degrees, at least 340 degrees, at least 360 degrees, at least 380 degrees, at least 400 degrees, at least 420 degrees, at most 540 degrees, at most 500 degrees, at most 460 degrees, at most 420 degrees, at most 380 degrees, at most 360 degrees, at most 340 degrees, and/or at most 320 degrees between the second portion 516 of the first section 510 of the coil 502 and the third portion 524 of the second section 512 of the coil 502.

Expandable sleeve 504 may be the same and/or similar to expandable sleeve 304 shown in FIGS. 8-9 and/or may comprise one or more components that are generally similar to one or more components of the expandable sleeve 304. Thus, for conciseness, the components of the expandable sleeve 504 that are similar to the components of the expandable sleeve 304 are labeled similarly and may not include additional description. For example, the expandable sleeve 504 may comprise an intermediate section that is tapered. More specifically, the expandable sleeve 504 may comprise a first portion 530 that extends distally from the first end 526 of the expandable sleeve 504, a second portion 532 that extends proximally from the second end 528 of the expandable sleeve 504, and a third portion 534 (which may also be referred to herein as "tapered portion 534," "intermediate tapered portion 534," and/or "intermediate portion 534") that is disposed between the first portion 530 and the second portion 532 and that may be narrower than the first portion 530 and the second portion 532 (corresponding to the first portion 330, second portion 332, and third portion 334, respectively, of the expandable sleeve 304).

Although FIGS. 4-13 depict three different coil geometries (a first coil geometry in FIGS. 4-9, a second coil geometry in FIGS. 10-11, and a third coil geometry in FIGS. 12-13) and three different expandable sleeve geometries (a first sleeve geometry in FIGS. 4-5, a second sleeve geometry in FIGS. 6-7, and a third sleeve geometry in FIGS. 8-13), it should be appreciated that the coil and/or expandable sleeve may comprise other geometries. For example, the first portion of the second section of the coil may comprise and/or define different shapes and/or sizes than the circular and D-shaped or crescent-shaped geometries shown in FIGS. 4-13. For example, the first portion may be elliptical when viewed from above in a plane perpendicular to the longitudinal axis of the lumen and/or may comprise other curved geometries.

Further, although the second coil geometry shown in FIGS. 10-11 and the third coil geometry shown in FIGS. 12-13 are illustrated as having the third sleeve geometry shown in FIGS. 8-9, it should be appreciated that the docking devices may include other sleeve geometries in place of the third sleeve geometry. For example, the docking devices 400 and/or 500 shown in FIGS. 10-11 and 12-13, respectively, may include two separate and distinct expandable sleeves, such as the first expandable sleeve 230 and second expandable sleeve 232 of FIGS. 6-7. As another example, the expandable sleeves of the docking devices 400 and/or 500 may not be tapered in their intermediate section. For example, the docking device 400 and/or 500 may include the expandable sleeve 104 shown in FIGS. 4-5. Thus, although FIGS. 4-13 illustrate specific pairings of exemplary coil and sleeve geometries, it should be appreciated that these coil and/or sleeve geometries may altered, varied, and/or used in different combinations than those shown in FIGS. 4-13.

Further, it should be appreciated that, apart from the first portion of the second section, the coils of the docking devices (100, 200, 300, 400, 500), may have substantially the same geometry. That is, the first section, and second and third portions of the second section of the coils may be substantially the same size and/or shape. Thus, the description of these portions of the coil 102 (i.e., first section 110, second portion 122 and third portion 124) of docking device 100 may apply equally to the similarly numbered portions of the coils 202, 302, 402, and/or 502. Similarly, apart from the intermediate section (which is tapered or non-existent in the docking devices of FIGS. 6-13), the expandable sleeve may have substantially the same geometry. Thus, other geometries of the expandable sleeve 104 shown and described in FIGS. 4-5, such as the overall length of the expandable sleeve (angular length from the first end 126 to the second end 128 of the expandable sleeve 104), the maximum thickness of the expandable sleeve 104, the taper at the second end 128 of the expandable sleeve, etc., may apply equally to the expandable sleeves 204, 304, 404, and/or 504.

Figure 14:
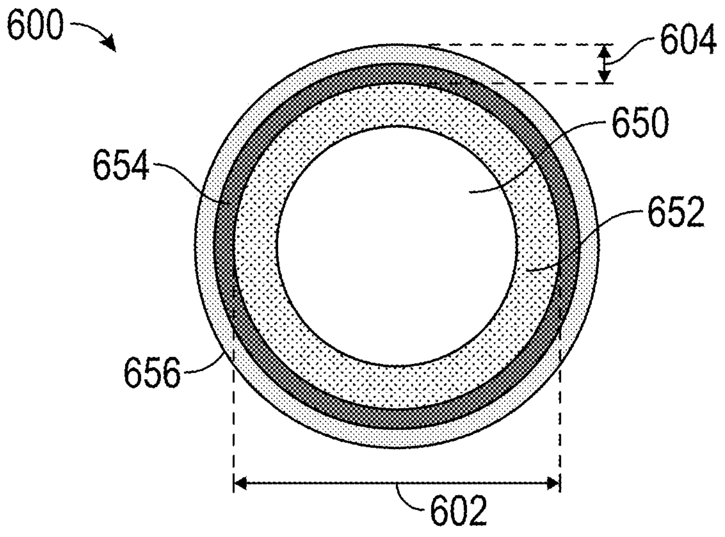
FIG. 14 illustrates a cross-sectional view of any one of the exemplary docking devices of FIGS. 3-13 taken along the line A-A where an expandable sleeve of the docking device is in a compressed position, such as when the docking device is retained within a docking device delivery apparatus, prior to implantation.
Figure 15:
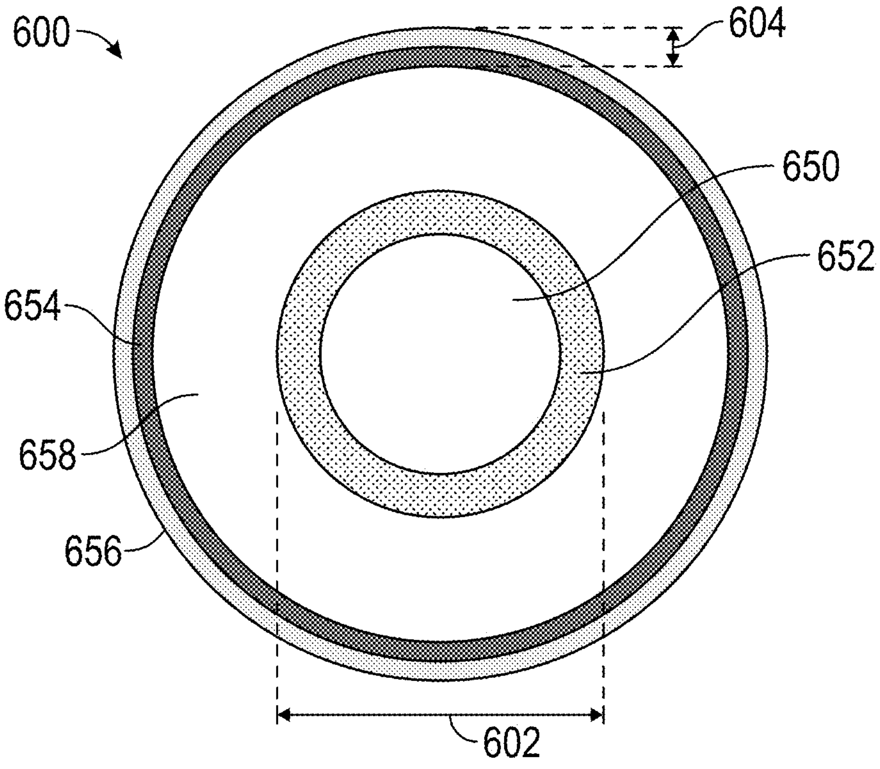
FIG. 15 illustrates a cross-sectional view of any one of the exemplary docking devices of FIGS. 3-13 taken along cutting plane A-A where the expandable sleeve of the docking device is in an expanded position, such when the docking device has been ejected from the docking device delivery apparatus, after implantation.

FIGS. 14-15 depict cross-sectional views of a docking device 600 (which may comprise any one or more of the docking devices 100, 200, 300, 400, and/or 500 shown in FIGS. 4-13) taken along cutting plane A-A shown in FIGS. 5, 7, 9, 11, and 13. Specifically, FIG. 14 depicts an expandable sleeve of the docking device 600 is in a compressed position (radially compressed and axially elongated) and FIG. 15 depicts the expandable sleeve is in an expanded position (radially expanded and axially shortened). As explained above, the expandable sleeve may be in the compressed position when the docking device 600 is still retained within a docking device delivery apparatus (e.g., docking device delivery apparatus 18 described above) and/or prior to retraction of a sleeve shaft (e.g., sleeve shaft 34 described above). The expandable sleeve may radially expand to the expanded position after being ejected from the docking device delivery apparatus and/or after removal of a crimping pressure (such as after retraction of the sleeve shaft), one or both of which may occur during and/or after implantation and/or deployment of the docking device 600.

The docking device 600 may comprise one or more components that are generally similar to one or more components of the docking devices 100, 200, 300, 400, and 500. Thus, for conciseness, the components of the docking device 600 that are similar to the components of the docking devices 100, 200, 300, 400, and 500 are labeled similarly and may not include additional description. Specifically, the docking device 600 comprises a coil 602 and an expandable sleeve 604, (corresponding to the coil 102, coil 202, coil 302, coil 402, and/or coil 502 and the expandable sleeve 104, expandable sleeve 204, expandable sleeve 304, expandable sleeve 404, and/or expandable sleeve 504, of the docking devices 100, 200, 300, 400, and/or 500, respectively).

In the embodiments of FIGS. 14-15, coil 602 comprises a core 650 and optionally includes a first cover 652, and the expandable sleeve 604 comprise an expandable member 654 and optionally includes a second cover 656.

Core 650 may comprise a shape memory material (e.g., Nitinol) that is configured to return from a temporary deformed shape (e.g., unwound configuration) to an original permanent shape (e.g., coiled configuration) responsive to a stimulus (e.g., temperature change, electric current, electromagnetic radiation, mechanical stress, etc.) and/or when not constrained by a delivery shaft of the docking device delivery apparatus (e.g., delivery shaft 20 described above). As explained above, the core 650 may be initially set, formed, and/or other constructed to have a generally coiled configuration, such as any one or more of the coiled geometries shown above in FIGS. 4-13. The shape-memory material may comprise a shape-memory alloy (e.g., Nitinol) and/or shape-memory polymer.

First cover 652 may radially surround and/or cover the core 650, as illustrated in FIGS. 14-15 and may be configured to provide cushioning and/or padding between the core 650 and the expandable member 654 to protect the core 650. In some embodiments, the first cover 652 may cover and/or surround an entire length of the core 650 (from the first end to the second end of the coil 602). However, in other embodiments the first cover 652 may cover only selected portion(s) of the core 650. In some embodiments, the first cover 652 may be formed of and/or constructed from various native and/or synthetic materials. In one particular embodiment, the first cover may be formed of and/or constructed from an expanded polytetrafluoroethylene (ePTFE).

As described above, the expandable sleeve 604, may be configured to radially expand to provide an enhanced seal between the prosthetic heart valve and the native valve tissue to reduce and/or prevent paravalvular leakage. Specifically, the expandable sleeve 604 may be configured to expand to cover and/or fill any openings in the leaflets of the native heart valve that may exist around the edges of the prosthetic heart valve.

Expandable member 654 may comprise a shape memory material (e.g., Nitinol, memory foam, etc.) that is configured to return from a temporary deformed shape (e.g., compressed position) to an original permanent shape (e.g., expanded position) responsive to a stimulus (e.g., temperature change, electric current, electromagnetic radiation, mechanical stress, etc.) and/or when not subjected to a crimping pressure (e.g., when a sleeve shaft (e.g., sleeve shaft 34 described above) of the docking device delivery apparatus is removed from the expandable member 654). For example, and as explained above, the expandable member 654 may be initially set, formed, and/or other constructed to be in the expanded position (shown in FIG. 15), but may be radially compressed and axially elongated to a compressed position (shown in FIG. 14), to, for example, fit inside the docking device delivery apparatus. When released from the docking device delivery apparatus however, the expandable member 654 is configured to radially expand and axially shorten to the expanded position. In this way, a gap 658 may form between the expandable member 654 and the coil 602 when the expandable member 654 radially expands away from the coil 602, as is illustrated in FIG. 15.

In some embodiments, the expandable member 654 may comprise a braided structure, such as a braided wire mesh or lattice. For example, the expandable member 654 may have a braided structure containing a metal alloy with shape memory properties, such as Nitinol. In another embodiment, the expandable member 654 may comprise a foam structure. For example, the expandable member may include an expandable memory foam which can expand to a specific shape or specific pre-set shape upon removal of a crimping pressure (e.g., upon removal of the sleeve shaft of the docking device delivery apparatus).

Second cover 656 may radially surround and/or cover the expandable member 654, as illustrated in FIGS. 14-15, and may be configured to directly physically contact the native heart valve tissue (e.g., native leaflets) and/or the prosthetic heart valve to provide a seal between the prosthetic heart valve and the native heart valve tissue and thereby reduce paravalvular leakage around the prosthetic heart valve.

In some embodiments, the second cover 656 may be configured to be atraumatic to native tissue and/or may be configured to promote tissue ingrowth into the second cover 656 to further enhance the seal between the prosthetic heart valve and the native heart valve tissue. For example, the second cover 656 may have pores to encourage tissue ingrowth. In another example, the second cover 656 may be impregnated with growth factors to stimulate or promote tissue ingrowth, such as transforming growth factor alpha (TGF-alpha), transforming growth factor beta (TGF-beta), basic fibroblast growth factor (bFGF), vascular epithelial growth factor (VEGF), and/or combinations thereof.

The one or more of the expandable member 654, the second cover 656, and/or the first cover 652 may be coupled to the core 650 via suitable coupling means such as one or more of textured surface resistance, suture, glue, and thermal bonding. In some embodiments, the expandable member 654, the second cover 656 and/or the first cover 652 may be sewn to the core 650 via sutures. In some embodiments, the expandable member 654, the second cover and/or the first cover 652 may be coated, sprayed, dipped, and/or laminated onto the core 650. For example, the first cover 652 and/or the second cover 656 may comprise a sprayed, dipped, and/or laminated thermoplastic polyurethane.

The second cover 656 may be formed of and/or constructed from any suitable material, including foam, cloth, fabric, and/or polymer, that is flexible enough to allow for compression and expansion of the expandable member 654 and/or that promotes tissue ingrowth into the second cover 656. For example, the second cover 656 can include a fabric layer constructed from a thermoplastic polymer material, such as polyethylene terephthalate (PET). Thus, the second cover 656 may be configured to elastic enough to allow the expandable member 654 to move between the radially compressed (and axially elongated) state to the compressed position and the expanded position. In this way, the entire expandable sleeve 604 (including the expandable member 654 and the second cover 656 move between the compressed position and the expanded position.

In some embodiments, the expandable cover 654 and/or the second cover 656 may be coupled to the core 650 at their distal end(s). In some such embodiments, the proximal end(s) of the expandable member 654 and/or the second cover 656 may not be directly coupled to the core 650 and may be free to slide axially relative to the core 650. In this way, the proximal end(s) of the expandable member 654 and/or the second cover 656 may move axially towards the distal end(s) of the expandable member 654 and/or the second cover 656 as the expandable sleeve 604 radially expands and axially contracts when moving from the compressed position to the expanded position, such as during deployment of the expandable sleeve 604.

When the expandable sleeve 604 is in the compressed position (FIG. 14) the expandable member 654 may directly physically contact the first cover 652 surrounding the core 650 such that no gap or cavity exists between the first cover 652 (and/or the core 650) and the expandable member 654, as shown in FIG. 14. However, when the expandable sleeve radially expands and axially shortens to the compressed position (such as after the sleeve shaft of the docking device delivery apparatus is removed from the expandable sleeve 604) a gap or cavity 658 may be created between the first cover 652 and the expandable member 654, as shown in FIG. 15.

When in the expanded position, the expandable sleeve 604 (e.g., second cover 656) may be configured to directly physically contact the prosthetic heart valve and/or the leaflets of the native heart valve. For example, a portion of the expandable sleeve 604 that is configured to be positioned on the outflow (e.g., ventricular) side of the native heart valve may directly physically contact the outflow side of the native heart valve leaflets (e.g., the ventricular side of an anterior leaflet of a native mitral valve). Additionally or alternatively, a portion of the expandable sleeve 604 that is configured to be positioned on an inflow (e.g., atrial) side of the native heart valve may directly physically contact the inflow side of the native heart valve leaflets (e.g., the atrial side of a posterior leaflet of a native mitral valve) and/or an outwardly-facing surface of a prosthetic heart valve that is disposed within the docking device 600. For example, an outwardly-facing surface of the atrial portion of the expandable sleeve 604 may directly physically contact the inflow side of the native heart valve leaflet(s), while an opposite inwardly-facing surface of the atrial portion of the expandable sleeve 604 may directly physically contact the outwardly-facing surface of the prosthetic heart valve.

In some embodiments, the docking device 600 can include at least one radiopaque marker (not shown) configured to provide visual indication about the location and/or the amount of radial expansion of the docking device 600 (e.g., when a prosthetic valve is subsequently deployed in the docking device 600) under fluoroscopy. In one embodiment, one or more radiopaque markers (not shown) can be placed on the core 650. In another embodiment, one or more radiopaque markers (not shown) can be placed on the first cover 652, the expandable member 654, and/or the second cover 656.

Exemplary Docking Device Implanted at a Native Mitral Valve

Figure 16:
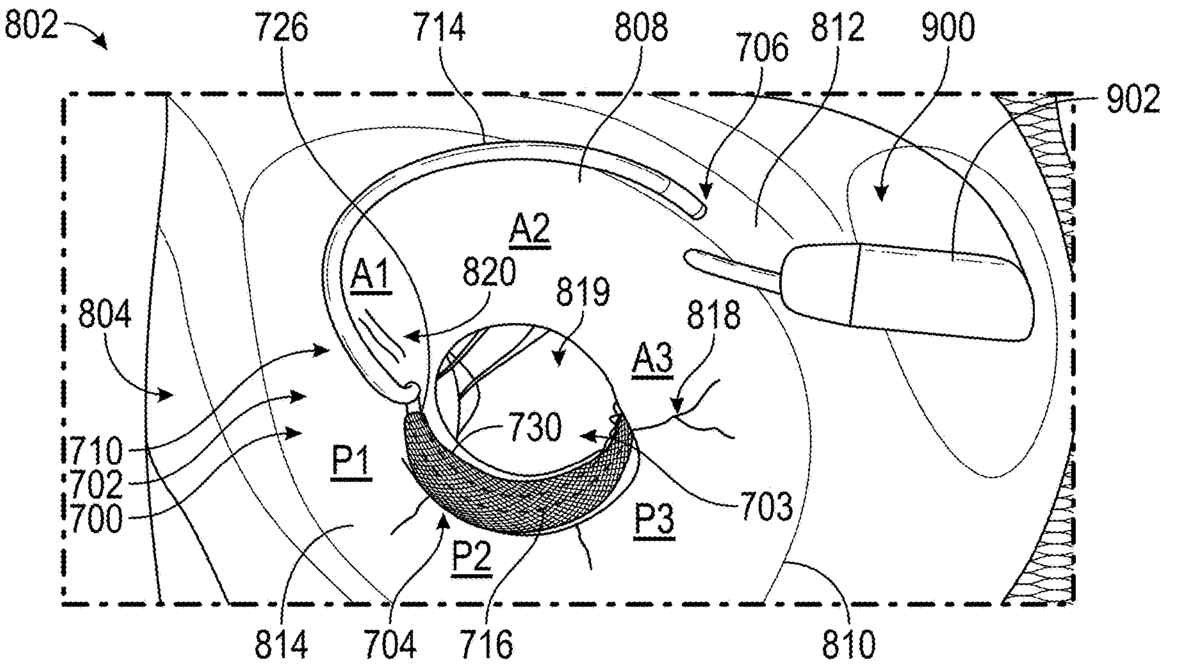
FIG. 16 illustrates an internal perspective view of a bottom portion of a left atrium of a heart, including the atrial side of a mitral valve, where an exemplary docking device has been implanted at the mitral valve.
Figure 17:
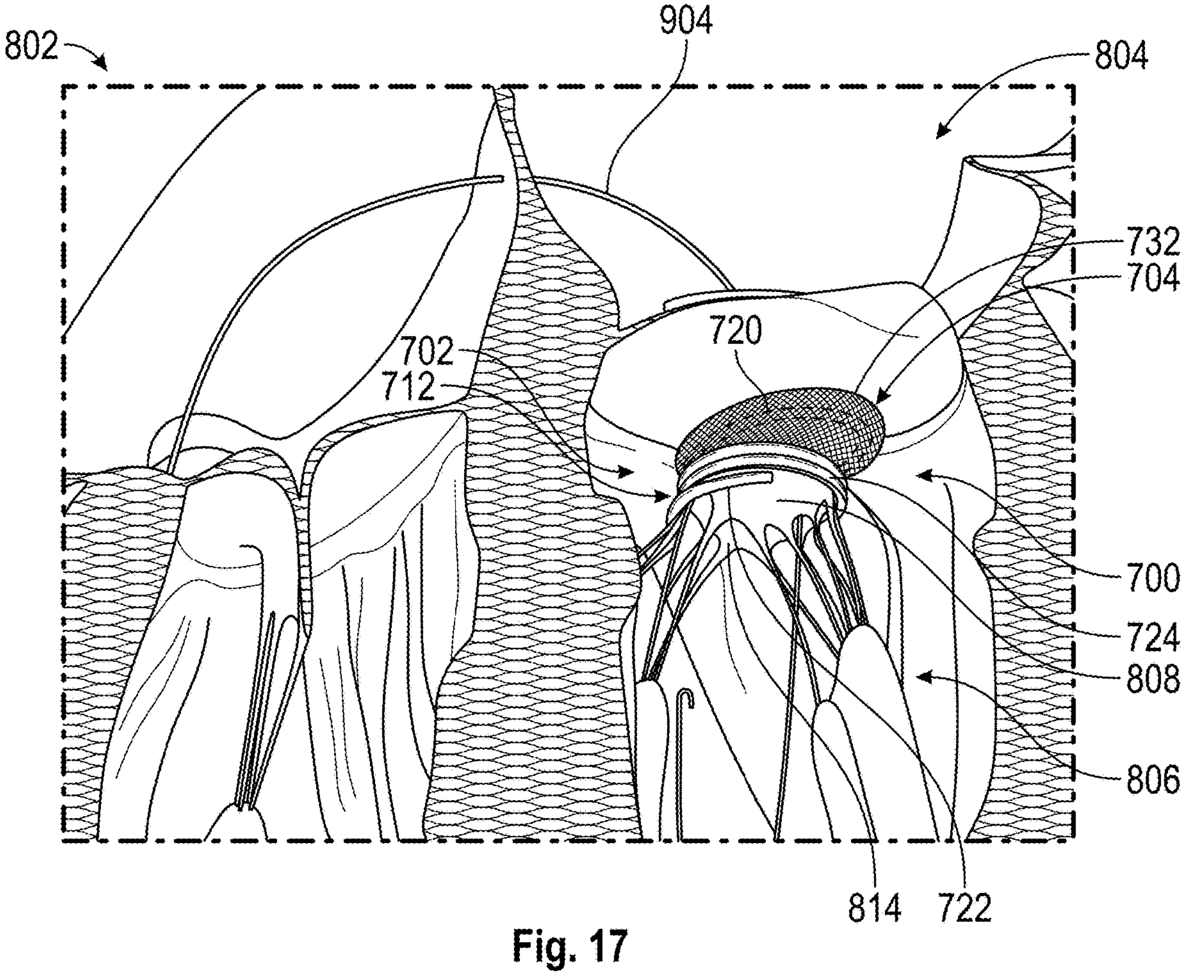
FIG. 17 illustrates an internal perspective view of the heart of FIG. 16, with the docking device of FIG. 16 implanted at the mitral valve.
Figure 18:
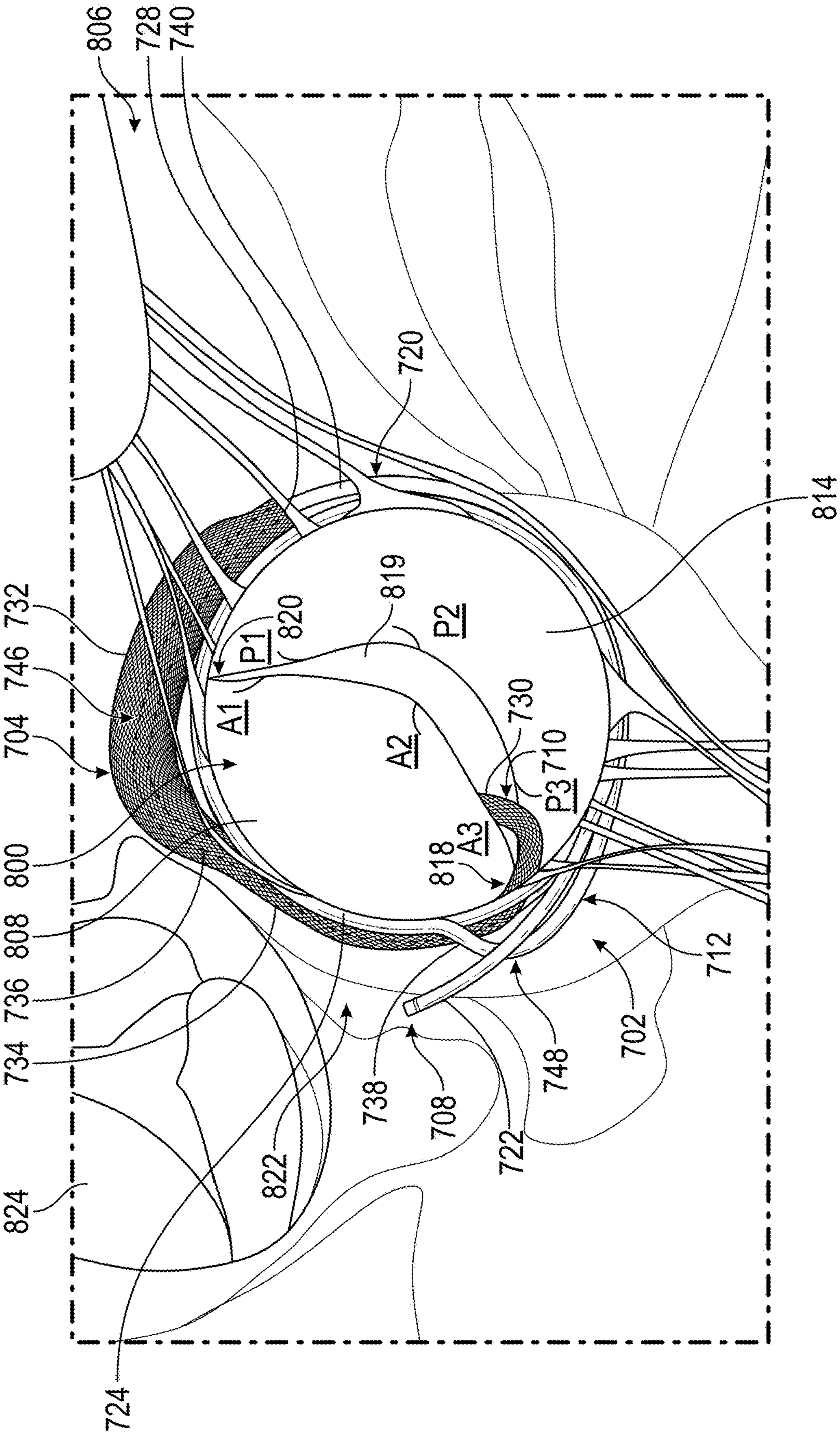
FIG. 18 illustrates an internal perspective view of a top portion of a left ventricle of the heart of FIGS. 16-17, including the ventricular side of the mitral valve with the docking device of FIGS. 16-17 implanted at the mitral valve.

FIGS. 16-18 depict a docking device 700 implanted at a native mitral valve 800 of a heart 802 in a deployed configuration. Specifically, a docking device delivery apparatus 900, and more specifically a delivery shaft 902 of the docking device delivery apparatus, has implanted and deployed the docking device 700 in FIG. 16 and is in the process of retracting away from the docking device 700. FIG. 17 depicts the docking device 700 after the docking device delivery apparatus 900 has been fully removed from the heart 802, and only a guidewire 904 remains in the heart 802.

Docking device 700 may comprise one or more components that are generally similar to one or more components of the docking device 500. Thus, for conciseness, the components of the docking device 700 that are similar to the components of the docking device 500 are labeled similarly and may not include additional description. For example, the docking device 700 comprises a coil 702 and an expandable sleeve 704, and the coil 702 comprises a first section 710 that is configured to be positioned on an inlet side of a native heart valve (e.g., on the atrial side of a mitral valve) and a second section 712 that is configured to be positioned on an outlet side of a native heart valve (e.g., on the ventricular side of a mitral valve), corresponding to the coil 502, the expandable sleeve 504, the first section 510, and the second section 512, respectively, of the docking device 500.

FIG. 16 depicts a perspective view of the docking device 700 from a superior position relative to the mitral valve 800 (and thus looking down on the mitral valve 800), within left atrium 804 of the heart 802. FIG. 17 depicts a perspective view of the heart 802 showing the docking device 700 implanted and deployed at the mitral valve 800 such that it wraps around the ventricular side of the leaflets of the mitral valve 800. FIG. 18 depicts a perspective view of a left ventricle 806 of the heart 802 from an inferior position below the mitral valve 800, looking up at the mitral valve 800.

As illustrated in FIG. 16, the first portion 714 of the first section 710 of the coil 702 of the docking device 700 is configured to extend radially outwardly on an atrial side of an anterior leaflet 808 of the mitral valve 800, towards an edge 810 of the mitral valve 800. In some embodiments, the first portion 714 extends beyond the edge 810 of the mitral valve 800 onto a shelf 812 or other native heart tissue that surrounds and/or is directly adjacent to the mitral valve 800. Expandable sleeve 704 covers the second portion 716 of the first section 710 of the coil 702 and directly physically contacts the atrial side of a posterior leaflet 814 of the mitral valve 800. Coil 702 is configured to cross over from the left atrium 804 to a left ventricle 806 of the heart 802 (i.e., cross over from the atrial side of the mitral valve 800 to the ventricular side of the mitral valve 800) through an opening 819 in the mitral valve 800 that forms between the anterior and posterior leaflets. In some examples, the coil 702 is configured to cross over from the atrial side of the mitral valve 800 to the ventricular side of the mitral valve 800 at and/or near a posteromedial commissure 818 and/or A3/P3 position of the mitral valve 800. Specifically, the junction of the first section 710 and the second section 712 of the coil 702 may be configured to be positioned at where the coil 702 crosses over from the atrial side of the mitral valve 800 to the ventricular side of the mitral valve 800.

Thus, as illustrated in FIGS. 17-18, the first portion 720 of the second section 712 of the coil 702 begins where the coil 702 crosses over to the ventricular side of the mitral valve 800 from the atrial side of the mitral valve 800, extends distally over the ventricular side of the anterior leaflet 808, and then continues over the ventricular side of the posterior leaflet 814. As discussed above, the first portion 720 of the second section 712 of the coil 702 may be configured to extend radially outwards relative to the third portion 724 of the second section 712 of the coil 702 towards an anterolateral commissure 820 and/or A1/P1 position of the mitral valve 800. In some examples, the coil 702 may extend radially outwards towards, to, and/or beyond the anterolateral commissure 820 on the ventricular side of the mitral valve leaflets.

Expandable sleeve 704 may also extend through the opening 819 of the mitral valve 800 between the atrium 804 and the ventricle 806. That is, the expandable sleeve 704 may extend over the coil 702 in the region where the coil 702 crosses over from the atrial side of the mitral valve leaflets to the ventricular side of the mitral valve leaflets. As illustrated in FIG. 18, the intermediate tapered portion 734 of the expandable sleeve 704 may be configured to be positioned at, adjacent to, and/or near a left ventricular outflow tract (LVOT) 822 of the ventricle 806. The LVOT 822 is a conduit for blood to exit the ventricle 806 and connects the ventricle 806 to the aorta. Thus, blood flows through the LVOT 822 to the aorta when the aortic valve 824 opens and/or the ventricle 806 contracts.

Specifically, the intermediate tapered portion 734 may be configured to extend over a portion of the ventricular side of the anterior leaflet 808 that is adjacent to the LVOT 822. For example, the intermediate tapered portion 734 may be configured to extend distally from where the coil 702 and/or expandable sleeve 704 crosses over from the atrial side of the mitral valve 800 to the ventricular side of the mitral valve 800 (e.g., at the posteromedial commissure) over the anterior leaflet 808 towards the anterolateral commissure 820 and/or A1/P1 position. In other examples, the intermediate tapered portion 734 may begin (and the first portion 730 of the expandable sleeve 704 may end) after the expandable sleeve 704 crosses over from the atrial side of the mitral valve leaflets to the ventricular side of the mitral valve leaflets, at a distance from this crossover point. As examples, the intermediate tapered portion 734 may begin at least 5 degrees, at least 10 degrees, at least 15 degrees, at least 20 degrees, at most 60 degrees, at most 50 degrees, at most 40 degrees, at most 30 degrees, at most 20 degrees, and/or at most 10 degrees from where the expandable sleeve 704 crosses over from the atrial side of the mitral valve leaflets to the ventricular side of the mitral valve leaflets (e.g., the posteromedial commissure). By extending the first portion 730 of the expandable sleeve 704 to and/or distally past the A3/P3 position and/or posteromedial commissure and/or by positioning the intermediate tapered portion 734 distally away from the posteromedial commissure and/or A3/P3 position, the expandable sleeve 704 may provide an enhanced seal between the mitral valve tissue and a prosthetic heart valve.

In some embodiments, the intermediate tapered portion 734 may terminate (and the second portion 732 of the expandable sleeve 704 may begin) before reaching the anterolateral commissure 820 and/or A1/P1 position. As examples, the intermediate tapered portion 734 may extend distally at least 10 degrees, at least 20 degrees, at least 30 degrees, at least 40 degrees, at least 50 degrees, at least 60 degrees, at least 80 degrees, at least 90 degrees, at most 170 degrees, at most 160 degrees, at most 150 degrees, at most 140 degrees, at most 130 degrees, at most 120 degrees, at most 110 degrees, at most 100 degrees, at most 90 degrees, at most 80 degrees, at most 70 degrees, and/or at most 60 degrees from the first portion 730 of the expandable sleeve 704 over the ventricular side of the anterior leaflet 808.

By including the intermediate tapered portion 734 at and/or near the LVOT 822, the expandable sleeve 704 may not excessively block, obstruct, and/or otherwise constrict/narrow the LVOT 822, thereby ensuring adequate blood-flow through the LVOT 822 even when the docking device 700 is implanted at the mitral valve 800. In examples where the expandable sleeve includes two separate and distinct sleeves, the gap that separates the two sleeves (e.g., gap 234) may be positioned at the same and/or similar position as the intermediate tapered portion 734, and thus may similarly serve to ensure adequate blood-flow through the LVOT 822.

The second portion 732 of the expandable sleeve 704 is configured to extend distally from the intermediate tapered portion 734 to and/or past the anterolateral commissure 820, anterolateral side of the mitral valve 800, and/or A1/P1 position of the mitral valve 800. As examples, the second portion 732 may extend at least may extend distally at least 10 degrees, at least 20 degrees, at least 30 degrees, at least 40 degrees, at least 50 degrees, at least 60 degrees, at least 80 degrees, at least 90 degrees, at least 100 degrees, at least 110 degrees, at least 120 degrees, at most 180 degrees, at most 170 degrees, at most 160 degrees, at most 150 degrees, at most 140 degrees, at most 130 degrees, at most 120 degrees, at most 110 degrees, at most 100 degrees, at most 90 degrees, at most 80 degrees, at most 70 degrees, and/or at most 60 degrees from the intermediate tapered portion 734 of the expandable sleeve 704 over the ventricular side of the anterior leaflet 808. By extending to and/or past the A1/P1 position and/or anterolateral commissure 820, the expandable sleeve 704 may provide an enhanced seal between the native valve tissue and a prosthetic heart valve, thereby reducing paravalvular leakage around the prosthetic heart valve. Specifically, the expandable sleeve 704 may close openings in the mitral valve 800 near and/or at the A1/P1 position and/or anterolateral commissure 820, thereby reducing paravalvular leakage at and/or near the A1/P1 position and/or anterolateral commissure 820.

In some embodiments, the expandable sleeve 704 may extend radially outwardly from the coil 702. In the embodiments of FIGS. 17-18, the expandable sleeve 704 may extend radially outwardly towards the third portion 724 of the second section 712 of the coil 702 and in some such embodiments, may physically contact the third portion 724 of the second section 712 of the coil 702. However, in some such embodiments, the expandable sleeve 704 may not physically contact the third portion 724 of the coil 702 prior to expansion of the prosthetic valve and may only physically contact the third portion 724 after the prosthetic valve expands within the docking device 700 pushes the third portion 724 of the coil 702 into contact with the expandable sleeve 704. In this way, even though the first portion 720 of the second section 712 of the coil 702 may extend radially outwardly relative to the third portion 724 of the coil 702 (such that is may be separated from the third portion 724 by a radial gap), the expandable sleeve 704 may extend between the first portion 720 and the third portion 724 of the second section 712 of the coil 702 to close and/or seal the radial gap that may exist between these two portions of the coil 702, thereby ensuring that paravalvular leakage does not occur in-between these two portions of the coil 702.

FIGS. 16-18 depict the docking device 700 in a first deployed position (which may also be referred to as "deployed configuration"). As will be discussed in greater detail below with reference to FIGS. 22-25, the docking device 700 is configured to move between the first deployed position and a second deployed position (which may also be referred to as "final assembled configuration" and/or "expanded deployed configuration") when a prosthetic heart valve is expanded within the docking device 700. Thus, the docking device 700 may be in the first deployed position prior to expansion of the prosthetic heart valve and may be in the second deployed position after the prosthetic heart valve has been expanded within the docking device 700. Specifically, the third portion 724 of the docking device 700 is configured to radially expand the docking device 700 moves from the first deployed position to the second deployed position (e.g., when the prosthetic heart valve is expanded within the docking device 700). In some embodiments, the third portion 724 is configured to radially expand until the third portion 724 and the second portion 722 are substantially congruent (as explained above).

As explained above, coil 702 and/or expandable sleeve 704 is/are configured to directly physically contact the native valve leaflets and/or the prosthetic heart valve to provide a seal between the native valve leaflets and the prosthetic heart valve. In particular, when the prosthetic heart valve is expanded within the docking device 700, the coil 702 and/or expandable sleeve 704 is/are configured to sandwich the native valve leaflets between the docking device 700 and the prosthetic heart valve to provide a seal there-between.

Exemplary Prosthetic Heart Valve

Figure 19:
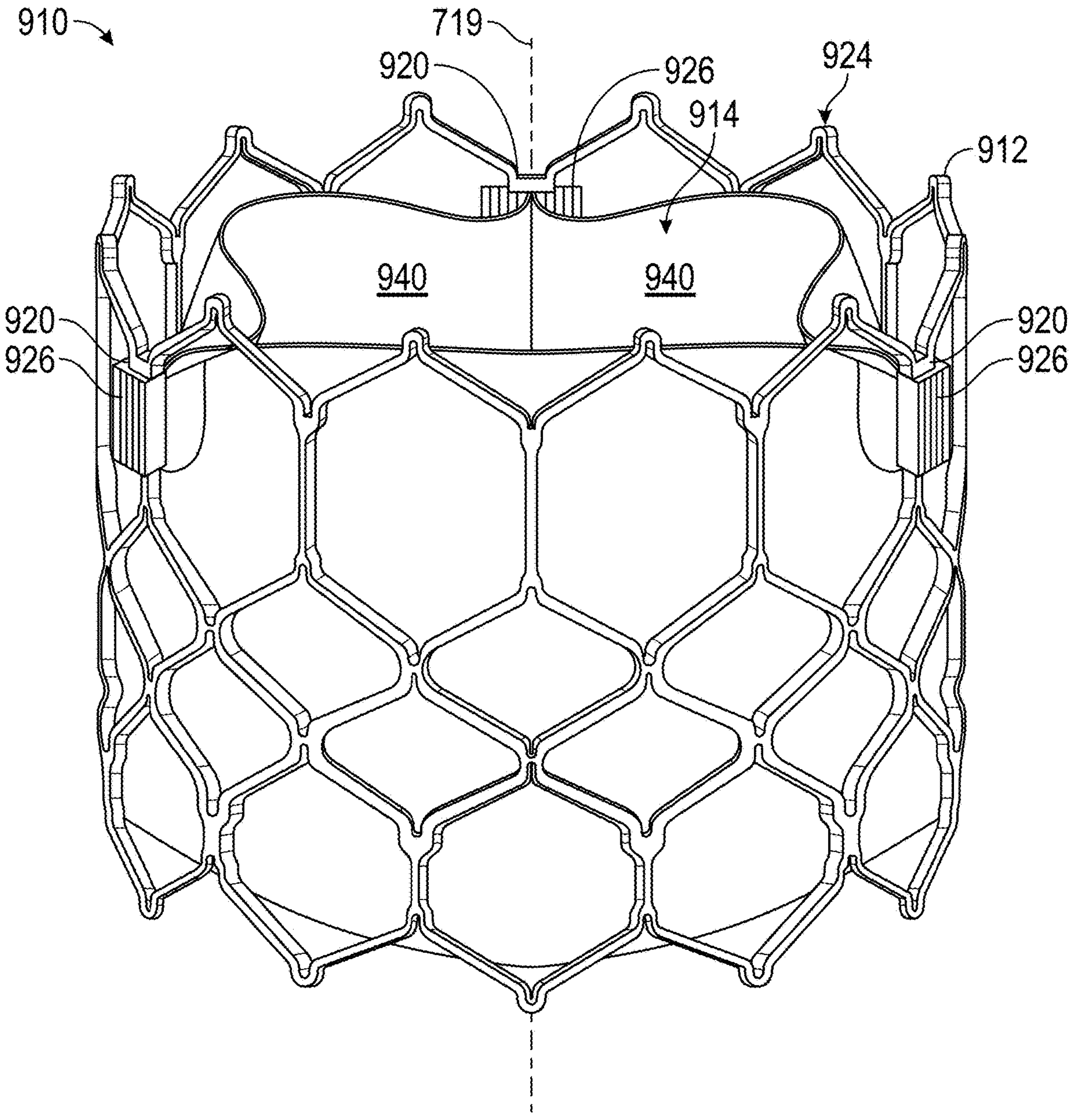
FIG. 19 illustrates a side view of a prosthetic heart valve, according to an embodiment.
Figure 20:
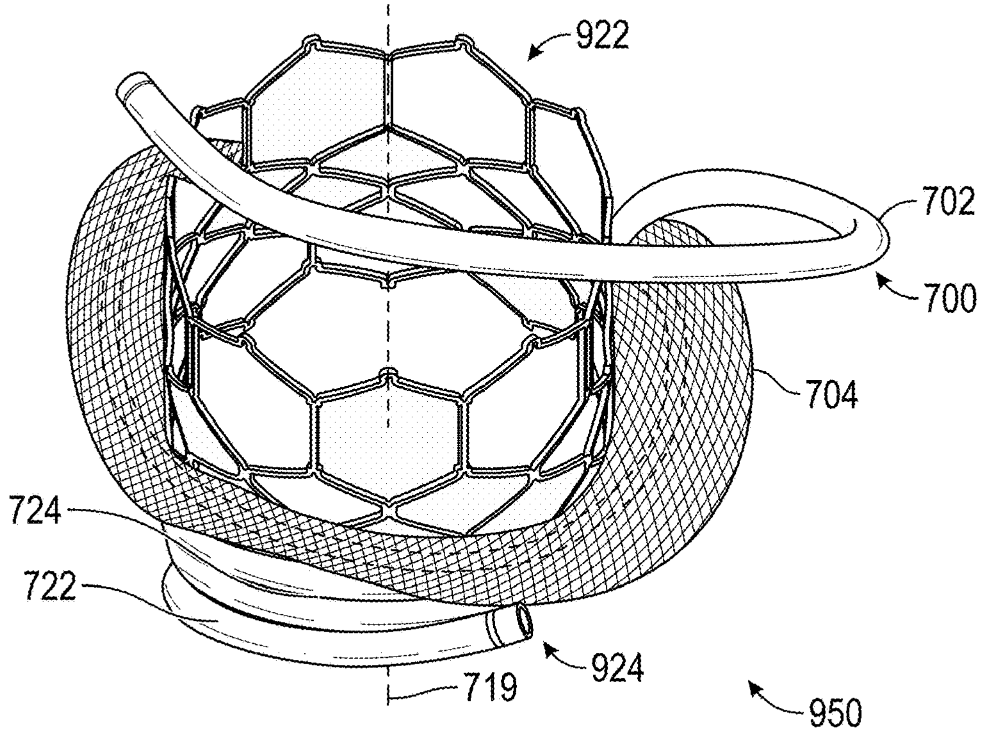
FIG. 20 illustrates a perspective view an exemplary prosthetic heart valve system comprising the docking device of FIGS. 16-18 and the prosthetic heart valve of FIG. 19 received therein.
Figure 21:
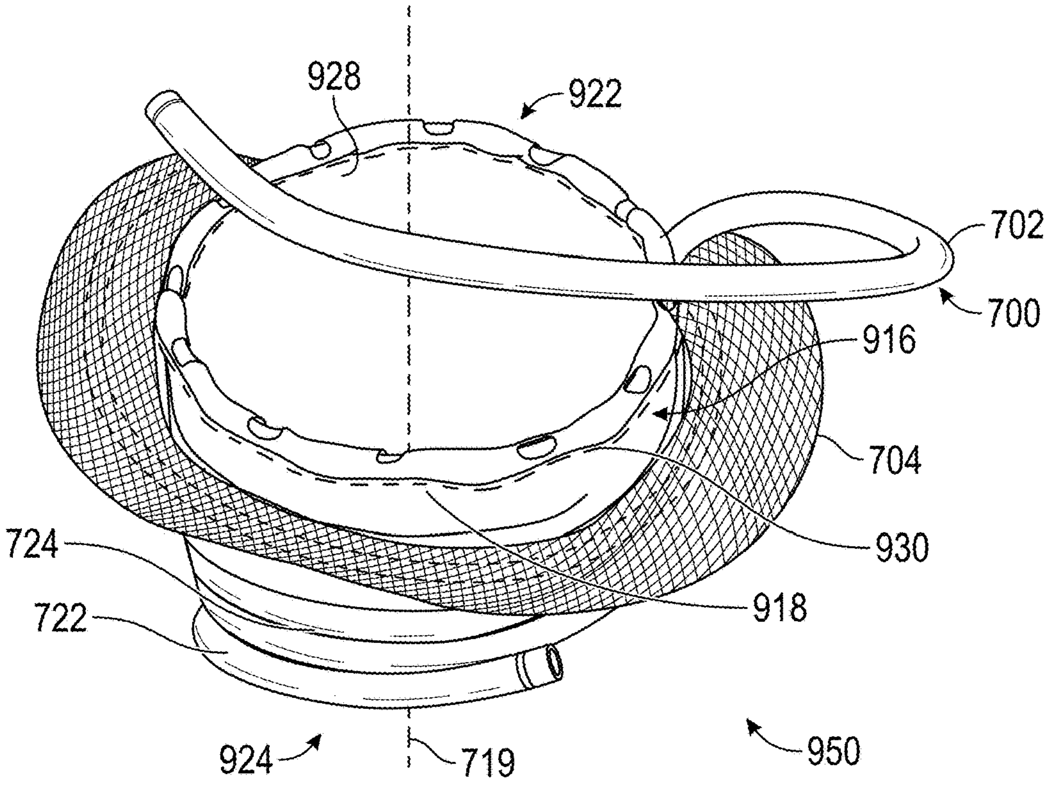
FIG. 21 illustrates a perspective view of the prosthetic heart valve system of FIG. 20, with the prosthetic heart valve of FIGS. 19-20 fully assembled within the docking device.

FIGS. 19-21 depict an exemplary prosthetic heart valve 910 that may be expanded and deployed within a docking device (e.g., docking devices 10, 100, 200, 300, 400, 500, 600, and/or 700 described above). FIG. 19 depicts the prosthetic heart valve 910 on its own, and FIGS. 20-21 depict the prosthetic heart valve 910 deployed within the docking device 700. FIGS. 19-20 depict the prosthetic heart valve 910 without an optional cover, while FIG. 21 depicts the prosthetic heart valve 910 with the optional cover included. Many of the components of the prosthetic heart valve 910 (such as the valvular structure, leaflets, commissures, and/or other valvular components) are omitted in FIGS. 20-21 for simplicity and clarity. Thus, FIGS. 20-21 show simplified representations of the prosthetic heart valve 910, with only the general frame structure shown in FIG. 20, and only the frame structure covered in the optional cover in FIG. 21.

The prosthetic heart valve 910 can include a stent or frame 912, a valvular structure 914 (only shown in FIG. 19), and a valve cover 916 (only shown in FIG. 21). The valvular structure 914 can include three leaflets 940 (only shown in FIG. 19), collectively forming a leaflet structure (although a greater or fewer number of leaflets can be used), which can be arranged to collapse in a tricuspid arrangement. The leaflets 940 are configured to permit the flow of blood from an inflow end 922 to an outflow end 924 of the prosthetic heart valve 910 and block the flow of blood from the outflow end 924 to the inflow end 922 of the prosthetic heart valve 910. The leaflets 940 can be secured to one another at their adjacent sides to form commissures 926 (only shown in FIG. 19) of the leaflet structure. The leaflets 940 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The frame 912 can be formed with a plurality of circumferentially spaced slots, or commissure windows 920 (three in the illustrated embodiment of FIG. 19) that are adapted to mount the commissures 926 of the valvular structure 914 to the frame. The frame 912 can be made of any of various suitable plastically expandable materials (e.g., stainless steel, etc.) or self-expanding materials (e.g., Nitinol) as known in the art. When constructed of a plastically expandable material, the frame 912 (and thus the prosthetic heart valve 910) can be crimped to a radially compressed state on a delivery apparatus and then expanded inside a patient by an inflatable balloon or equivalent expansion mechanism. When constructed of a self-expandable material, the frame 912 (and thus the prosthetic heart valve 910) can be crimped to a radially compressed state and restrained in the compressed state by insertion into a sheath or equivalent mechanism of a delivery apparatus. Once inside the body, the prosthetic heart valve 910 can be advanced from the delivery sheath, which allows the prosthetic heart valve 910 to expand to its functional size.

Suitable plastically expandable materials that can be used to form the frame 912 include, without limitation, stainless steel, a nickel-based alloy (e.g., a cobalt-chromium or a nickel-cobalt-chromium alloy), polymers, or combinations thereof. In particular embodiments, frame 912 can be made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form the frame 912 can provide superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

For illustrative purposes, FIG. 21 depicts the cover 916 covering the entire frame 912. However, it should be appreciated that the cover 916 may, in some embodiments, cover only a portion of the frame 912. In the embodiment illustrated in FIG. 21, the valve cover 916 can include an outer portion 918 which can cover an entire outer surface of the frame 912. In some embodiments, the valve cover 916 can also include an inner portion 928 which can cover an entire inner surface of the frame 912, or alternatively, cover only selected portions of the inner surface of the frame 912. The valve cover 916 can be affixed to the frame 912 by a variety of means, such as via sutures 930 (only shown in FIG. 21).

The valve cover 916 may be configured to directly physically contact the native valve leaflets and/or a docking device (e.g., docking device 700) to provide a seal between the native valve leaflets and the prosthetic heart valve 910. Moreover, the valve cover 916 may be configured to prevent paravalvular leakage between the prosthetic heart valve 910 and the native valve, to protect the native anatomy, to promote tissue ingrowth, among some other purposes. For mitral valve replacement, due to the general D-shape of the mitral valve and relatively large annulus compared to the aortic valve, the valve cover 916 can act as a seal around the prosthetic heart valve 910 (e.g., when the prosthetic heart valve 910 is sized to be smaller than the annulus) and allows for smooth coaptation of the native leaflets against the prosthetic heart valve 910.

In various embodiments, the valve cover 916 can include a material that can be crimped for transcatheter delivery of the prosthetic heart valve 910 and is expandable to prevent paravalvular leakage around the prosthetic heart valve 910. Examples of possible materials include foam, cloth, fabric, one or more synthetic polymers (e.g., polyethylene terephthalate (PET), polytetrafluoroethylene (PTFE), ePTFE, etc.), organic tissues (e.g., bovine pericardium, porcine pericardium, equine pericardium, etc.), and/or an encapsulated material (e.g., an encapsulated hydrogel).

In certain embodiments, the valve cover 916 can be made of a woven cloth or fabric possessing a plurality of floated yarn sections (e.g., protruding or puffing sections, also referred to as "floats" hereinafter). Details of exemplary covered valves with a plurality of floats are further described in U.S. Publication No. 2019/0374337 and U.S. Pat. Nos. 11,013,600 and 11,013,595, which are incorporated by reference herein in their entireties.

Further details of the prosthetic heart valve 910 and its components are described, for example, in U.S. Pat. Nos. 9,393,110 and 9,339,384, which are incorporated by reference herein. Additional embodiments of the valve cover are described in International Publication No. WO 2020/247907.

Exemplary Prosthetic Heart Valve System

As illustrated in FIGS. 20-21, the prosthetic heart valve 910 can be deployed within a docking device (e.g., the docking device 700) to form a prosthetic heart valve system 950 (which may also be referred to herein as "prosthetic heart valve assembly 950"). Specifically, the prosthetic heart valve 910 can be radially expanded and securely anchored within the docking device 700. Thus, prosthetic heart valve system 950 comprises the prosthetic heart valve 910 and the docking device 700. In some embodiments, the prosthetic heart valve 910 is positioned within the lumen 703 of the docking device 700.

FIGS. 20-21 depict the prosthetic heart valve 910 after it has been fully expanded within the docking device 700. Thus, in FIGS. 20-21, the docking device 700 is in the second deployed position and the third portion 724 of the coil 702 has radially expanded such that it is substantially congruent with the second portion 722. That is, the third portion 724 may have a larger diameter in the second deployed position illustrated in FIGS. 20-21 than when in the first deployed position illustrated in FIGS. 16-18.

However, even when in the final assembled configuration (as in FIGS. 20-21), the first portion 720 of the coil 702 may still comprise a different geometry than the third portion 724 when viewed in a plane perpendicular to the longitudinal axis 719. In some embodiments, the first portion 720 may comprise a different shape than the third portion 724 when in the final assembled configuration. For example, the third portion 724 may be circular when viewed in the plane perpendicular to the longitudinal axis 719 and the first portion 720 may be non-circular when viewed in the plane perpendicular to the longitudinal axis 719, such as one or more of elliptical, D-shaped, and/or crescent-shaped.

In some embodiments, the first portion 720 may still be larger than the third portion 724 even when the coil 702 is in the final assembled configuration. For example, the first portion 720 may extend radially outwardly beyond the third portion 724 when the coil 702 is in the final assembled configuration. Specifically, the corners 746 and/or 748 may remain radially spaced outwardly and away from the third portion 724 in the final assembled configuration. As another example, the cross-sectional area defined by the first portion 720 (in a plane perpendicular to the longitudinal axis 719) may be at least 2%, at least 3, at least 4%, at least 5%, at least 10%, east least 15%, at least 20%, at least 25%, at least 30%, at least 40%, at least 50%, at least 60%, at least 70%, at least 85%, at least 100%, at least 150%, at least 200%, at least 250%, at least 300%, at most 1000%, at most 600%, at most 500%, at most 400%, at most 300%, at most 200%, at most 100%, at most 75%, at most 50%, and/or at most 25% larger than the cross-sectional area defined by the third portion 524 when the docking device 700 is in the final assembled configuration.

In some embodiments, the prosthetic heart valve 910 may be coupled to the docking device 700. For example, the prosthetic heart valve 910 may be locked in the expanded position and may be coupled to the prosthetic heart valve 910 via frictional forces between the native heart valve tissue and the prosthetic heart valve 910 and the docking device 700. Additionally or alternatively, the prosthetic heart valve 910 may be coupled to the docking device 700 after the prosthetic heart valve 910 has been expanded within the docking device 700 via one or more suitable coupling mechanisms such as sutures, fasteners, adhesives, etc.

Although prosthetic heart valve 910 is shown in FIGS. 20-21 as being expanded within docking device 700, it should be appreciated that the prosthetic heart valve 910 may be expanded within any of the other docking devices described herein (e.g., docking devices 10, 100, 200, 300, 400, 500, and/or 600).

Exemplary Prosthetic Heart Valve System Implanted at the Native Mitral Valve

Figure 22:
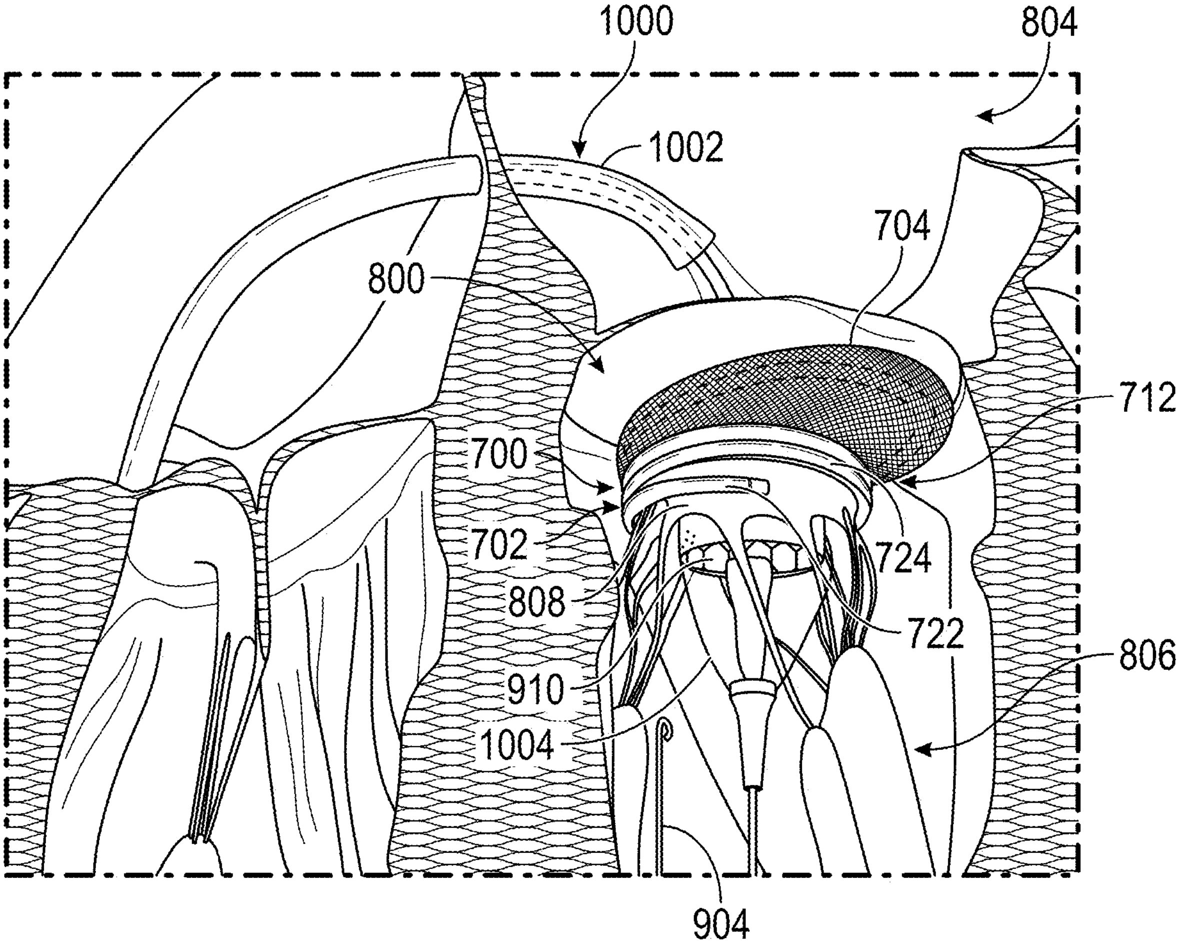
FIG. 22 illustrates a perspective view of the heart of FIGS. 16-18 with the prosthetic heart valve system of FIGS. 20-21, where the prosthetic heart valve of FIGS. 19-21 is being implanted and expanded within the docking device of FIGS. 16-18.
Figure 23:
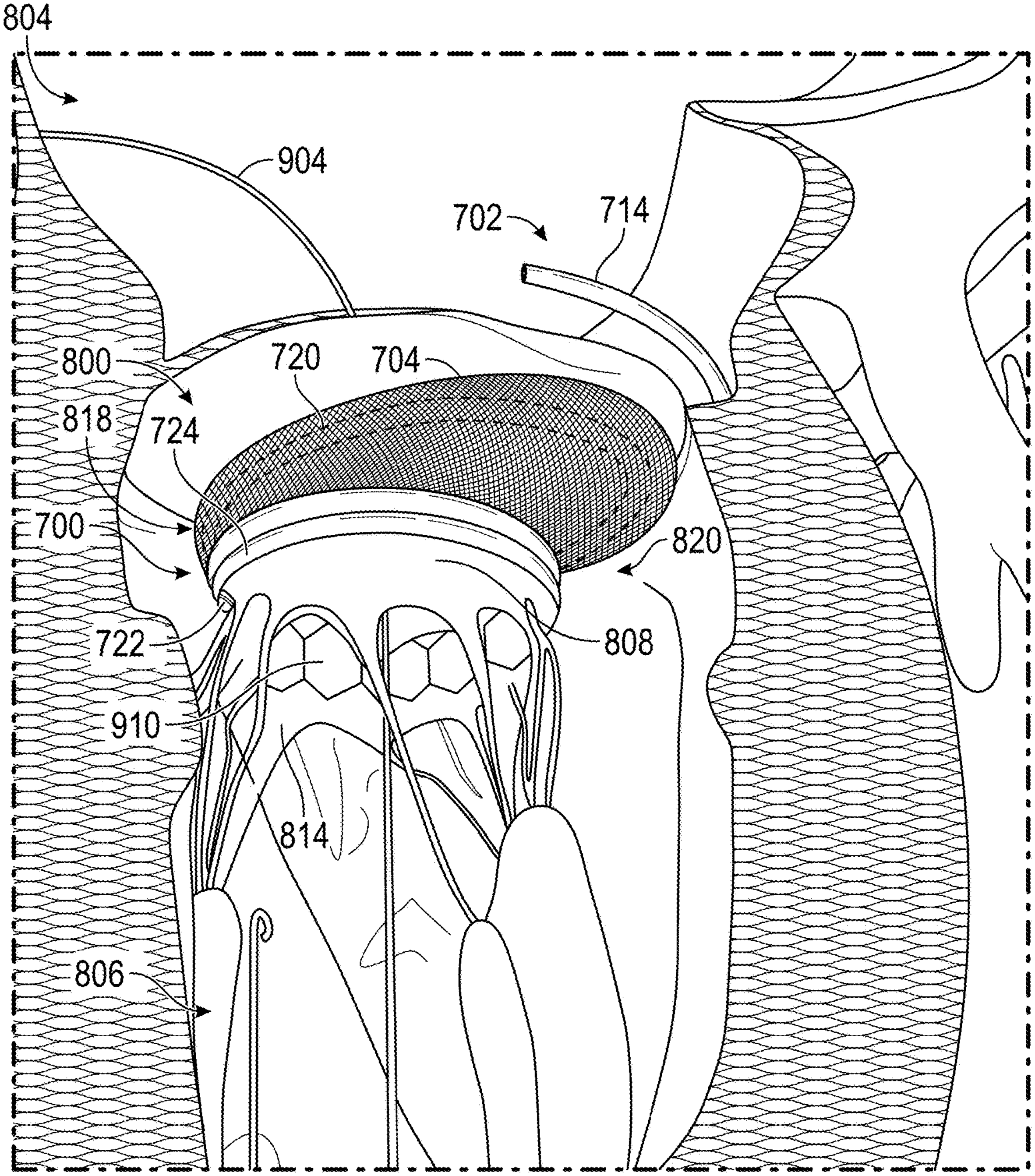
FIG. 23 illustrates a perspective view of the heart of FIGS. 16-18 and 22, after the prosthetic heart valve has been fully expanded and assembled within the docking device at the mitral valve.
Figure 24:
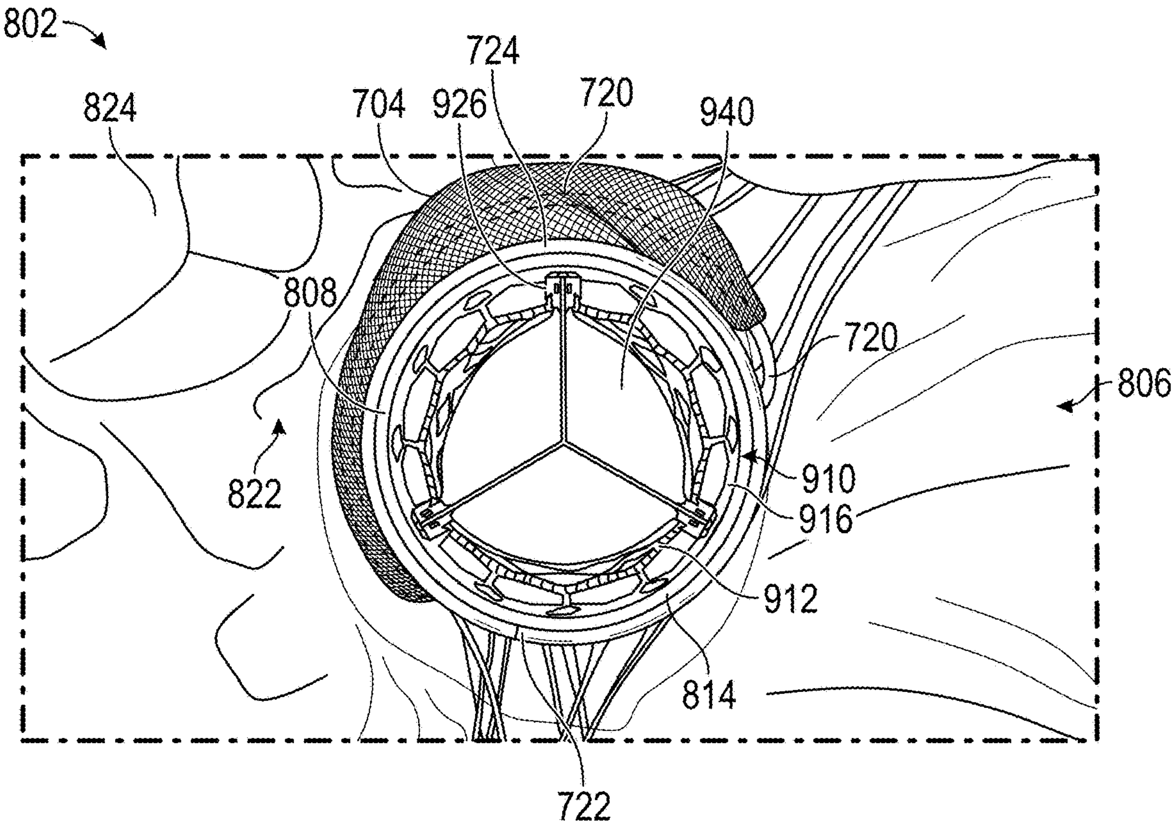
FIG. 24 illustrates an internal perspective view of the top portion of the left ventricle of the heart of FIGS. 16-18 and 22-23, after the prosthetic heart valve has been fully expanded and assembled within the docking device at the mitral valve.
Figure 25:
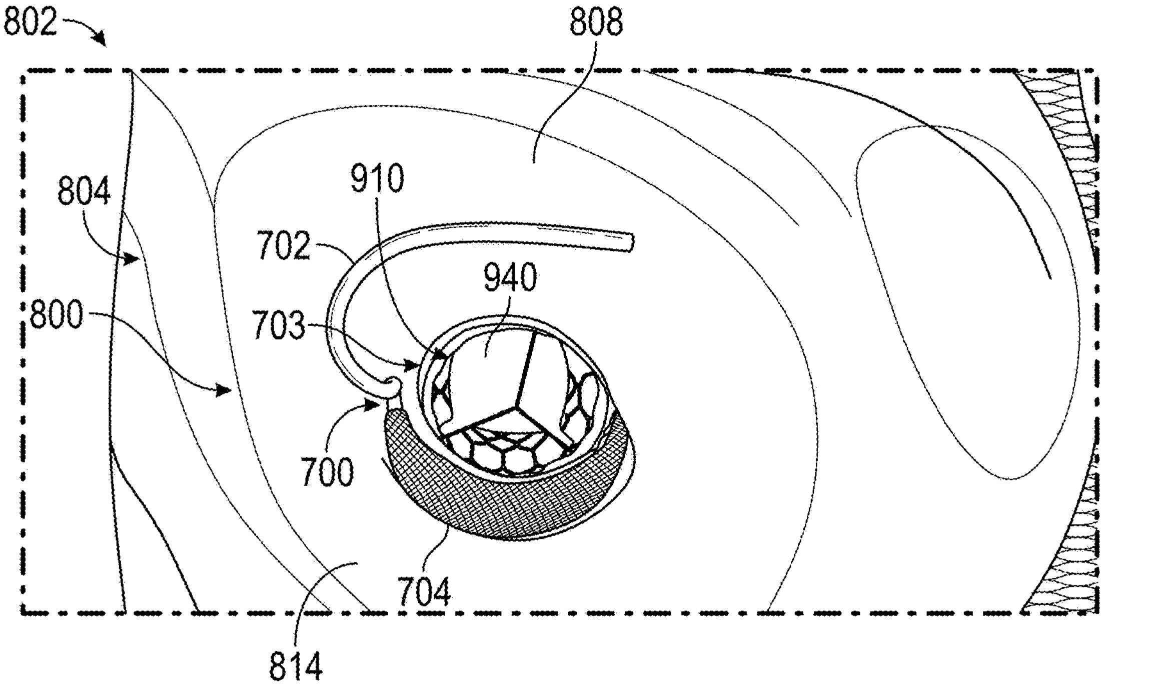
FIG. 25 illustrates an internal perspective view of the bottom portion of the left atrium of the heart of FIGS. 16-18 and 22-24, including the atrial side of the mitral valve, after the prosthetic heart valve has been fully expanded and assembled within the docking device at the mitral valve.

FIGS. 22-25 depict the prosthetic heart valve system 950 implanted at the native mitral valve 800. Specifically, FIG. 22 shows the prosthetic heart valve 910 only partially expanded within the within the docking device 700 at the native mitral valve 800, and FIGS. 23-25 depict the prosthetic heart valve 910 in its fully expanded (functional) position within the docking device 700.

FIG. 22 depicts the prosthetic heart valve 910 being expanded within the docking device 700. In FIG. 22, the prosthetic heart valve 910 has already been delivered to and positioned within the docking device 700 by a prosthetic heart valve delivery apparatus 1000 (e.g., prosthetic heart valve delivery apparatus 58 described above). The prosthetic heart valve 910 may be mounted on a distal end of a delivery shaft 1002 (e.g., delivery shaft 60 described above) of the prosthetic heart valve delivery apparatus 1000, and in FIG. 22, is in the process of being expanded by an inflatable balloon 1004 of the prosthetic heart valve delivery apparatus 1000. Thus, the prosthetic heart valve 910 is in a partially expanded position in FIG. 22, between its compressed position and its fully expanded (functional) position.

The prosthetic heart valve 910 and the second section 712 of the docking device 700 are configured to be positioned on opposite sides of the mitral valve leaflets, in effect sandwiching the mitral valve leaflets there-between. Specifically, the prosthetic heart valve 910 is configured to be positioned on the atrial side of the mitral valve leaflets, while the second section 712 of the coil 702 of the docking device 700 is configured to be positioned on the ventricular side of the mitral valve leaflets. The first section 710 of the coil 702 is configured to be positioned on the atrial side of the mitral valve leaflets and thus may directly physically contact the atrial side of the mitral valve leaflet(s) and/or the exterior-facing surface of the prosthetic heart valve 910 (e.g., outer portion 918 of the valve cover 916).

As the inflatable balloon 1004 radially expands the prosthetic heart valve 910 to its expanded (functional) position, the prosthetic heart valve 910 radially expands the third portion 724 of the second section 712 of the coil 702 of the docking device 700. Thus, when the prosthetic heart valve 910 radially expands to its functional position, as illustrated in FIGS. 23-25, the docking device 700 is in its second deployed position. Specifically, in FIGS. 23-25, the third portion 724 of the second section 712 of the coil 702 has radially expanded and is substantially congruent with the second portion 722 of the second section 712 of the coil 702. As the third portion 724 radially expands, the second portion 722 may correspondingly retract proximally towards the posteromedial commissure 818 and/or A3/P3 position. Thus, the second portion 722 may extend over less of the anterior leaflet 808 when the docking device 700 is in the second deployed position than the first deployed position.

As is illustrated in FIG. 24, the anterior leaflet 808 and the posterior leaflet 814 may be squeezed between the docking device 700 and the prosthetic heart valve 910 when the prosthetic heart valve 910 is fully expanded to its functional size. Specifically, the anterior leaflet 808 may be sandwiched between the expandable sleeve 704 and/or the second section 712 of the coil 702 and the valve cover 916 of the prosthetic heart valve 910, such that the valve cover 916 of the prosthetic heart valve 910 directly physically contacts the atrial side of the anterior leaflet 808 and/or such that the expandable sleeve 704 and/or the second section 712 of the coil 702 directly physically contacts the ventricular side of the anterior leaflet 808. The posterior leaflet 814 may be similarly sandwiched between valve cover 916 and the docking device 700, except that the expandable sleeve 704 may not directly physically contact the posterior leaflet 814, in some examples. However, in other examples, the expandable sleeve 704 may extend past the anterolateral commissure 820, and thus may directly physically contact at least a portion of the posterior leaflet 814.

By squeezing the leaflets between the prosthetic heart valve 910 and the coil 702 and/or expandable sleeve 704, the docking device 700 may provide a seal between the prosthetic heart valve 910 and the leaflets of the native mitral valve 800 such that blood only flows through the leaflets 940 of the prosthetic heart valve 910 when the prosthetic heart valve assembly 950 is implanted at the mitral valve 800. Further, because the first portion 720 of the second section 712 of the coil 702 extends radially outwards from the other portions of the second section 712 of the coil 702 towards one or more of the commissures of the native mitral valve 800, the docking device 700 may reduce paravalvular leakage around the prosthetic heart valve 910. Specifically, the first portion 720 of the coil 702 and the expandable sleeve 704 may cover and/or seal openings in the native mitral valve 800 that may exist beyond the edges of the prosthetic heart valve 910, such as at and/or near the commissures of the native mitral valve 800.

In FIGS. 23-25, the prosthetic heart valve delivery apparatus 1000 has been removed, and only the guidewire 904 remains in FIG. 23. In FIGS. 24-25, the guidewire 904 has also been removed, and the prosthetic heart valve system 950 is fully functional.

ADDITIONAL EXAMPLES OF THE DISCLOSED TECHNOLOGY

Example 1. A docking device for a prosthetic heart valve comprising an inflow end, an outflow end, a support structure, and an expandable sleeve. The support structure is disposed between the inflow end and the outflow end and comprises an inflow section and an outflow section. The inflow section extends from the inflow end of the docking device toward the outflow end of the docking device and is configured to be positioned on an inflow side of a native heart valve. The outflow section extends between the outflow end of the docking device and the inflow section of the support structure and is configured to be positioned on an outflow side of the native heart valve. The outflow section comprises a first portion, a second portion, and a third portion. The first portion extends distally from the inflow section to the third portion, the third portion extends distally from the first portion to the second portion, and the second portion extends distally from the third portion to the outflow end of the docking device. The expandable sleeve covers at least a portion of the support structure. The expandable sleeve is movable from a compressed position to an expanded position when a crimping pressure is released. In the expanded position, the expandable sleeve extends at least 100 degrees over the first portion of the outflow section of the support structure.

Example 2. The docking device of any example herein, and particularly example 1, wherein the expandable sleeve extends over the first portion of the outflow section at least 100 degrees from the inflow section of the support structure towards the outflow end of the docking device and is configured to extend to and directly physically contact the third portion of the outflow section of the support structure when the expandable sleeve is in the expanded position.

Example 3. The docking device of any example herein, and particularly either example 1 or example 2, wherein the expandable sleeve extends over the inflow section of the support structure at least 100 from the outflow section of the support structure towards the inflow end of the docking device.

Example 4. The docking device of any example herein, and particularly any one of examples 1-3, wherein the expandable sleeve comprises a single continuous sleeve that extends between the inflow section and the outflow section of the support structure.

Example 5. The docking device of any example herein, and particularly example 4, wherein the expandable sleeve comprises a first portion that extends over the inflow section of the support structure, a second portion that extends over the outflow section of the support structure, and an intermediate portion that is disposed between the first portion and the second portion.

Example 6. The docking device of any example herein, and particularly example 5, wherein the expandable sleeve is tapered in the intermediate portion, such that the intermediate portion is narrower than the first portion and the second portion of the expandable sleeve.

Example 7. The docking device of any example herein, and particularly either example 5 or example 6, where the intermediate portion extends at least 45 degrees from the inflow section of the support structure over the first portion of the outflow section of the support structure towards the outflow end of the support structure.

Example 8. The docking device of any example herein, and particularly any one of examples 1-7, wherein the expandable sleeve comprises a proximal end and a distal end, and wherein the expandable sleeve extends towards the inflow end of the docking device from the distal end to the proximal end, and wherein the expandable sleeve is coupled to the support structure at the distal end.

Example 9. The docking device of any example herein, and particularly example 8, wherein the expandable sleeve is tapered at the distal end.

Example 10. The docking device of any example herein, and particularly example 1, wherein the expandable sleeve comprises two discrete sleeves that are separated from one another by a gap.

Example 11. The docking device of any example herein, and particularly example 10, wherein the expandable sleeve comprises a first sleeve that extends along the inflow section of the support structure and a second sleeve that extends along the outflow section of the support structure.

Example 12. The docking device of any example herein, and particularly example 11, wherein the gap is at least 45 degrees.

Example 13. The docking device of any example herein, and particularly either example 11 or example 12, wherein the first sleeve comprises a proximal end and a distal end, wherein the first sleeve extends towards the inflow end of the docking device from the distal end to the proximal end, and wherein the first sleeve is coupled to the support structure at the distal end.

Example 14. The docking device of any example herein, and particularly example 13, wherein the first sleeve is tapered at the distal end.

Example 15. The docking device of any example herein, and particularly any one of examples 11-14, wherein the second sleeve comprises a proximal end and a distal end, wherein the second sleeve extends towards the inflow end of the docking device from the distal end to the proximal end, and wherein the second sleeve is coupled to the support structure at the distal end.

Example 16. The docking device of any example herein, and particularly example 15, wherein the second sleeve is tapered at one or more of the distal end and the proximal end.

Example 17. The docking device of any example herein, and particularly any one of examples 1-16, wherein the first portion of the support structure has a different geometry than the third portion of the support structure.

Example 18. The docking device of any example herein, and particularly example 17, wherein the first portion has a different shape than the third portion of the support structure when viewed in a plane perpendicular to a longitudinal axis of the docking device.

Example 19. The docking device of any example herein, and particularly either example 17 or example 18, wherein the first portion has a different size than the third portion of the support structure when viewed in a plane perpendicular to a/the longitudinal axis of the docking device.

Example 20. The docking device of any example herein, and particularly example 19, wherein the first portion is larger than the third portion of the support structure when viewed in the plane perpendicular to the longitudinal axis of the docking device.

Example 21. A docking device for a prosthetic heart valve comprising an atrial end, a ventricular end, a support structure, and an expandable sleeve. The support structure is disposed between the atrial end and the ventricular end and comprises an atrial section and a ventricular section. The atrial section extends from the atrial end of the docking device toward the ventricular end of the docking device and is configured to be positioned on an atrial side of a native mitral valve. The ventricular section extends between the ventricular end of the docking device and the atrial section of the support structure and is configured to be positioned on a ventricular side of the native mitral valve. The ventricular section comprises a first portion, a second portion, and a third portion. The first portion extends distally from the atrial section to the third portion, the third portion extends distally from the first portion to the second portion, and the second portion extends distally from the third portion to the ventricular end of the docking device. The expandable sleeve covers at least a portion of the support structure and is configured to extend at least 100 degrees over a ventricular side of an anterior leaflet of the native mitral valve when the docking device is implanted at the native mitral valve.

Example 22. The docking device of any example herein, and particularly example 21, wherein the expandable sleeve comprises a single continuous sleeve that extends between the atrial section and the ventricular section of the support structure.

Example 23. The docking device of any example herein, and particularly example 22, wherein the expandable sleeve comprises a first portion that extends over the atrial section of the support structure, a second portion that extends over the ventricular section of the support structure, and an intermediate portion that is disposed between the first portion and the second portion.

Example 24. The docking device of any example herein, and particularly example 23, wherein the expandable sleeve is tapered in the intermediate portion, such that the intermediate portion is narrower than the first portion and the second portion of the expandable sleeve.

Example 25. The docking device of any example herein, and particularly either example 23 or example 24, where the intermediate portion extends at least 45 degrees from the atrial section of the support structure over the first portion of the ventricular section of the support structure towards the ventricular end of the support structure.

Example 26. The docking device of any example herein, and particularly any one of examples 21-25, wherein the expandable sleeve comprises a proximal end and a distal end, and wherein the expandable sleeve extends towards the atrial end of the docking device from the distal end to the proximal end, and wherein the expandable sleeve is coupled to the support structure at the distal end.

Example 27. The docking device of any example herein, and particularly example 26, wherein the expandable sleeve is tapered at the distal end.

Example 28. The docking device of any example herein, and particularly example 21, wherein the expandable sleeve comprises two discrete sleeves that are separated from one another by a gap.

Example 29. The docking device of any example herein, and particularly example 28, wherein the expandable sleeve comprises a first sleeve that extends along the atrial section of the support structure and a second sleeve that extends along the ventricular section of the support structure.

Example 30. The docking device of any example herein, and particularly example 29, wherein the gap is at least 45 degrees.

Example 31. The docking device of any example herein, and particularly either example 29 or example 30, wherein the first sleeve comprises a proximal end and a distal end, wherein the first sleeve extends towards the atrial end of the docking device from the distal end to the proximal end, and wherein the first sleeve is coupled to the support structure at the distal end.

Example 32. The docking device of any example herein, and particularly example 31, wherein the first sleeve is tapered at the distal end.

Example 33. The docking device of any example herein, and particularly any one of examples 29-32, wherein the second sleeve comprises a proximal end and a distal end, wherein the second sleeve extends towards the atrial end of the docking device from the distal end to the proximal end, and wherein the second sleeve is coupled to the support structure at the distal end.

Example 34. The docking device of any example herein, and particularly example 33, wherein the second sleeve is tapered at one or more of the distal end and the proximal end.

Example 35. The docking device of any example herein, and particularly any one of examples 21-34, wherein the first portion of the support structure has a different geometry than the third portion of the support structure.

Example 36. The docking device of any example herein, and particularly example 35, wherein the first portion has a different shape than the third portion of the support structure when viewed in a plane perpendicular to a longitudinal axis of the docking device.

Example 37. The docking device of any example herein, and particularly either example 35 or example 36, wherein the first portion has a different size than the third portion of the support structure when viewed in a plane perpendicular to a/the longitudinal axis of the docking device.

Example 38. The docking device of any example herein, and particularly example 37, wherein the first portion is larger than the third portion of the support structure when viewed in the plane perpendicular to the longitudinal axis of the docking device.

Example 39. The docking device of any example herein, and particularly any one of examples 21-38, wherein the expandable sleeve is configured to extend to an anterolateral commissure of the native mitral valve over the first portion of the support structure.

Example 40. The docking device of any example herein, and particularly any one of examples 21-39, wherein the expandable sleeve is movable from a compressed position to an expanded position and is configured to move to the expanded position from the compressed position when a crimping pressure is released from the expandable sleeve, and wherein in the expanded position, the expandable sleeve extends at least 100 degrees over the first portion of the ventricular section of the support structure.

Example 41. The docking device of any example herein, and particularly example 40, wherein the expandable sleeve is configured to extend to and directly physically contact the third portion of the ventricular section of the support structure when the expandable sleeve is in the expanded position.

Example 42. A docking device for a prosthetic heart valve comprising an atrial end, a ventricular end, a support structure, and an expandable sleeve. The support structure is disposed between the atrial end and the ventricular end and comprises an atrial section and a ventricular section. The atrial section extends from the atrial end of the docking device toward the ventricular end of the docking device and is configured to be positioned on an atrial side of a native mitral valve. The ventricular section extends from the ventricular end of the docking device toward the atrial end of the docking device and is configured to be positioned on a ventricular side of the native mitral valve. The ventricular section comprises a first turn, a second turn, and one or more intermediate turns. The first turn is disposed closer to the atrial section than the second turn, and the one or more intermediate turns are disposed between the first and second turns. The support structure is configured to move from a delivery configuration to a deployed configuration when the support structure is released from a docking device delivery apparatus. In the deployed configuration, the first turn comprises a different geometry than the one or more intermediate turns. The expandable sleeve covers at least a portion of the support structure.

Example 43. The docking device of any example herein, and particularly example 42, wherein, when the support structure is in the deployed configuration, the first turn is larger than the one or more intermediate turns when viewed in a plane perpendicular to a longitudinal axis of the docking device.

Example 44. The docking device of any example herein, and particularly either example 42 or example 43, wherein the first turn extends radially outwardly beyond the one or more intermediate turns when the support structure is in the deployed configuration.

Example 45. The docking device of any example herein, and particularly any one of examples 42-44, wherein, when the support structure is in the deployed configuration, the first turn defines a cross-sectional area of the docking device that is at least 15% larger than a cross-sectional area defined by the one or more intermediate turns.

Example 46. The docking device of any example herein, and particularly any one of examples 42-45, wherein, when the support structure is in the deployed configuration, the first turn has a different shape than the one or more intermediate turns when viewed in a plane perpendicular to a/the longitudinal axis of the docking device.

Example 47. The docking device of any example herein, and particularly any one of examples 42-46, wherein, when the support structure is in the deployed configuration, the first turn is substantially D-shaped when viewed in a plane perpendicular to a/the longitudinal axis of the docking device.

Example 48. The docking device of any example herein, and particularly any one of examples 42-46, wherein, when the support structure is in the deployed configuration, the first turn is substantially crescent-shaped when viewed in a plane perpendicular to a/the longitudinal axis of the docking device and comprises a convex edge that is configured to contact a ventricular side of a posterior leaflet of the native mitral valve and a concave edge that is configured to contact a ventricular side of an anterior leaflet of the native mitral valve.

Example 49. The docking device of any example herein, and particularly any one of examples 42-46, wherein, when the support structure is in the deployed configuration, the first turn is substantially the same shape as an annulus of the native mitral valve when viewed in a plane perpendicular to a/the longitudinal axis of the docking device.

Example 50. The docking device of any example herein, and particularly any one of examples 42-46, wherein, when the support structure is in the deployed configuration, the first turn is circular when viewed in a plane perpendicular to a/the longitudinal axis of the docking device.

Example 51. The docking device of any example herein, and particularly any one of examples 42-50, wherein, when the support structure is in the deployed configuration, the one or more intermediate turns are circular when viewed in a plane perpendicular to a/the longitudinal axis of the docking device.

Example 52. The docking device of any example herein, and particularly any one of examples 42-51, wherein the support structure is configured to move from the deployed configuration to a final assembled configuration when a prosthetic heart valve is expanded within the docking device, and wherein the one or more intermediate turns radially expand when the support structure moves from the deployed configuration to the final assembled configuration.

Example 53. The docking device of any example herein, and particularly example 52, wherein the first turn maintains a different geometry than the one or more intermediate turns in the final assembled configuration.

Example 54. The docking device of any example herein, and particularly either example 52 or example 53, wherein, when the support structure is in the final assembled configuration, the first turn is larger than the one or more intermediate turns when viewed in a plane perpendicular to a/the longitudinal axis of the docking device.

Example 55. The docking device of any example herein, and particularly any one of examples 52-54, wherein, when the support structure is in the final assembled configuration, the first turn extends radially outwardly beyond the one or more intermediate turns.

Example 56. The docking device of any example herein, and particularly any one of examples 52-55, wherein, when the support structure is in the final assembled configuration, the first turn comprises a different shape than the one or more intermediate turns when viewed in a plane perpendicular to a/the longitudinal axis of the docking device.

Example 57. The docking device of any example herein, and particularly any one of examples 52-56, wherein, when the support structure is in the final assembled configuration, the one or more intermediate turns are circular when viewed in a plane perpendicular to a/the longitudinal axis of the docking device, and the first turn is non-circular when viewed in the plane perpendicular to the longitudinal axis of the docking device.

Example 58. The docking device of any example herein, and particularly any one of examples 52-57, wherein, when the support structure is in the final assembled configuration, the first turn is substantially D-shaped when viewed in a plane perpendicular to the longitudinal axis of the docking device.

Example 59. The docking device of any example herein, and particularly any one of examples 52-57, wherein, when the support structure is in the final assembled configuration, the first turn is substantially crescent-shaped when viewed in a plane perpendicular to the longitudinal axis of the docking device.

Example 60. The docking device of any example herein, and particularly any one of example 52-57, wherein, when the support structure is in the final assembled configuration, the first turn is substantially the same shape as an annulus of the native mitral valve when viewed in a plane perpendicular to a/the longitudinal axis of the docking device.

Example 61. The docking device of any example herein, and particularly any one of examples 52-60, wherein the second turn extends radially outwardly beyond the one or more intermediate turns when the support structure is in the deployed configuration.

Example 62. The docking device of any example herein, and particularly any one of examples 52-61, wherein the one or more intermediate turns and the second turn are substantially congruent when the support structure is in the final assembled configuration.

Example 63. The docking device of any example herein, and particularly any one of examples 42-62, wherein the first turn is configured to extend from a posteromedial commissure of the native mitral valve over a/the ventricular side of an/the anterior leaflet of the native mitral valve to an anterolateral commissure of the native mitral valve.

Example 64. The docking device of any example herein, and particularly any one of examples 42-63, wherein the first turn extends at least 180 degrees, the one or more intermediate turns extend at least 360 degrees, and the second turn extends at least 90 degrees.

Example 65. The docking device of any example herein, and particularly any one of examples 42-64, wherein the expandable sleeve extends at least 100 degrees along the first turn of the support structure.

Example 66. The docking device of any example herein, and particularly any one of examples 42-65, wherein the expandable sleeve is movable between a compressed position and an expanded position, and wherein the expandable sleeve radially expands and axially shortens when moving from the compressed position to the expanded position.

Example 67. A docking device for a prosthetic heart valve comprising an inflow end, an outflow end, a support structure, and an expandable sleeve that covers at least a portion of the support structure. The support structure is disposed between the inflow end and the outflow end and comprises and inflow section and an outflow section. The inflow section extends from the inflow end of the docking device toward the outflow end of the docking device and is configured to be positioned on an inflow side of a native heart valve. The outflow section extends from the outflow end of the docking device toward the inflow end of the docking device and is configured to be positioned on an outflow side of the native heart valve. The outflow section comprises a first portion, a second portion, and a third portion. The first portion is disposed closer to the inflow section than the second portion, and the third portion is disposed between the first and second portions. The support structure is movable from a delivery configuration to a deployed configuration. In the deployed configuration, the first portion comprises a different geometry than the third portion.

Example 68. The docking device of any example herein, and particularly example 67, wherein, when the support structure is in the deployed configuration, the first portion is larger than the third portion when viewed in a plane perpendicular to a longitudinal axis of the docking device.

Example 69. The docking device of any example herein, and particularly either example 67 or example 68, wherein the first portion extends radially outwardly beyond the third portion when the support structure is in the deployed configuration.

Example 70. The docking device of any example herein, and particularly any one of examples 67-69, wherein, when the support structure is in the deployed configuration, the first portion defines a cross-sectional area of the docking device that is at least 15% larger than a cross-sectional area defined by the third portion.

Example 71. The docking device of any example herein, and particularly any one of examples 67-70, wherein, when the support structure is in the deployed configuration, the first portion has a different shape than the third portion when viewed in a plane perpendicular to a/the longitudinal axis of the docking device.

Example 72. The docking device of any example herein, and particularly any one of examples 67-71, wherein, when the support structure is in the deployed configuration, the first portion is substantially D-shaped when viewed in a plane perpendicular to a/the longitudinal axis of the docking device.

Example 73. The docking device of any example herein, and particularly any one of examples 67-71, wherein, when the support structure is in the deployed configuration, the first portion is substantially crescent-shaped when viewed in a plane perpendicular to a/the longitudinal axis of the docking device and comprises a convex edge that is configured to contact a ventricular side of a posterior leaflet of the native heart valve and a concave edge that is configured to contact a ventricular side of an anterior leaflet of the native heart valve.

Example 74. The docking device of any example herein, and particularly any one of examples 67-71, wherein, when the support structure is in the deployed configuration, the first portion is substantially the same shape as an annulus of the native heart valve when viewed in a plane perpendicular to a/the longitudinal axis of the docking device.

Example 75. The docking device of any example herein, and particularly any one of examples 64-71, wherein, when the support structure is in the deployed configuration, the first portion is circular when viewed in a plane perpendicular to a/the longitudinal axis of the docking device.

Example 76. The docking device of any example herein, and particularly any one of examples 67-75, wherein, when the support structure is in the deployed configuration, the third portion is circular when viewed in a plane perpendicular to a/the longitudinal axis of the docking device.

Example 77. The docking device of any example herein, and particularly any one of examples 67-76, wherein the support structure is configured to move from the deployed configuration to a final assembled configuration when a prosthetic heart valve is expanded within the docking device, and wherein the third portion radially expands when the support structure moves from the deployed configuration to the final assembled configuration.

Example 78. The docking device of any example herein, and particularly example 77, wherein the first portion maintains a different geometry than the third portion in the final assembled configuration.

Example 79. The docking device of any example herein, and particularly either example 77 or example 78, wherein, when the support structure is in the final assembled configuration, the first portion is larger than third portion when viewed in a plane perpendicular to a/the longitudinal axis of the docking device.

Example 80. The docking device of any example herein, and particularly any one of examples 77-79, wherein, when the support structure is in the final assembled configuration, the first portion extends radially outwardly beyond the third portion.

Example 81. The docking device of any example herein, and particularly any one of examples 77-80, wherein, when the support structure is in the final assembled configuration, the first portion comprises a different shape than the third portion when viewed in a plane perpendicular to a/the longitudinal axis of the docking device.

Example 82. The docking device of any example herein, and particularly any one of examples 77-81, wherein, when the support structure is in the final assembled configuration, the third portion is circular when viewed in a plane perpendicular to a/the longitudinal axis of the docking device, and the first portion is non-circular when viewed in the plane perpendicular to the longitudinal axis of the docking device.

Example 83. The docking device of any example herein, and particularly any one of examples 77-82, wherein, when the support structure is in the final assembled configuration, the first portion is substantially D-shaped when viewed in a plane perpendicular to the longitudinal axis of the docking device.

Example 84. The docking device of any example herein, and particularly any one of examples 77-82, wherein, when the support structure is in the final assembled configuration, the first portion is substantially crescent-shaped when viewed in a plane perpendicular to the longitudinal axis of the docking device.

Example 85. The docking device of any example herein, and particularly any one of examples 77-82, wherein, when the support structure is in the final assembled configuration, the first portion is substantially the same shape as an annulus of the native heart valve when viewed in a plane perpendicular to a/the longitudinal axis of the docking device.

Example 86. The docking device of any example herein, and particularly any one of examples 77-85, wherein the second portion extends radially outwardly beyond the third portion when the support structure is in the deployed configuration.

Example 87. The docking device of any example herein, and particularly any one of examples 77-86, wherein the third portion and the second portion are substantially congruent when the support structure is in the final assembled configuration.

Example 88. The docking device of any example herein, and particularly any one of examples 77-87, wherein the first portion extends at least 180 degrees, the third portion extends at least 360 degrees, and the second portion extends at least 90 degrees.

Example 89. The docking device of any example herein, and particularly any one of examples 77-88, wherein the expandable sleeve extends at least 100 degrees along the first portion of the support structure.

Example 90. The docking device of any example herein, and particularly any one of examples 77-89, wherein the expandable sleeve is movable between a compressed position and an expanded position, and wherein the expandable sleeve radially expands and axially shortens when moving from the compressed position to the expanded position.

Example 91. A prosthetic heart valve assembly comprising a docking device and a prosthetic heart valve. The docking device comprises an atrial end, a ventricular end, a support structure disposed between the atrial end and the ventricular end, and an expandable sleeve that covers at least a portion of the support structure. The support structure comprises an atrial section and a ventricular section. The atrial section extends from the atrial end of the docking device toward the ventricular end of the docking device and is configured to be positioned on an atrial side of a native mitral valve. The ventricular section extends from the ventricular end of the docking device toward the atrial end of the docking device and is configured to be positioned on a ventricular side of the native mitral valve. The ventricular section comprises a first turn, a second turn, and one or more intermediate turns. The first turn is disposed closer to the atrial section than the second turn, and the one or more intermediate turns are disposed between the first and second turns. The support structure is movable from a delivery configuration to a deployed configuration. In the deployed configuration, the first turn comprises a different geometry than the one or more intermediate turns when the first turn and the one or more intermediate turns are released from a docking device delivery apparatus and are deployed at the native mitral valve. The prosthetic heart valve is configured to be disposed within the docking device and comprises a frame and a plurality of leaflets coupled to the frame. The frame is configured to be radially expanded to an expanded position from a compressed position within the docking device. The plurality of leaflets is configured to selectively open to permit blood to flow through the prosthetic heart valve.

Example 92. The prosthetic heart valve assembly of any example herein, and particularly example 91, wherein, when the prosthetic heart valve is in the expanded position, the docking device and the prosthetic heart valve are configured to sandwich leaflets of the native mitral valve there-between.

Example 93. The prosthetic heart valve assembly of any example herein, and particularly example 92, wherein the expandable sleeve is configured to directly physically contact a ventricular side of the leaflets of the native mitral valve and an atrial side of the leaflets of the native mitral valve.

Example 94. The prosthetic heart valve assembly of any example herein, and particularly any one of examples 91-93, wherein the expandable sleeve is configured to extend at least 100 degrees over a ventricular side of an anterior leaflet of the native mitral valve towards an anterolateral commissure of the native mitral valve.

Example 95. The prosthetic heart valve assembly of any example herein, and particularly any one of examples 91-94, wherein the prosthetic heart valve is configured to directly physically contact the atrial side of the native mitral valve when in the expanded position, and wherein the ventricular section of the support structure of the docking device is configured to directly physically contact the ventricular side of the native mitral valve.

Example 96. The prosthetic heart valve assembly of any example herein, and particularly any one of examples 91-95, wherein the support structure is configured to cross over between the atrial and ventricular sides of the native mitral valve at a posteromedial commissure of the native mitral valve.

Example 97. The prosthetic heart valve assembly of any example herein, and particularly any one of examples 91-96, wherein the expandable sleeve is configured to extend to and directly physically contact the one or more intermediate turns of the ventricular section of the support structure.

Example 98. The prosthetic heart valve assembly of any example herein, and particularly any one of examples 91-96, wherein, the prosthetic heart valve is configured to move the docking device from a deployed configuration to a final assembled configuration when the prosthetic heart valve is expanded to its expanded position.

Example 99. The prosthetic heart valve assembly of any example herein, and particularly example 98, wherein the one or more intermediate turns of the ventricular section of the support structure are configured to radially expand when the docking device moves from the deployed configuration to the final assembled configuration.

Example 100. The prosthetic heart valve assembly of any example herein, and particularly example 99, wherein, when the docking device is in the final assembled configuration, the first turn extends radially outwardly beyond the one or more intermediate turns.

Example 101. The prosthetic heart valve assembly of any example herein, and particularly either example 99 or example 100, wherein, when the docking device is in the final assembled configuration, the first turn defines a larger cross-sectional area than the one or more intermediate turns.

Example 102. The prosthetic heart valve assembly of any example herein, and particularly any one of examples 99-101, wherein, when the docking device is in the final assembled configuration, the first turn has a different shape than the one or more intermediate turns when viewed in a plane perpendicular to a/the longitudinal axis of the docking device.

Example 103. The prosthetic heart valve assembly of any example herein, and particularly any one of examples 99-102, wherein, when the docking device is in the final assembled configuration, the first turn is substantially D-shaped when viewed in a plane perpendicular to a/the longitudinal axis of the docking device.

Example 104. The prosthetic heart valve assembly of any example herein, and particularly any one of examples 99-102, wherein, when the docking device is in the final assembled configuration, the first turn is substantially crescent-shaped when viewed in a plane perpendicular to a/the longitudinal axis of the docking device and comprises a convex edge that is configured to contact a ventricular side of a posterior leaflet of the native mitral valve and a concave edge that is configured to contact a/the ventricular side of an/the anterior leaflet of the native mitral valve.

Example 105. The prosthetic heart valve assembly of any example herein, and particularly any one of examples 99-102, wherein, when the docking device is in the final assembled configuration, the first turn is substantially the same shape as an annulus of the native mitral valve when viewed in a plane perpendicular to a/the longitudinal axis of the docking device.

Example 106. A prosthetic heart valve assembly comprising a docking device and a prosthetic heart valve configured to be disposed within the docking device. The docking device comprises an atrial end, a ventricular end, a support structure disposed between the atrial end and the ventricular end, and an expandable sleeve that covers at least a portion of the support structure. The support structure comprises an atrial section and a ventricular section. The atrial section extends from the atrial end of the docking device toward the ventricular end of the docking device and is configured to be positioned on an atrial side of a native mitral valve. The ventricular section extends between the ventricular end of the docking device and the atrial section of the support structure and is configured to be positioned on a ventricular side of the native mitral valve. The ventricular section comprises a first portion, a second portion, and a third portion. The first portion extends distally from the atrial section to the third portion, the third portion extends distally from the first portion to the second portion, and the second portion extends distally from the third portion to the ventricular end of the docking device. The expandable sleeve is movable from a compressed position to an expanded position when a crimping pressure is released. In the expanded position, the expandable sleeve extends at least 100 degrees over the first portion of the ventricular section of the support structure. The prosthetic heart valve comprises a radially expandable and compressible frame and a plurality of leaflets coupled to the frame and configured to selectively open to permit blood to flow through the prosthetic heart valve.

Example 107. The prosthetic heart valve assembly of any example herein, and particularly example 106, wherein the expandable sleeve comprises a single continuous sleeve that extends between the atrial section and the ventricular section of the support structure.

Example 108. The prosthetic heart valve assembly of any example herein, and particularly example 107, wherein the expandable sleeve comprises a first portion that extends over the atrial section of the support structure and is configured to directly physically contact the atrial side of the native mitral valve, a second portion that extends over the ventricular section of the support structure and is configured to directly physically contact the ventricular side of the native mitral valve, and an intermediate portion that is disposed between the first portion and the second portion.

Example 109. The prosthetic heart valve assembly of any example herein, and particularly example 108, wherein the expandable sleeve is tapered in the intermediate portion, such that the intermediate portion is narrower than the first portion and the second portion of the expandable sleeve.

Example 110. The prosthetic heart valve assembly of any example herein, and particularly either example 108 or example 109, where the intermediate portion extends at least 45 degrees from the atrial section of the support structure over the first portion of the ventricular section of the support structure towards the ventricular end of the support structure and is configured to directly physically contact a ventricular side of an anterior leaflet of the native mitral valve and be positioned adjacent to a left ventricular outflow tract.

Example 111. The prosthetic heart valve assembly of any example herein, and particularly any one of examples 106-110, wherein the expandable sleeve comprises a proximal end and a distal end, and wherein the expandable sleeve extends towards the atrial end of the docking device from the distal end to the proximal end, and wherein the expandable sleeve is coupled to the support structure at the distal end.

Example 112. The prosthetic heart valve assembly of any example herein, and particularly example 111, wherein the expandable sleeve is tapered at the distal end.

Example 113. The prosthetic heart valve assembly of any example herein, and particularly example 106, wherein the expandable sleeve comprises two discrete sleeves that are separated from one another by a gap, wherein the gap is configured to be positioned adjacent to a ventricular side of an anterior leaflet of the mitral valve and a left ventricular outflow tract.

Example 114. The prosthetic heart valve assembly of any example herein, and particularly example 113, wherein the expandable sleeve comprises a first sleeve that extends along the atrial section of the support structure and a second sleeve that extends along the ventricular section of the support structure.

Example 115. The prosthetic heart valve assembly any example herein, and particularly example 114, wherein the gap is at least 45 degrees.

Example 116. The prosthetic heart valve assembly of any example herein, and particularly either example 114 or example 115, wherein the first sleeve comprises a proximal end and a distal end, wherein the first sleeve extends towards the atrial end of the docking device from the distal end to the proximal end, and wherein the first sleeve is coupled to the support structure at the distal end.

Example 117. The prosthetic heart valve assembly of any example herein, and particularly example 116, wherein the first sleeve is tapered at the distal end.

Example 118. The prosthetic heart valve assembly of any example herein, and particularly any one of examples 114-117, wherein the second sleeve comprises a proximal end and a distal end, wherein the second sleeve extends towards the atrial end of the docking device from the distal end to the proximal end, and wherein the second sleeve is coupled to the support structure at the distal end.

Example 119. The prosthetic heart valve assembly of any example herein, and particularly example 118, wherein the second sleeve is tapered at one or more of the distal end and the proximal end.

Example 120. The prosthetic heart valve assembly of any example herein, and particularly any one of examples 106-119, wherein the first portion of the support structure has a different geometry than the intermediate portion of the support structure.

Example 121. The prosthetic heart valve assembly of any example herein, and particularly example 120, wherein the first portion has a different shape than the third portion of the support structure when viewed in a plane perpendicular to a longitudinal axis of the docking device.

Example 122. The prosthetic heart valve assembly of any example herein, and particularly either example 120 or example 121, wherein the first portion has a different size than the third portion of the support structure when viewed in a plane perpendicular to a/the longitudinal axis of the docking device.

Example 123. The prosthetic heart valve assembly of any example herein, and particularly example 122, wherein the first portion is larger than the third portion of the support structure when viewed in the plane perpendicular to the longitudinal axis of the docking device.

Example 124. A method comprising wrapping at least one complete turn of a coil around an outflow side of two or more leaflets of a native heart valve, the at least one complete turn comprising a first geometry, wrapping a second turn of the coil around the outflow side of the two or more leaflets of the native heart valve, the second turn comprising a second geometry different than the first geometry, and radially expanding an expandable sleeve around at least a portion of the second turn of the coil.

Example 125. The method of any example herein, and particularly example 124, wherein the wrapping the second turn of the coil around the outflow side of the two or more leaflets of the native heart valve comprises extending the second turn radially outwardly relative to the at least one complete turn.

Example 126. The method of any example herein, and particularly either example 124 or example 125, wherein the wrapping the second turn of the coil around the outflow side of the two or more leaflets of the native heart valve comprises wrapping the second turn around the outflow side of the two or more leaflets of the native heart valve in a substantially D-shaped pattern when viewed from a plane perpendicular to a longitudinal axis of the coil.

Example 127. The method of any example herein, and particularly either example 124 or example 125, wherein the wrapping the second turn of the coil around the outflow side of the two or more leaflets of the native heart valve comprises wrapping the second turn around the outflow side of the two or more leaflets of the native heart valve in a substantially crescent-shaped pattern when viewed from a plane perpendicular to a longitudinal axis of the coil.

Example 128. The method of any example herein, and particularly either example 124 or example 125, wherein the native heart valve is a native mitral valve, and wherein the wrapping the second turn of the coil around the outflow side of the two or more leaflets of the native heart valve comprises wrapping the second turn around a ventricular side of an anterior leaflet of the mitral valve under an anterolateral commissure of the native mitral valve.

Example 129. The method of any example herein, and particularly any one of examples 124-127, wherein the second turn is larger than the at least one complete turn when viewed from a plane perpendicular to a/the longitudinal axis of the coil.

Example 130. The method of any example herein, and particularly any one of examples 124-129, wherein the second turn is a different shape than the at least one complete turn when viewed from a plane perpendicular to a/the longitudinal axis of the coil.

Example 131. The method of any example herein, and particularly any one of examples 124-130, wherein the radially expanding the expandable sleeve comprises releasing the expandable sleeve from a delivery shaft of a docking device delivery apparatus.

Example 132. The method of any example herein, and particularly any one of examples 124-130, wherein the radially expanding the expandable sleeve comprises retracting a sleeve shaft of a docking device delivery apparatus from the expandable sleeve.

Example 133. The method of any example herein, and particularly any one of examples 124-132, wherein the radially expanding the expandable sleeve comprises radially expanding the expandable sleeve around at least 100 degrees of the outflow side of the two or more leaflets of the native heart valve such that the expandable sleeve directly physically contacts the outflow side of the two or more leaflets.

In view of the many possible ways in which the principles of the disclosure may be applied, it should be recognized that the illustrated configurations depict examples of the disclosed technology and should not be taken as limiting the scope of the disclosure nor the claims. Rather, the scope of the claimed subject matter is defined by the following claims and their equivalents.

The invention claimed is:

1. A docking device for a prosthetic heart valve, the docking device comprising:

an inflow end;

an outflow end;

a support structure disposed between the inflow end and the outflow end, the support structure comprising:

an inflow section extending from the inflow end of the docking device toward the outflow end of the docking device and configured to be positioned on an inflow side of a native heart valve; and an outflow section extending between the outflow end of the docking device and the inflow section of the support structure and configured to be positioned on an outflow side of the native heart valve, wherein the outflow section comprises a first portion, a second portion, and a third portion, wherein the first portion extends distally from the inflow section to the third portion, wherein the third portion extends distally from the first portion to the second portion, and wherein the second portion extends distally from the third portion to the outflow end of the docking device; and an expandable sleeve that covers at least a portion of the support structure and comprises a first end that is fixedly coupled to the support structure and a second end that is configured to move axially relative to the support structure, wherein the expandable sleeve is movable from a compressed position to an expanded position when a crimping pressure is released and the second end of the expandable sleeve moves axially relative to the support structure, and wherein in the expanded position, the expandable sleeve extends at least 100 degrees over the first portion of the outflow section of the support structure.

2. The docking device of claim 1, wherein the expandable sleeve extends over the first portion of the outflow section at least 100 degrees from the inflow section of the support structure towards the outflow end of the docking device and is configured to extend to and directly physically contact the third portion of the outflow section of the support structure when the expandable sleeve is in the expanded position.

3. The docking device of claim 1, wherein the expandable sleeve extends over the inflow section of the support structure at least 100 degrees from the outflow section of the support structure towards the inflow end of the docking device.

4. The docking device of claim 1, wherein the expandable sleeve comprises a single continuous sleeve that extends between the inflow section and the outflow section of the support structure.

5. The docking device of claim 4, wherein the expandable sleeve comprises a first portion that extends over the inflow section of the support structure, a second portion that extends over the outflow section of the support structure, and an intermediate portion that is disposed between the first portion and the second portion.

6. The docking device of claim 5, wherein the expandable sleeve is tapered in the intermediate portion, such that the intermediate portion is narrower than the first portion and the second portion of the expandable sleeve.

7. The docking device of claim 5, wherein the intermediate portion extends at least 45 degrees from the inflow section of the support structure over the first portion of the outflow section of the support structure towards the outflow end of the support structure.

8. The docking device of claim 1, wherein at least one of the first and second ends of the expandable sleeve is tapered.

9. The docking device of claim 1, wherein the expandable sleeve comprises two discrete sleeves that are separated from one another by a gap.

10. The docking device of claim 9, wherein the expandable sleeve comprises a first sleeve that extends along the inflow section of the support structure and a second sleeve that extends along the outflow section of the support structure.

11. The docking device of claim 10, wherein the gap is at least 45 degrees.

12. The docking device of claim 10, wherein the first sleeve comprises a proximal end and a distal end, wherein the first sleeve extends towards the inflow end of the docking device from the distal end to the proximal end, and wherein the first sleeve is coupled to the support structure at the distal end.

13. The docking device of claim 12, wherein the first sleeve is tapered at the distal end.

14. The docking device of claim 10, wherein the second sleeve comprises a proximal end and a distal end, wherein the second sleeve extends towards the inflow end of the docking device from the distal end to the proximal end, and wherein the second sleeve is coupled to the support structure at the distal end.

15. The docking device of claim 14, wherein the second sleeve is tapered at one or more of the distal end and the proximal end.

16. The docking device of claim 1, wherein the first portion of the support structure has a different geometry than the third portion of the support structure.

17. The docking device of claim 16, wherein the first portion has a different shape than the third portion of the support structure when viewed in a plane perpendicular to a longitudinal axis of the docking device.

18. The docking device of claim 16, wherein the first portion has a different size than the third portion of the support structure when viewed in a plane perpendicular to a/the longitudinal axis of the docking device.

19. The docking device of claim 18, wherein the first portion is larger than the third portion of the support structure when viewed in the plane perpendicular to the longitudinal axis of the docking device.

* * * * *